US009919044B2

(12) United States Patent
van Rijn et al.

(10) Patent No.: US 9,919,044 B2
(45) Date of Patent: Mar. 20, 2018

(54) VACCINES FOR DISEASES CAUSED BY VIRUSES OF THE FAMILY OF REOVIRIDAE

(71) Applicant: Stichting Wageningen Research, Wageningen (NL)

(72) Inventors: Petrus Antonius van Rijn, Lelystad (NL); Hendricus Gerardus Petrus van Gennip, Swifterbant (NL); Sandra Gerarda Petra van de Water, Lelystad (NL); Femke Feenstra, Amersfoort (NL)

(73) Assignee: Stichting Wageningen Research, Wageningen (NL)

( * ) Notice: Subject to any disclaimer, the term of this patent is extended or adjusted under 35 U.S.C. 154(b) by 0 days.

(21) Appl. No.: 14/890,994

(22) PCT Filed: May 16, 2014

(86) PCT No.: PCT/NL2014/050312
§ 371 (c)(1),
(2) Date: Nov. 13, 2015

(87) PCT Pub. No.: WO2014/185784
PCT Pub. Date: Nov. 20, 2014

(65) Prior Publication Data
US 2016/0158342 A1    Jun. 9, 2016

(30) Foreign Application Priority Data

May 16, 2013  (EP) ..................................... 13168061
Nov. 28, 2013 (EP) ..................................... 13194912

(51) Int. Cl.
*A61K 39/15* (2006.01)
*C12N 7/04* (2006.01)
*A61K 39/12* (2006.01)
*C12N 7/00* (2006.01)
*A61K 39/00* (2006.01)

(52) U.S. Cl.
CPC .............. *A61K 39/15* (2013.01); *A61K 39/12* (2013.01); *C12N 7/00* (2013.01); *C12N 7/04* (2013.01); *A61K 2039/525* (2013.01); *A61K 2039/5252* (2013.01); *A61K 2039/5254* (2013.01); *A61K 2039/552* (2013.01); *C12N 2720/12051* (2013.01); *C12N 2720/12121* (2013.01); *C12N 2720/12134* (2013.01); *C12N 2720/12151* (2013.01); *C12N 2720/12162* (2013.01); *C12N 2720/12164* (2013.01); *C12N 2720/12171* (2013.01); *C12N 2720/12251* (2013.01); *C12N 2720/12351* (2013.01)

(58) Field of Classification Search
None
See application file for complete search history.

(56) References Cited

FOREIGN PATENT DOCUMENTS

WO    WO2009/068870    6/2009

OTHER PUBLICATIONS

Celma et al. Journal of Virology 2011, vol. 85, pp. 4783-4791.*
Celma et al. J of Virology 2011 vol. 85, No. 10, pp. 4783-4791.*
Bansal et al., "Membrane Organization of Bluetongue Virus Nonstructural Glycoprotein NS3," Journal of Virology, 72:3362-3369 (1998).
Barros et al., "A DIVA System Based on the Detection of Antibodies to Non-Structural Protein 3 (NS3) of Bluetongue Virus," Veterinary Microbiology, 137:252-259 (2009).
Celma et al., "A Viral Nonstructural Protein Regulates Bluetongue Virus Trafficking and Release," Journal of Virology, 83:6806-6816 (2009).
Celma et al., "Interaction of Calpactin Light Chain (S100A10/p11) and a Viral NS Protein is Essential for Intracelleular Trafficking of Nonenveloped Bluetongue Virus," Journal of Virology, 85:4783-4791 (2011).
Han et al., "The NS3 Protein of Bluetongue Virus Exhibits Viroporin-like Properties," The Journal of Biological Chemistry, 279:43092-43097 (2004).
Huismans et al., "A Comparison of Different Orbivirus Proteins that Could Affect Virulence," Veterinaria Italiana, 40:417-425 (2004).
van Gennip et al., "Bluetongue Viruses Based on Modified-Live Vaccine Serotype 6 with Exchanged Outer Shell Proteins Confer Full Protection in Sheep Against Virulent BTV8," PLOS One, 7:1-11 (2012).
van Gennip et al., "Bluetongue Virus Nonstructural Protein NS3/NS3a is Not Essential for Virus Replication," PLOS One, 9:1-8 (2014).
van Niekerk et al., "Membrane Association of African Horsesickness Virus Nonstructural Protein NS3 Determines its Cytotoxicity," Virology, 279:499-508 (2001).
van Staden et al., "Characterization of Two African Horse Sickness Virus Nonstructural Proteins, NS1 and NS3," Archives of Virology, 14:251-258 (1998).
International Search Report dated Sep. 3, 2014 from corresponding PCT Application No. PCT/NL2014/050312.
Feenstra, F. et al., "RNA Elements in Open Reading Frames of the Bluetongue Virus Genome are Essential for Virus Replication", PLOS One. 2014, vol. 9, Issue 3, e92377.
Feenstra, F. et al., "Balance of RNA Sequence Requirement and NS3/NS3a Expression of Segment 10 of Orbiviruses", Journal of General Virology, 2016, vol. 97, pp. 411-421.

* cited by examiner

*Primary Examiner* — Shanon A. Foley
*Assistant Examiner* — Myron G Hill
(74) *Attorney, Agent, or Firm* — McDermott Will & Emery, LLP

(57) ABSTRACT

The invention relates to methods for producing a propagation-competent strain of a mutant Reoviridae virus, and to a propagation-competent strain of a mutant Reoviridae virus that is obtainable by a method of the invention. The invention further relates to a propagation-competent strain of a mutant Reoviridae virus, comprising a deletion of a genetic region that is relevant for propagation of the virus, and to a vaccine, comprising a propagation-competent strain of a mutant Reoviridae virus.

8 Claims, 19 Drawing Sheets

Fig. 2

Fig. 4A

*BTV Production in BSR cells*

Figure 1:
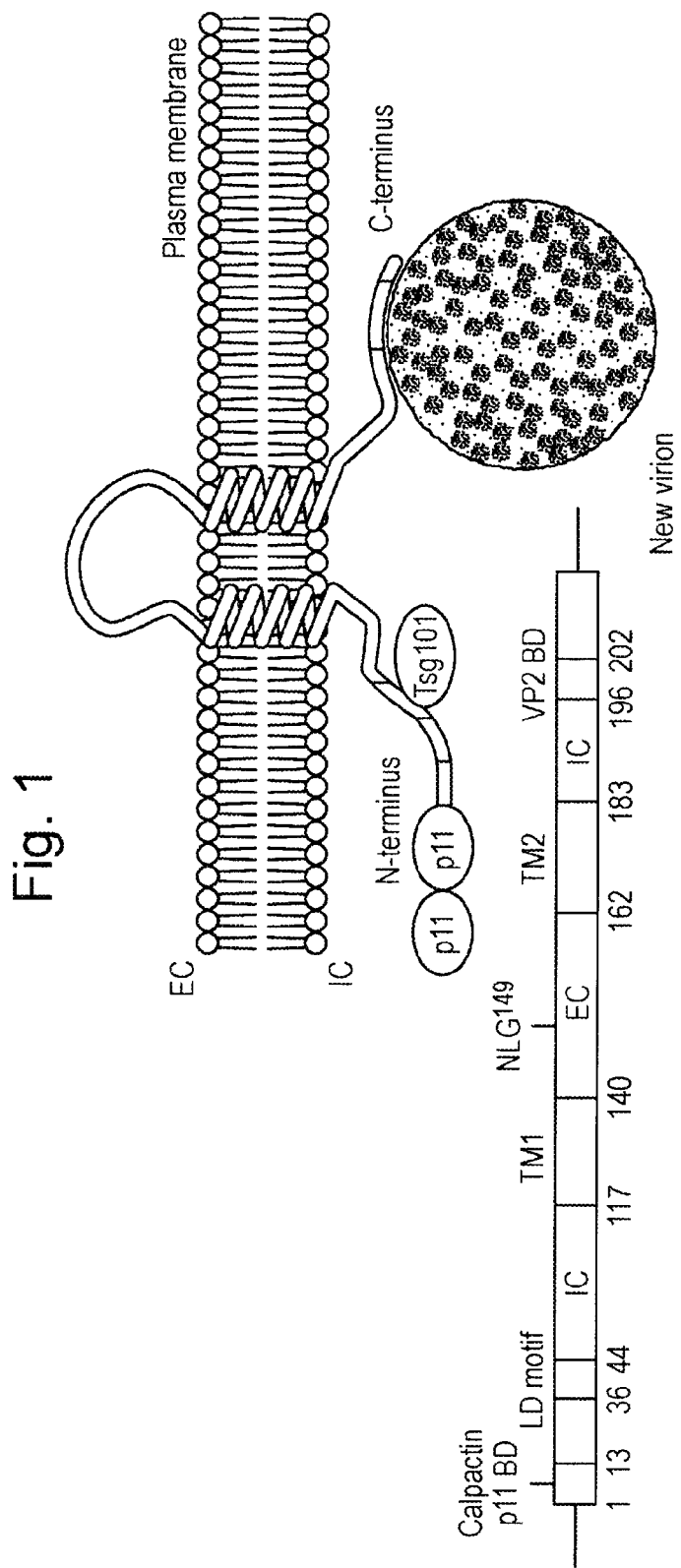

(Bar chart: Virus titer 10log TCID50/ml vs Hours post infection at 24, 48, 72, 144; bars for rgBTV1 and modBTvac-1)

Fig. 4B

*Detection of BTV by panBTV PCR tests*

(Bar chart: Detection limit (10log dilution) for rgBTV 1, BTV(S10-25), modBTvac-1; panBTV PCR (S1) values 6.5, 6.8, 6.7; panBTV PCR (S10) values 5.2, 5.3, 3.5)

Fig. 4C

*BTV release from cell lines*

(Bar chart: Relative virus release (%) vs Hours post infection at 24, 48, 72, 144; bars for rgBTV1 in BSR, rgBTV1 in KC, modBTvac-1 in BSR, modBTvac-1 in KC)

Fig. 5A

Daily rectal temperature

Legend:
- rgBTV1 6400 (filled square)
- rgBTV1 6401 (open square)
- modBTvac-1 6402 (filled triangle)
- modBTvac-1 6403 (open triangle)

X-axis: Days post infection
Y-axis: Temperature (°C)

Fig. 5B

Daily clinical score

Legend:
- rgBTV1 6400
- rgBTV1 6401
- modBTvac-1 6402
- modBTvac-1 6403

X-axis: Days post immunization
Y-axis: Clinical score

| VP7-ELISA | | 21 | 42 | 63 |
|---|---|---|---|---|
| rgBTV1 | 6400 | 32 | 64 | 128 |
| rgBTV1 | 6401 | <2 | 64 | 64 |
| modBTvac-1 | 6402 | 32 | 64 | 128 |
| modBTvac-1 | 6403 | 32 | 128 | 256 |
| BTV1-VNT | | 21 | 42 | 63 |
| rgBTV1 | 6400 | 64 | 64 | 64 |
| rgBTV1 | 6401 | <2 | 128 | 96 |
| modBTvac-1 | 6402 | <2 | 32 | 256 |
| modBTvac-1 | 6403 | 2 | 24 | 256 |

Fig. 7A

Daily mean body temperature

- BTV1 backbone, BTV8
- BTV6 backbone, BTV8
- BTV8 backbone, BTV8
- deadBTV8, BTV8
- Lysate, BTV8

Days post vaccination

Fig. 7C

Seg-1 panBTV PCR test

- BTV1 backbone, BTV8
- BTV6 backbone, BTV8
- BTV8 backbone, BTV8
- deadBTV8, BTV8
- Lysate, BTV8

Days post vaccination

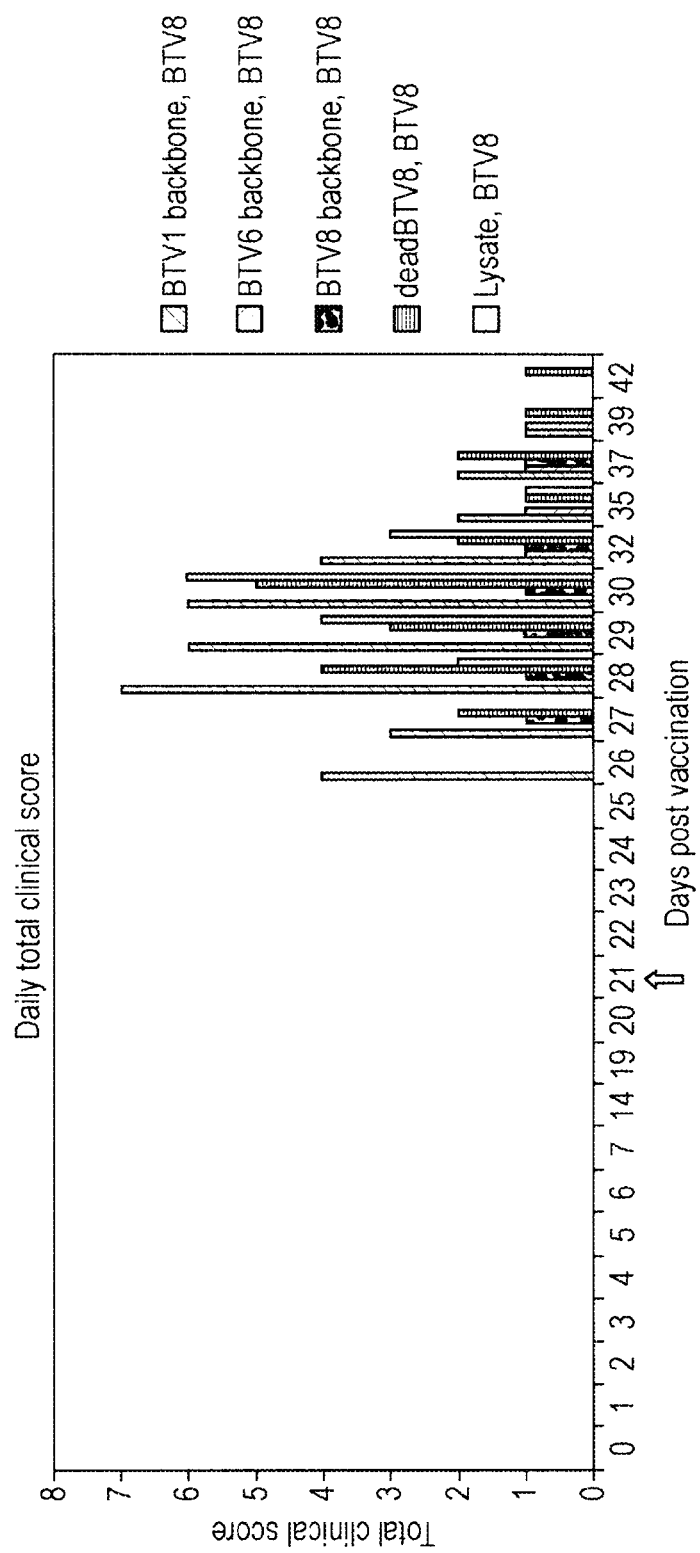

Fig. 7D

Seg-10 panBTV PCR test

- BTV1 backbone, BTV8
- BTV6 backbone, BTV8
- BTV8 backbone, BTV8
- deadBTV8, BTV8
- Lysate, BTV8

Days post vaccination

Fig. 7E

ID.VET cELISA

- BTV1 backbone, BTV8
- BTV6 backbone, BTV8
- BTV8 backbone, BTV8
- deadBTV8, BTV8
- Lysate, BTV8

Days post vaccination

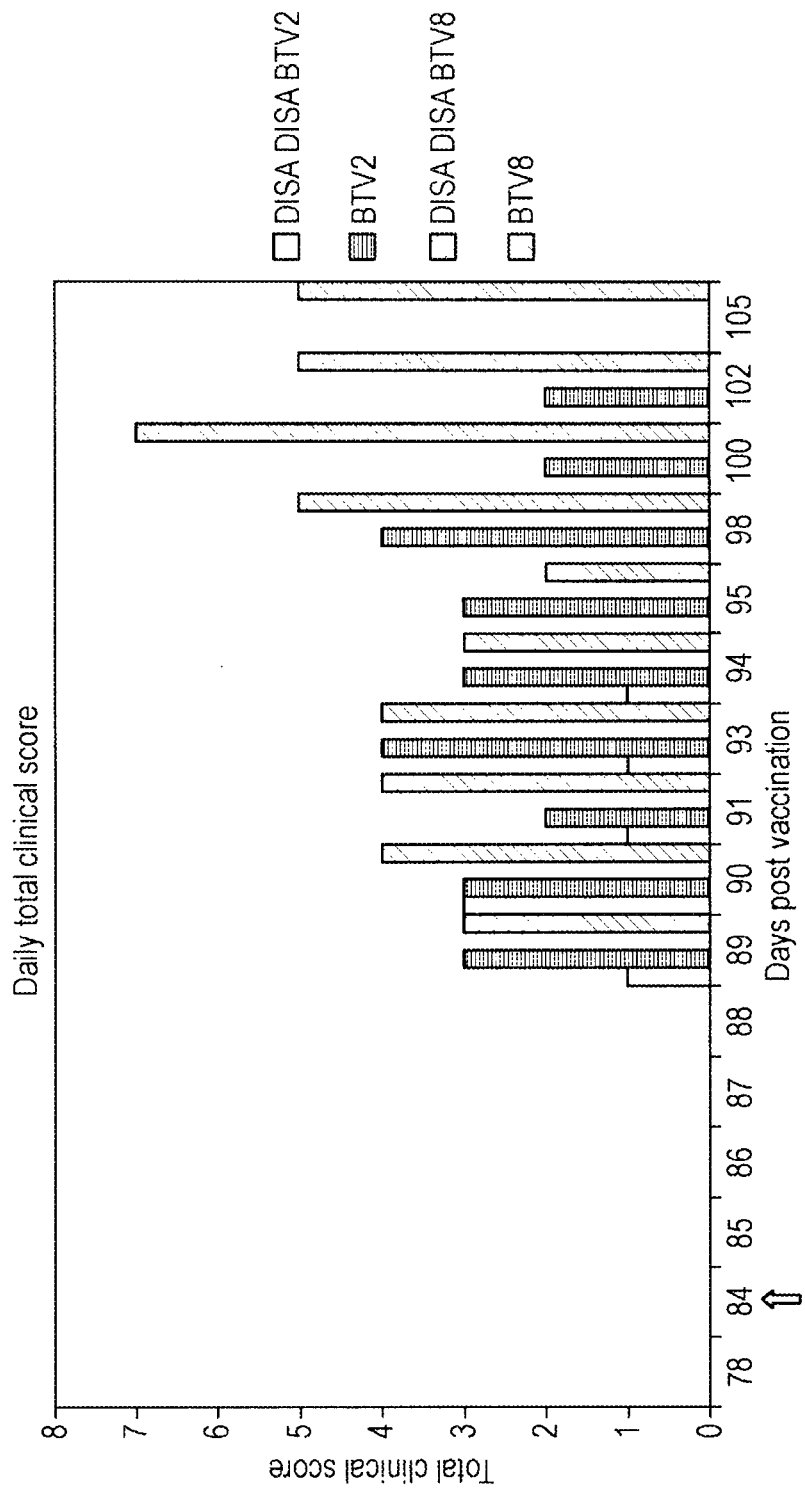

Fig. 9D

VP7 cELISA

DISA DISA BTV2
BTV2
DISA DISA BTV8
BTV8

Days post vaccination

Fig. 9E

Serum Neutralizing test (serotype 2)

☐ DISA DISA BTV2   ▦ BTV2   ☐ DISA DISA BTV8   ☐ BTV8

(BTV8)NS3ΔTM ~22.6 kDa

Denaturing conditions (400 ml)

M = marker
P = pellet
S = supernatant
FT = flow-through
W = wash
D = elution buffer D (pH 5.9)
E = elution buffer E (pH 4.5)
N = elution buffer native (250mM imidazole)
1-4 fractions 1 to 4

SEQUENCE LISTING

```
<160> NUMBER OF SEQ ID NOS: 97

<210> SEQ ID NO 1
<211> LENGTH: 22
<212> TYPE: DNA
<213> ORGANISM: Artificial Sequence
<220> FEATURE:
<223> OTHER INFORMATION: primer

<400> SEQUENCE: 1
ttaaaatgca atggtcgcaa tc                                            22

<210> SEQ ID NO 2
<211> LENGTH: 19
<212> TYPE: DNA
<213> ORGANISM: Artificial Sequence
<220> FEATURE:
<223> OTHER INFORMATION: primer

<400> SEQUENCE: 2
tccggatcaa gttcactcc                                                19

<210> SEQ ID NO 3
<211> LENGTH: 13
<212> TYPE: DNA
<213> ORGANISM: Artificial Sequence
<220> FEATURE:
<223> OTHER INFORMATION: primer
```

<400> SEQUENCE: 3
ccgtgcaagg tgc                                                      13

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
gttaaaaatc tatagagatg                                               20

<210> SEQ ID NO 5
<211> LENGTH: 19
<212> TYPE: DNA
<213> ORGANISM: Artificial Sequence
<220> FEATURE:
<223> OTHER INFORMATION: primer

<400> SEQUENCE: 5
gtaagtgtaa tctaagaga                                                19

<210> SEQ ID NO 6
<211> LENGTH: 21
<212> TYPE: DNA
<213> ORGANISM: Artificial Sequence
<220> FEATURE:
<223> OTHER INFORMATION: primer

<400> SEQUENCE: 6
gttaaaaaat cgttcaagat g                                             21

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
gtaagtttaa atcgcaagac g                                             21

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
agtgtcgctg ccatgctatc                                               20

<210> SEQ ID NO 9
<211> LENGTH: 18
<212> TYPE: DNA
<213> ORGANISM: Artificial Sequence
<220> FEATURE:
<223> OTHER INFORMATION: primer

<400> SEQUENCE: 9
gcgtacgatg cgaatgca                                                 18

<210> SEQ ID NO 10
<211> LENGTH: 22

-continued

<210> SEQ ID NO 10
<211> LENGTH: 22
<212> TYPE: DNA
<213> ORGANISM: Artificial Sequence
<220> FEATURE:
<223> OTHER INFORMATION: primer

<400> SEQUENCE: 10
cgaacctttg gatcagcccg ga                                              22

<210> SEQ ID NO 11
<211> LENGTH: 22
<212> TYPE: DNA
<213> ORGANISM: Artificial Sequence
<220> FEATURE:
<223> OTHER INFORMATION: primer

<400> SEQUENCE: 11
gttaaaaagt gtcgctgcca tg                                              22

<210> SEQ ID NO 12
<211> LENGTH: 22
<212> TYPE: DNA
<213> ORGANISM: Artificial Sequence
<220> FEATURE:
<223> OTHER INFORMATION: primer

<400> SEQUENCE: 12
gtaagtgtgt agtgtcgcgc ac                                              22

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
ttaggatgga accttacgc                                                  19

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
attctgcccc tctctaacca                                                 20

<210> SEQ ID NO 15
<211> LENGTH: 27
<212> TYPE: DNA
<213> ORGANISM: Artificial Sequence
<220> FEATURE:
<223> OTHER INFORMATION: primer

<400> SEQUENCE: 15
ctttgagtag gtattcgatc tcctgcg                                         27

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
cgcaatcttc ggatgtaagc                                               20

<210> SEQ ID NO 17
<211> LENGTH: 21
<212> TYPE: DNA
<213> ORGANISM: Artificial Sequence
<220> FEATURE:
<223> OTHER INFORMATION: primer

<400> SEQUENCE: 17
gcacactacc ttggatctct g                                             21

<210> SEQ ID NO 18
<211> LENGTH: 18
<212> TYPE: DNA
<213> ORGANISM: Artificial Sequence
<220> FEATURE:
<223> OTHER INFORMATION: primer

<400> SEQUENCE: 18
tcgccatcct catcatcg                                                 18

<210> SEQ ID NO 19
<211> LENGTH: 25
<212> TYPE: DNA
<213> ORGANISM: Artificial Sequence
<220> FEATURE:
<223> OTHER INFORMATION: primer

<400> SEQUENCE: 19
ttgttgaaag tacgagacac aagag                                         25

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
gtatcagcct tctttgaatc gatt                                          24

<210> SEQ ID NO 21
<211> LENGTH: 22
<212> TYPE: DNA
<213> ORGANISM: Artificial Sequence
<220> FEATURE:
<223> OTHER INFORMATION: primer

<400> SEQUENCE: 21
catccactgc acccactggt ca                                            22

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
aggaacagtc ggcttatcac                                               20

<210> SEQ ID NO 23
<211> LENGTH: 21
<212> TYPE: DNA
<213> ORGANISM: Artificial Sequence

```
<220> FEATURE:
<223> OTHER INFORMATION: primer

<400> SEQUENCE: 23
ttcgctaatg tgcttctcca t                                              21

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
ttgtcagctt tacgcaaacc ccg                                            23

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
cggagacagc gcagtatgta                                                20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
cctcggtagt atccctcacg                                                20

<210> SEQ ID NO 27
<211> LENGTH: 26
<212> TYPE: DNA
<213> ORGANISM: Artificial Sequence
<220> FEATURE:
<223> OTHER INFORMATION: primer

<400> SEQUENCE: 27
acatacgatg ccytcggagg attctg                                         26

<210> SEQ ID NO 28
<211> LENGTH: 27
<212> TYPE: DNA
<213> ORGANISM: Bluetongue virus 10
<220> FEATURE:
<221> NAME/KEY: CDS
<222> LOCATION: (1)..(27)

<400> SEQUENCE: 28 cca cca agg tat gct ccg agt gca ccg                                  27
Pro Pro Arg Tyr Ala Pro Ser Ala Pro
1               5

<210> SEQ ID NO 29
<211> LENGTH: 9
<212> TYPE: PRT
<213> ORGANISM: Bluetongue virus 10

<400> SEQUENCE: 29

Pro Pro Arg Tyr Ala Pro Ser Ala Pro
```

-continued

```
1               5

<210> SEQ ID NO 30
<211> LENGTH: 27
<212> TYPE: DNA
<213> ORGANISM: Artificial Sequence
<220> FEATURE:
<223> OTHER INFORMATION: mutant NS3-ASAP
<220> FEATURE:
<221> NAME/KEY: CDS
<222> LOCATION: (1)..(27)
<223> OTHER INFORMATION: NS3-ASAP

<400> SEQUENCE: 30 cca cca agg tat gct gca agt gca ccg                                    27
Pro Pro Arg Tyr Ala Ala Ser Ala Pro
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Construct

<400> SEQUENCE: 31

Pro Pro Arg Tyr Ala Ala Ser Ala Pro
1               5

<210> SEQ ID NO 32
<211> LENGTH: 27
<212> TYPE: DNA
<213> ORGANISM: Artificial Sequence
<220> FEATURE:
<223> OTHER INFORMATION: mutant NS3-GAAP
<220> FEATURE:
<221> NAME/KEY: CDS
<222> LOCATION: (1)..(27)
<223> OTHER INFORMATION: NS3-GAAP

<400> SEQUENCE: 32 cca cca agg tat gct gga gca gca ccg                                    27
Pro Pro Arg Tyr Ala Gly Ala Ala Pro
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Construct

<400> SEQUENCE: 33

Pro Pro Arg Tyr Ala Gly Ala Ala Pro
1               5

<210> SEQ ID NO 34
<211> LENGTH: 21
<212> TYPE: DNA
<213> ORGANISM: Bluetongue virus 10
<220> FEATURE:
<221> NAME/KEY: CDS
<222> LOCATION: (1)..(21)

<400> SEQUENCE: 34 gct gca ttc gca tcg tac gcg                                            21
Ala Ala Phe Ala Ser Tyr Ala
1               5
```

<210> SEQ ID NO 35
<211> LENGTH: 7
<212> TYPE: PRT
<213> ORGANISM: Bluetongue virus 10

<400> SEQUENCE: 35

Ala Ala Phe Ala Ser Tyr Ala
1 5

<210> SEQ ID NO 36
<211> LENGTH: 21
<212> TYPE: DNA
<213> ORGANISM: Artificial Sequence
<220> FEATURE:
<223> OTHER INFORMATION: Mutant B

<400> SEQUENCE: 36
gcagcttttg ctagctatgc g 21

<210> SEQ ID NO 37
<211> LENGTH: 24
<212> TYPE: DNA
<213> ORGANISM: Bluetongue virus 10
<220> FEATURE:
<221> NAME/KEY: CDS
<222> LOCATION: (1)..(24)

<400> SEQUENCE: 37 gtg gtt gcg ctg ttg aca tca gtt 24
Val Val Ala Leu Leu Thr Ser Val
1 5

<210> SEQ ID NO 38
<211> LENGTH: 8
<212> TYPE: PRT
<213> ORGANISM: Bluetongue virus 10

<400> SEQUENCE: 38

Val Val Ala Leu Leu Thr Ser Val
1 5

<210> SEQ ID NO 39
<211> LENGTH: 24
<212> TYPE: DNA
<213> ORGANISM: Artificial Sequence
<220> FEATURE:
<223> OTHER INFORMATION: Mutant TM1 ALL->EEE
<220> FEATURE:
<221> NAME/KEY: CDS
<222> LOCATION: (1)..(24)
<223> OTHER INFORMATION: ALL->EEE

<400> SEQUENCE: 39 gtg gtt gaa gag gaa aca tca gtt 24
Val Val Glu Glu Glu Thr Ser Val
1 5

<210> SEQ ID NO 40
<211> LENGTH: 8
<212> TYPE: PRT
<213> ORGANISM: Artificial Sequence
<220> FEATURE:
<223> OTHER INFORMATION: Synthetic Construct

<400> SEQUENCE: 40

Val Val Glu Glu Glu Thr Ser Val
1 5

```
<210> SEQ ID NO 41
<211> LENGTH: 8
<212> TYPE: PRT
<213> ORGANISM: Artificial Sequence
<220> FEATURE:
<223> OTHER INFORMATION: sequence for transmembrane region (TM1)

<400> SEQUENCE: 41

Val Val Asp Asp Asp Thr Ser Val
1               5

<210> SEQ ID NO 42
<211> LENGTH: 18
<212> TYPE: DNA
<213> ORGANISM: Bluetongue virus 10
<220> FEATURE:
<221> NAME/KEY: CDS
<222> LOCATION: (1)..(18)

<400> SEQUENCE: 42 aag ata aat gga act aaa                                           18
Lys Ile Asn Gly Thr Lys
1               5

<210> SEQ ID NO 43
<211> LENGTH: 6
<212> TYPE: PRT
<213> ORGANISM: Bluetongue virus 10

<400> SEQUENCE: 43

Lys Ile Asn Gly Thr Lys
1               5

<210> SEQ ID NO 44
<211> LENGTH: 18
<212> TYPE: DNA
<213> ORGANISM: Artificial Sequence
<220> FEATURE:
<223> OTHER INFORMATION: Mutant NS3-N149S
<220> FEATURE:
<221> NAME/KEY: CDS
<222> LOCATION: (1)..(18)
<223> OTHER INFORMATION: NS3-N149S

<400> SEQUENCE: 44 aag ata tcg gga act aaa                                           18
Lys Ile Ser Gly Thr Lys
1               5

<210> SEQ ID NO 45
<211> LENGTH: 6
<212> TYPE: PRT
<213> ORGANISM: Artificial Sequence
<220> FEATURE:
<223> OTHER INFORMATION: Synthetic Construct

<400> SEQUENCE: 45

Lys Ile Ser Gly Thr Lys
1               5

<210> SEQ ID NO 46
<211> LENGTH: 21
<212> TYPE: DNA
<213> ORGANISM: Bluetongue virus 10
<220> FEATURE:
<221> NAME/KEY: CDS
<222> LOCATION: (1)..(21)
```

<400> SEQUENCE: 46 gtg agg atg agt ttt acg gag                                       21
Val Arg Met Ser Phe Thr Glu
1               5

<210> SEQ ID NO 47
<211> LENGTH: 7
<212> TYPE: PRT
<213> ORGANISM: Bluetongue virus 10

<400> SEQUENCE: 47

Val Arg Met Ser Phe Thr Glu
1               5

<210> SEQ ID NO 48
<211> LENGTH: 7
<212> TYPE: PRT
<213> ORGANISM: Artificial Sequence
<220> FEATURE:
<223> OTHER INFORMATION: Bluetongue virus 10 sequence for C-terminal
      Stop

<400> SEQUENCE: 48

Val Arg Met Arg Phe Thr Asp
1               5

<210> SEQ ID NO 49
<211> LENGTH: 21
<212> TYPE: DNA
<213> ORGANISM: Artificial Sequence
<220> FEATURE:
<223> OTHER INFORMATION: Mutant CT4stop 212
<220> FEATURE:
<221> NAME/KEY: CDS
<222> LOCATION: (1)..(21)
<223> OTHER INFORMATION: CT4stop 212

<400> SEQUENCE: 49 gtg agg atg tga ttt acg gag                                       21
Val Arg Met     Phe Thr Glu
1               5

<210> SEQ ID NO 50
<211> LENGTH: 59
<212> TYPE: DNA
<213> ORGANISM: Bluetongue virus 10
<220> FEATURE:
<221> NAME/KEY: CDS
<222> LOCATION: (1)..(57)

<400> SEQUENCE: 50 cca cca agg tat gct ccg agt gca ccg atg cca tca tct atg cca acg   48
Pro Pro Arg Tyr Ala Pro Ser Ala Pro Met Pro Ser Ser Met Pro Thr
1               5                   10                  15 gtt gcc ctt ga                                                    59
Val Ala Leu <210> SEQ ID NO 51
<211> LENGTH: 19
<212> TYPE: PRT
<213> ORGANISM: Bluetongue virus 10

<400> SEQUENCE: 51

Pro Pro Arg Tyr Ala Pro Ser Ala Pro Met Pro Ser Ser Met Pro Thr
1               5                   10                  15

<210> SEQ ID NO 52
<211> LENGTH: 20
<212> TYPE: PRT
<213> ORGANISM: Bluetongue virus 10

<400> SEQUENCE: 52

Pro Pro Arg Tyr Ala Pro Ser Ala Pro Met Pro Ser Ser Met Pro Thr
1               5                   10                  15

Val Ala Leu Glu
            20

<210> SEQ ID NO 53
<211> LENGTH: 63
<212> TYPE: DNA
<213> ORGANISM: Artificial Sequence
<220> FEATURE:
<223> OTHER INFORMATION: Mutant StyI filled
<220> FEATURE:
<221> NAME/KEY: CDS
<222> LOCATION: (1)..(63)

<400> SEQUENCE: 53 cca cca agc aag gta tgc tcc gag tgc acc gat gcc atc atc tat gcc      48
Pro Pro Ser Lys Val Cys Ser Glu Cys Thr Asp Ala Ile Ile Tyr Ala
1               5                   10                  15 aac ggt tgc cct tga                                                  63
Asn Gly Cys Pro
            20

<210> SEQ ID NO 54
<211> LENGTH: 20
<212> TYPE: PRT
<213> ORGANISM: Artificial Sequence
<220> FEATURE:
<223> OTHER INFORMATION: Synthetic Construct

<400> SEQUENCE: 54

Pro Pro Ser Lys Val Cys Ser Glu Cys Thr Asp Ala Ile Ile Tyr Ala
1               5                   10                  15

Asn Gly Cys Pro
            20

<210> SEQ ID NO 55
<211> LENGTH: 36
<212> TYPE: DNA
<213> ORGANISM: Artificial Sequence
<220> FEATURE:
<223> OTHER INFORMATION: Mutant S-rev-1
<220> FEATURE:
<221> NAME/KEY: CDS
<222> LOCATION: (1)..(36)

<400> SEQUENCE: 55 cca cca gca agg tat gct ccg agt gca ccg atg cca                      36
Pro Pro Ala Arg Tyr Ala Pro Ser Ala Pro Met Pro
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic Construct

<400> SEQUENCE: 56

```
Pro Pro Ala Arg Tyr Ala Pro Ser Ala Pro Met Pro
1               5                   10
```

<210> SEQ ID NO 57
<211> LENGTH: 36
<212> TYPE: DNA
<213> ORGANISM: Artificial Sequence
<220> FEATURE:
<223> OTHER INFORMATION: Mutant S-rev-2
<220> FEATURE:
<221> NAME/KEY: CDS
<222> LOCATION: (1)..(36)

<400> SEQUENCE: 57

```
cac caa gca agg tat gct ccg agt gca ccg atg cca                    36
His Gln Ala Arg Tyr Ala Pro Ser Ala Pro Met Pro
1               5                   10
```

<210> SEQ ID NO 58
<211> LENGTH: 12
<212> TYPE: PRT
<213> ORGANISM: Artificial Sequence
<220> FEATURE:
<223> OTHER INFORMATION: Synthetic Construct

<400> SEQUENCE: 58

```
His Gln Ala Arg Tyr Ala Pro Ser Ala Pro Met Pro
1               5                   10
```

<210> SEQ ID NO 59
<211> LENGTH: 38
<212> TYPE: DNA
<213> ORGANISM: Bluetongue virus 10

```
<221> NAME/KEY: CDS
<222> LOCATION: (1)..(42)

<400> SEQUENCE: 62 aag gct gca ttc gca tcg tac gta cgc gga agc gtt tcg tga         42
Lys Ala Ala Phe Ala Ser Tyr Val Arg Gly Ser Val Ser
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Synthetic Construct

<400> SEQUENCE: 63

Lys Ala Ala Phe Ala Ser Tyr Val Arg Gly Ser Val Ser
1               5                   10

<210> SEQ ID NO 64
<211> LENGTH: 41
<212> TYPE: DNA
<213> ORGANISM: Artificial Sequence
<220> FEATURE:
<223> OTHER INFORMATION: mutant B-rev-1
<220> FEATURE:
<221> NAME/KEY: CDS
<222> LOCATION: (1)..(39)

<400> SEQUENCE: 64 aag gct gca ttc gca tcg tac gta gcg gaa gcg ttt cgt ga          41
Lys Ala Ala Phe Ala Ser Tyr Val Ala Glu Ala Phe Arg
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Synthetic Construct

<400> SEQUENCE: 65

Lys Ala Ala Phe Ala Ser Tyr Val Ala Glu Ala Phe Arg
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Mutant B-rev-1

<400> SEQUENCE: 66

Lys Ala Ala Phe Ala Ser Tyr Val Ala Glu Ala Phe Arg Asp
1               5                   10

<210> SEQ ID NO 67
<211> LENGTH: 61
<212> TYPE: DNA
<213> ORGANISM: Bluetongue virus 10
<220> FEATURE:
<221> NAME/KEY: CDS
<222> LOCATION: (20)..(61)

<400> SEQUENCE: 67
gttaaaaagt gtcgctgcc atg cta tcc ggg ctg atc caa agg ttc gaa gaa    52
                    Met Leu Ser Gly Leu Ile Gln Arg Phe Glu Glu
                    1               5                   10
```

```
gaa aaa atg                                                          61
Glu Lys Met

<210> SEQ ID NO 68
<211> LENGTH: 14
<212> TYPE

Met Leu Ser Gly Leu Ile Gln Arg Phe Glu Glu Glu Lys Ala
1               5                   10

<210> SEQ ID NO 73
<211> LENGTH: 61
<212> TYPE: DNA
<213> ORGANISM: Artificial Sequence
<220> FEATURE:
<223> OTHER INFORMATION: Mutant AUG1+2
<220> FEATURE:
<221> NAME/KEY: CDS
<222> LOCATION: (20)..(61)
<223> OTHER INFORMATION: AUG1+2

<400> SEQUENCE: 73
gttaaaaagt gtcgctgcc gcc cta tcc ggg ctg atc caa agg ttc gaa gaa        52
                    Ala Leu Ser Gly Leu Ile Gln Arg Phe Glu Glu
                     1               5                   10 gaa aaa gcc                                                              61
Glu Lys Ala <210> SEQ ID NO 74
<211> LENGTH: 14
<212> TYPE: PRT
<213> ORGANISM: Artificial Sequence
<220> FEATURE:
<223> OTHER INFORMATION: Synthetic Construct

<400> SEQUENCE: 74

Ala Leu Ser Gly Leu Ile Gln Arg Phe Glu Glu Glu Lys Ala
1               5                   10

<210> SEQ ID NO 75
<211> LENGTH: 61
<212> TYPE: DNA
<213> ORGANISM: Artificial Sequence
<220> FEATURE:
<223> OTHER INFORMATION: Mutant-A
<220> FEATURE:
<221> NAME/KEY: CDS
<222> LOCATION: (20)..(61)
<223> OTHER INFORMATION: Mutant A

<400> SEQUENCE: 75
gttaaaaagt gtcgctgcc atg cta tcg ggc tta ata cag aga ttt gaa gaa        52
                    Met Leu Ser Gly Leu Ile Gln Arg Phe Glu Glu
                     1               5                   10 gaa aaa atg                                                              61
Glu Lys Met <210> SEQ ID NO 76
<211> LENGTH: 14
<212> TYPE: PRT
<213> ORGANISM: Artificial Sequence
<220> FEATURE:
<223> OTHER INFORMATION: Synthetic Construct

<400> SEQUENCE: 76

Met Leu Ser Gly Leu Ile Gln Arg Phe Glu Glu Glu Lys Met
1               5                   10

<210> SEQ ID NO 77
<211> LENGTH: 22
<212> TYPE: DNA
<213> ORGANISM: Artificial Sequence
<220> FEATURE:
<223> OTHER INFORMATION: Mutant Deletion

<400> SEQUENCE: 77

```
gttaaaaagt gtcgctgcca tg                                              22
```

<210> SEQ ID NO 78
<211> LENGTH: 822
<212> TYPE: DNA
<213> ORGANISM: Bluetongue virus 10

<400> SEQUENCE: 78

```
gttaaaaagt gtcgctgcca tgctatccgg gctgatccaa aggttcgaag aagaaaaaat    60
gaaacataat caagacagag ttgaagagct gagtctagta cgtgtagatg acaccatctc   120
tcaaccacca aggtatgctc cgagtgcacc gatgccatca tctatgccaa cggttgccct   180
tgaaatattg gacaaagcga tgtcaaacac aactggtgca acgcaaacac aaaaggcgga   240
gaaggctgca ttcgcatcgt acgcggaagc gtttcgtgat gatgtaagac tgagacagat   300
caagcgccat gtgaacgagc agattttacc aaaattaaaa agtgatctaa gtggattgaa   360
gaagaaacga gcaatcatac acactactct attagtagcg gctgtggttg cgctgttgac   420
atcagtttgt acccttttcaa gcgatatgag tgtggccttt aagataaatg gaactaaaac   480
agaagtgcct tcatggttta aaagccttaa cccgatgctt ggcgtggtca atttgggagc   540
aactttctg atgatggttt gcgcaaagag tgaaagagcc ttgaaccagc agatagatat   600
gataaagaag gaagtgatga agaaacaatc ttataatgat gcggtgagga tgagttttac   660
agagttctcg tcagtcccgc tggatggttt cgaaatgcca ttaacctgag gacagtaggt   720
agagtggcgc cccgaggttt acgtcgtgca gggtggttga cctcgcggcg tagactccca   780
ctgctgtata acgggggagg gtgcgcgaca ctacacactt ac                      822
```

<210> SEQ ID NO 79
<211> LENGTH: 451
<212> TYPE: DNA
<213> ORGANISM: Artificial Sequence
<220> FEATURE:
<223> OTHER INFORMATION: Mutant BPdel

<400> SEQUENCE: 79

```
gttaaaaagt gtcgctgcca tgctatccgg gctgatccaa aggttcgaag aagaaaaaat    60
gaaacataat caagacagag ttgaagagct gagtctagta cgtgtagatg acaccatctc   120
tcaaccacca aggtatgctc cgagtgcacc gatgccatca tctatgccaa cggttgccct   180
tgaaatattg gacaaagcga tgtcaaacac aactggtgca acgcaaacac aaaaggcgga   240
gaaggctgca ttcgcatcgt actaatgatg cggtgaggat gagttttaca gagttctcgt   300
cagtcccgct ggatggtttc gaaatgccat taacctgagg acagtaggta gagtggcgcc   360
ccgaggttta cgtcgtgcag ggtggttgac ctcgcggcgt agactcccac tgctgtataa   420
cgggggaggg tgcgcgacac tacacactta c                                  451
```

<210> SEQ ID NO 80
<211> LENGTH: 738
<212> TYPE: DNA
<213> ORGANISM: Artificial Sequence
<220> FEATURE:
<223> OTHER INFORMATION: BPS1 revertant

<400> SEQUENCE: 80

```
gttaaaaagt gtcgctgcca tgctatccgg gctgatccaa aggttcgaag aagaaaaaat    60
```

| | |
|---|---:|
| gaaacataat caagacagag ttgaagagct gagtctagta cgtgtagatg acaccatctc | 120 |
| tcaaccacca aggtatgctc cgagtgcacc gatgccatca tctatgccaa cggttgccct | 180 |
| tgaaatattg gacttgatcc ggaggaagag ttcttacgta attatagagt ttcaagggag | 240 |
| atgactgaag tggaaaaatt tatcgaattc cgtgctaaaa acgagatgca aatatacgga | 300 |
| gatataccca ttaaggtatg gtgttgtttc atcaatgaac tgagtgcgga attaaaacat | 360 |
| attcccttag ggatgcaagt tatggctgac tttgtaaacc gtttcgattc accattccat | 420 |
| caggggaata gagatttatc aaatcttgaa gattttcaag ttgcatacac tacgccgctt | 480 |
| ttgtttgaaa tgtgttgcat ggaatcaatt ttagaattca atatcaaaat gcgtatgcgt | 540 |
| gaagaagata tctcggcgct ggaattcggt gattacagag ttctcgtcag tcccgctgga | 600 |
| tggtttcgaa atgccattaa cctgaggaca gtaggtagag tggcgccccg aggtttacgt | 660 |
| cgtgcagggt ggttgacctc gcggcgtaga ctcccactgc tgtataacgg gggagggtgc | 720 |
| gcgacactac acacttac | 738 |

<210> SEQ ID NO 81
<211> LENGTH: 794
<212> TYPE: DNA
<213> ORGANISM: Artificial Sequence
<220> FEATURE:
<223> OTHER INFORMATION: BPS1 revertant

<400> SEQUENCE: 81

| | |
|---|---:|
| gttaaaaagt gtcgctgcca tgctatccgg gctgatccaa aggttcgaag aagaaaaaat | 60 |
| gaaacataat caagacagag ttgaagagct gagtctcacc attccatcag gggaatagag | 120 |
| atttatcaaa tcttgaagat tttcaagttg catacactac gccgcttttg tttgaaatgt | 180 |
| gttgcatgga atcaattta gaattcaata tcaaaatgcg tatgcgtgaa gaagatatct | 240 |
| cggcgctgga attcggtgat atgaaagttg atccggttgg actattgcgt gagttttca | 300 |
| ttctgtgctt accacaccca aagaagatta acaacgttct aagagcacca tactcttggt | 360 |
| ttgtaaagat gtggggcgtc ggagctgatc cgatcgttgt tttacaatct acggcaggcg | 420 |
| atgcaggaa ttcaaaggaa gtacgtgtag atgacaccat ctctcaacca ccaaggtatg | 480 |
| ctccgagtgc accgatgcca tcatctatgc caacggttgc ccttgaaata ttggacaaag | 540 |
| cgatgtcaaa cacaactggt gcaacgcaaa cacaaaaggc ggagaaggct gcattcgcat | 600 |
| cgtactaatg atgcggtgag gatgagtttt acagagttct cgtcagtccc gctggatggt | 660 |
| ttcgaaatgc cattaacctg aggacagtag gtagagtggc gccccgaggt ttacgtcgtg | 720 |
| cagggtggtt gacctcgcgg cgtagactcc cactgctgta taacggggga gggtgcgcga | 780 |
| cactacacac ttac | 794 |

<210> SEQ ID NO 82
<211> LENGTH: 519
<212> TYPE: DNA
<213> ORGANISM: Artificial Sequence
<220> FEATURE:
<223> OTHER INFORMATION: BPS2 revertant

<400> SEQUENCE: 82

| | |
|---|---:|
| gttaaaaagt gtcgctgcca tgctatccgg gctgatccaa aggttcgaag aagaaaaaat | 60 |
| tagagatgat attgcgagct tggatgagat atgtaatagg tggatacaga gtaggcacga | 120 |
| ccccggatga aacataatca agacagagtt gaagagctga gtctagtacg tgtagatgac | 180 |
| accatctctc aaccaccaag gtatgctccg agtgcaccga tgccatcatc tatgccaacg | 240 |

| | |
|---|---|
| gttgcccttg aaatattgga caaagcgatg tcaaacacaa ctggtgcaac gcaaacacaa | 300 |
| aaggcggaga aggctgcatt cgcatcgtac taatgatgcg gtgaggatga gttttacaga | 360 |
| gttctcgtca gtcccgctgg atggtttcga aatgccatta acctgaggac agtaggtaga | 420 |
| gtggcgcccc gaggtttacg tcgtgcaggg tggttgacct cgcggcgtag actcccactg | 480 |
| ctgtataacg ggggagggtg cgcgacacta cacacttac | 519 |

<210> SEQ ID NO 83
<211> LENGTH: 319
<212> TYPE: DNA
<213> ORGANISM: Artificial Sequence
<220> FEATURE:
<223> OTHER INFORMATION: BPS2del revertant

<400> SEQUENCE: 83

| | |
|---|---|
| gttaaaaagt gtcgctgcca tgctatccgg gctgatccaa aggttcgaag aagaaaaaat | 60 |
| tagagatgat attgcgagct tggatgagat atgtaatagg tggatacaga gtaggcacga | 120 |
| ccccgccatg taatgatgcg gtgaggatga gttttacaga gttctcgtca gtcccgctgg | 180 |
| atggtttcga aatgccatta acctgaggac agtaggtaga gtggcgcccc gaggtttacg | 240 |
| tcgtgcaggg tggttgacct cgcggcgtag actcccactg ctgtataacg ggggagggtg | 300 |
| cgcgacacta cacacttac | 319 |

<210> SEQ ID NO 84
<211> LENGTH: 822
<212> TYPE: DNA
<213> ORGANISM: Artificial Sequence
<220> FEATURE:
<223> OTHER INFORMATION: BTV8 Seg-10 of 'AUG3 tm 13'

<400> SEQUENCE: 84

| | |
|---|---|
| gttaaaaagt gtcgctgcca tgctatccgg gctgatccaa aggttcgaag aagaaaaaat | 60 |
| gaaacataat caagacagag ttgaagagct gagtctagta cgtgtagatg acaccatctc | 120 |
| tcaaccacca aggtatgctc cgagtgcacc ggccccatca tctgcccaa cggttgccct | 180 |
| tgaaatattg gacaaagcgg cctcaaacac aactggtgca acgcaaacac aaaaggcgga | 240 |
| gaaggctgca ttcgcatcgt acgcggaagc gtttcgtgat gatgtaagac tgagacagat | 300 |
| caagcgccat gtgaacgagc agattttacc aaaattaaaa agtgatctaa gtggattgaa | 360 |
| gaagaaacga gcaatcatac acactactct attagtagcg gctgtggttg cgctgttgac | 420 |
| atcagtttgt acccttttcaa gcgatgccag tgtggccttt aagataaatg gaactaaaac | 480 |
| agaagtgcct tcatggttta aaagccttaa cccggccctt ggcgtggtca atttgggagc | 540 |
| aacttttctg gccgccgttt gcgcaaagag tgaaagagcc ttgaaccagc agatagatgc | 600 |
| cataaagaag gaagtggcca agaaacaatc ttataatgat gcggtgaggg ccagttttac | 660 |
| agagttctcg tcagtcccgc tggatggttt cgaagcccca ttaacctgag gacagtaggt | 720 |
| agagtggcgc cccgaggttt acgtcgtgca gggtggttga cctcgcggcg tagactccca | 780 |
| ctgctgtata acggggagg gtgcgcgaca ctacacactt ac | 822 |

<210> SEQ ID NO 85
<211> LENGTH: 822
<212> TYPE: DNA
<213> ORGANISM: Artificial Sequence
<220> FEATURE:
<223> OTHER INFORMATION: BTV8 Seg-10 of 'AUG total'

<400> SEQUENCE: 85

```
gttaaaaagt gtcgctgccg ccctatccgg gctgatccaa aggttcgaag aagaaaaagc    60
caaacataat caagacagag ttgaagagct gagtctagta cgtgtagatg acaccatctc   120
tcaaccacca aggtatgctc cgagtgcacc ggccccatca tctgcccaa cggttgccct   180
tgaaatattg gacaaagcgg cctcaaacac aactggtgca acgcaaacac aaaaggcgga   240
gaaggctgca ttcgcatcgt acgcggaagc gtttcgtgat gatgtaagac tgagacagat   300
caagcgccat gtgaacgagc agattttacc aaaattaaaa agtgatctaa gtggattgaa   360
gaagaaacga gcaatcatac acactactct attagtagcg gctgtggttg cgctgttgac   420
atcagtttgt acccttcaa gcgatgccag tgtggccttt aagataaatg gaactaaaac   480
agaagtgcct tcatggttta aaagccttaa cccggcccct ggcgtggtca atttgggagc   540
aactttctg gccgccgttt gcgcaaagag tgaaagagcc ttgaaccagc agatagatgc   600
cataaagaag gaagtggcca agaaacaatc ttataatgat gcggtgaggg ccagttttac   660
agagttctcg tcagtcccgc tggatggttt cgaagcccca ttaacctgag gacagtaggt   720
agagtggcgc cccgaggttt acgtcgtgca gggtggttga cctcgcggcg tagactccca   780
ctgctgtata acgggggagg gtgcgcgaca ctacacactt ac                       822
```

<210> SEQ ID NO 86
<211> LENGTH: 840
<212> TYPE: DNA
<213> ORGANISM: Artificial Sequence
<220> FEATURE:
<223> OTHER INFORMATION: *A)BTV8 Seg-10 of 'NS3b His-tag'

<400> SEQUENCE: 86
gttaaaaagt gtcgctgccg ccctatccgg gctgatccaa aggttcgaag aagaaaaagc 60
caaacataat caagacagag ttgaagagct gagtctagta cgtgtagatg acaccatcta 120
gcaaccacca aggtatgtag taggtgcacc gatgccatca tcgatgccaa cggttgccct 180
tgaaatattg gacaaagcga tgtcaaacac aactggtgca acgcaaacac aaaaggcgga 240
gaaggctgca ttcgcatcgt acgcggaagc gtttcgtgat gatgtaagac tgagacagat 300
caagcgccat gtgaacgagc agattttacc aaaattaaaa agtgatctaa gtggattgaa 360
gaagaaacga gcaatcatac acactactct attagtagcg gctgtggttg cgctgttgac 420
atcagtttgt accctttcaa gcgatatgag tgtggccttt aagataaatg gaactaaaac 480
agaagtgcct tcatggttta aaagccttaa cccgatgctt ggcgtggtca atttgggagc 540
aacttttctg atgatggttt gcgcaaagag tgaaagagcc ttgaaccagc agatagatat 600
gataaagaag gaagtgatga agaaacaatc ttataatgat gcggtgagga tgagttttac 660
agagttctcg tcagtcccgc tggatggttt cgaaatgcca ttaacccatc atcaccatca 720
ccactgagga cagtaggtag agtggcgccc cgaggtttac gtcgtgcagg gtggttgacc 780
tcgcggcgta gactcccact gctgtataac gggggagggt gcgcgacact acacacttac 840

<210> SEQ ID NO 87
<211> LENGTH: 822
<212> TYPE: DNA
<213> ORGANISM: Artificial Sequence
<220> FEATURE:
<223> OTHER INFORMATION: *B) BTV6 Seg-10 of 'AUG total DIVA'

<400> SEQUENCE: 87
gttaaaaagt gtcgctgccg ccctatccgg gctgatccaa aggttcgaag aagaaagggc 60

```
caaacacaat caagatagag ttgaagagct gagtctagtg cgtgtagatg ataccatttc    120
tcaaccacca aggtatgccc cgagtgcgcc ggccccatca tctgcccaa cggttgccct     180 tgaaatattg acaaggcgg cctcaaacac aactggtgca acgcaaacac agaaagcgga    240
gaaggcagct tttgctagct atgcggaagc gtttcgtgat gatgtgagat tgagacagat    300
caaacgccat gtgaacgagc agattttacc aaaattaaaa agtgatctaa gtggattgaa    360
gaagaagcga gcaatcatac acactactct attggtagct gctgtggttg cgctgttgac    420
atcagtttgc acccttttcaa gcgatgccag tgtggccttt aagataaatg aactaagac    480 agaagtgcct tcatggttta aaagccttaa cccggccctt ggcgttgtca atttgggagc    540 aactttttg ccgccgttt cgcaaagag tgaaagagcc ttgaaccagc agatagatgc     600
cataaagaag gaggtggcca agaaacaatc ttataatgac gcggtgaggg ccagttttac    660
ggagttctcg tcaatcccgc tggatggttt cgaagcccca ttaacctgag gacagtaggt    720
agagtggcgc cccgaggttt gcgtcgtgca gggtggttga cctcgcggcg tagactccca    780
ctgctgtata acggggagg gtgcgcgaca ctacacactt ac                       822
```

<210> SEQ ID NO 88
<211> LENGTH: 822
<212> TYPE: DNA
<213> ORGANISM: Artificial Sequence
<220> FEATURE:
<223> OTHER INFORMATION: *C) BTV6 Seg-10 of 'NS3knockout DIVA'

<400> SEQUENCE: 88

```
gttaaaaagt gtcgctgccg ccctatccgg gctgatccaa aggttcgaag aagaaagggc     60
caaacacaat caagatagag ttgaagagct gagtctagtg cgtgtatagg ataccatttc    120
tcaaccacca aggtaggccc cgagtgcgcc ggccccatca tctgcccaa cggttgccct     180 tgaaatattg acaaggcgg cctcaaacac aactggtgca acgcaaacac agaaagcgga    240
gaaggcagct tttgctagct atgcggaagc gtttcgtgat gatgtgagat tgagacagat    300
caaacgccat gtgaacgagc agattttacc aaaattaaaa agtgatctaa gtggattgaa    360
gaagaagcga gcaatcatac acactactct attggtagct gctgtggttg cgctgttgac    420
atcagtttgc acccttttcaa gcgatgccag tgtggccttt aagataaatg aactaagac    480 agaagtgcct tcatggttta aaagccttaa cccggccctt ggcgttgtca atttgggagc    540 aactttttg ccgccgttt cgcaaagag tgaaagagcc ttgaaccagc agatagatgc     600
cataaagaag gaggtggcca agaaacaatc ttataatgac gcggtgaggg ccagttttac    660
ggagttctcg tcaatcccgc tggatggttt cgaagcccca ttaacctgag gacagtaggt    720
agagtggcgc cccgaggttt gcgtcgtgca gggtggttga cctcgcggcg tagactccca    780
ctgctgtata acggggagg gtgcgcgaca ctacacactt ac                       822
```

<210> SEQ ID NO 89
<211> LENGTH: 757
<212> TYPE: DNA
<213> ORGANISM: Bluetongue virus 10

<400> SEQUENCE: 89

```
gttaaaatta tcccttgtca tgaatctagc tacaatcgcc aagaattata gcatgcataa     60
tggagagtcg ggggcgatcg tcccttatgt gccaccacca tacaatttcg caagtgctcc    120
gacgttttct cagcgtacga gtcaaatgga gtccgtgtcg cttgggatac ttaaccaagc    180
```

| | |
|---|---|
| catgtcaagt acaactggtg cgagtggggc gcttaaagat gaaaaagcag cattcggtgc | 240 |
| tatggcggaa gcattgcgtg atccagaacc catacgtcaa attaaaaagc aggtgggtat | 300 |
| cagaacttta agaacctaa agatggagtt agcaacaatg cgtcgaaaga aatcggcatt | 360 |
| aaaaataatg atctttatta gtggatgcgt aacgttagct acatcgatgg ttggggggatt | 420 |
| gagtatcgtt gacgacgaaa tattaagaga ttataagaac aacgattggt taatgaagac | 480 |
| tatacatggg ctgaatttgt tatgtactac agttttgtta gcggcgggta agatttccga | 540 |
| taaaatgcaa gaggagattt cacggactaa acgtgacatt gcgaaaagag agtcttacgt | 600 |
| gtcagcggcg agtatgtcgt ggagtggaga tactgagatg ttattacagg gaattaagta | 660 |
| tggcgagagc tagtatgacc tccacgagcg gaaaatccat cgtgttggat ggatggaacg | 720 |
| cctagatcgt tttctaggga gtgggataac aacttac | 757 |

```
<210> SEQ ID NO 90
<211> LENGTH: 757
<212> TYPE: DNA
<213> ORGANISM: Artificial Sequence
<220> FEATURE:
<223> OTHER INFORMATION: AUG->GCC mutations of start codons of NS3 and
      NS3a and STOP codons downstream of AUG2

<400> SEQUENCE: 90
```

| | |
|---|---|
| gttaaaatta tcccttgtcg ccaatctagc tacaatcgcc aagaattata gcgcccataa | 60 |
| tggagagtga ggggcgatcg tcccttaagt gccaccacca tagaatttcg caagtgctcc | 120 |
| gacgttttct cagcgtacga gtcaaatgga gtccgtgtcg cttgggatac ttaaccaagc | 180 |
| catgtcaagt acaactggtg cgagtggggc gcttaaagat gaaaaagcag cattcggtgc | 240 |
| tatggcggaa gcattgcgtg atccagaacc catacgtcaa attaaaaagc aggtgggtat | 300 |
| cagaacttta agaacctaa agatggagtt agcaacaatg cgtcgaaaga aatcggcatt | 360 |
| aaaaataatg atctttatta gtggatgcgt aacgttagct acatcgatgg ttggggggatt | 420 |
| gagtatcgtt gacgacgaaa tattaagaga ttataagaac aacgattggt taatgaagac | 480 |
| tatacatggg ctgaatttgt tatgtactac agttttgtta gcggcgggta agatttccga | 540 |
| taaaatgcaa gaggagattt cacggactaa acgtgacatt gcgaaaagag agtcttacgt | 600 |
| gtcagcggcg agtatgtcgt ggagtggaga tactgagatg ttattacagg gaattaagta | 660 |
| tggcgagagc tagtatgacc tccacgagcg gaaaatccat cgtgttggat ggatggaacg | 720 |
| cctagatcgt tttctaggga gtgggataac aacttac | 757 |

```
<210> SEQ ID NO 91
<211> LENGTH: 725
<212> TYPE: DNA
<213> ORGANISM: Artificial Sequence
<220> FEATURE:
<223> OTHER INFORMATION: Deletion of the putative Late Domain

<400> SEQUENCE: 91
```

| | |
|---|---|
| gttaaaatta tcccttgtca tgaatctagc tacaatcgcc aagaattata gcatgcataa | 60 |
| tggagagtcg ggggcgatcg tcccttatgt ggttttctca gcgtacgagt caaatggagt | 120 |
| ccgtgtcgct tgggatactt aaccaagcca tgtcaagtac aactggtgcg agtggggcgc | 180 |
| ttaaagatga aaaagcagca ttcggtgcta tggcggaagc attgcgtgat ccagaaccca | 240 |
| tacgtcaaat aaaaagcag gtgggtatca gaacttaaa gaacctaaag atggagttag | 300 |
| caacaatgcg tcgaaagaaa tcggcattaa aaataatgat ctttattagt ggatgcgtaa | 360 |

```
cgttagctac atcgatggtt gggggattga gtatcgttga cgacgaaata ttaagagatt    420
ataagaacaa cgattggtta atgaagacta tacatgggct gaatttgtta tgtactacag    480
ttttgttagc ggcgggtaag atttccgata aaatgcaaga ggagatttca cggactaaac    540
gtgacattgc gaaaagagag tcttacgtgt cagcggcgag tatgtcgtgg agtggagata    600
ctgagatgtt attacaggga attaagtatg gcgagagcta gtatgacctc cacgagcgga    660
aaatccatcg tgttggatgg atggaacgcc tagatcgttt tctagggagt gggataacaa    720
cttac                                                                 725
```

<210> SEQ ID NO 92
<211> LENGTH: 757
<212> TYPE: DNA
<213> ORGANISM: Artificial Sequence
<220> FEATURE:
<223> OTHER INFORMATION: AUG->GCC mutation of all AUG codons in ORF of
     NS3/NS3a

<400> SEQUENCE: 92

```
gttaaaatta tcccttgtcg ccaatctagc tacaatcgcc aagaattata gcgcccataa     60
tggagagtcg ggggcgatcg tcccttatgt gccaccacca tacaatttcg caagtgctcc    120
gacgttttct cagcgtacga gtcaagccga gtccgtgtcg cttgggatac ttaaccaagc    180
cgcctcaagt acaactggtg cgagtggggc gcttaaagat gaaaaagcag cattcggtgc    240
tgccgcggaa gcattgcgtg atccagaacc catacgtcaa attaaaaagc aggtgggtat    300
cagaacttta agaacctaa aggccgagtt agcaacagcc cgtcgaaaga atcggcatt    360 aaaaatagcc atctttatta gtggatgcgt aacgttagct acatcggccg ttgggggatt    420
gagtatcgtt gacgacgaaa tattaagaga ttataagaac aacgattggt tagccaagac    480
tatacatggg ctgaatttgt tatgtactac agttttgtta gcggcgggta agatttccga    540
taaagcccaa gaggagattt cacggactaa acgtgacatt gcgaaaagag agtcttacgt    600
gtcagcggcg agtgcctcgt ggagtggaga tactgaggcc ttattacagg gaattaagta    660
tggcgagagc tagtatgacc tccacgagcg gaaaatccat cgtgttggat ggatggaacg    720
cctagatcgt tttctaggga gtgggataac aacttac                              757
```

<210> SEQ ID NO 93
<211> LENGTH: 757
<212> TYPE: DNA
<213> ORGANISM: Artificial Sequence
<220> FEATURE:
<223> OTHER INFORMATION: 1* + 3* and mutations in a conserved region

<400> SEQUENCE: 93

```
gttaaaatta tcccttgtcg ccaatctagc tacaatcgcc aagaattata gcgcccataa     60
tggagagtga ggggcgatcg tcccttaagt gccaccacca tagaatttcg caagtgctcc    120
gacgttttct cagcgtacga gtcaagccga aagtgtaagt ttagggatac ttaaccaagc    180
cgcctcaagt acaactggtg cgagtggggc gcttaaagat gaaaaagcag cattcggtgc    240
tgccgcggaa gcattgcgtg atccagaacc catacgtcaa attaaaaagc aggtgggtat    300
cagaacttta agaacctaa aggccgagtt agcaacagcc cgtcgaaaga atcggcatt    360 aaaaatagcc atctttatta gtggatgcgt aacgttagct acatcggccg ttgggggatt    420
gagtatcgtt gacgacgaaa tattaagaga ttataagaac aacgattggt tagccaagac    480
tatacatggg ctgaatttgt tatgtactac agttttgtta gcggcgggta agatttccga    540
```

```
taaagcccaa gaggagattt cacggactaa acgtgacatt gcgaaaagag agtcttacgt      600
gtcagcggcg agtgcctcgt ggagtggaga tactgaggcc ttattacagg gaattaagta      660
tggcgagagc tagtatgacc tccacgagcg gaaaatccat cgtgttggat ggatggaacg      720
cctagatcgt tttctaggga gtgggataac aacttac                               757

<210> SEQ ID NO 94
<211> LENGTH: 442
<212> TYPE: DNA
<213> ORGANISM: Artificial Sequence
<220> FEATURE:
<223> OTHER INFORMATION: delTMR1: AUG1+2 in combination with a deletion
      in Seg-10 encompassing transmembrane region 1 (TM1)

<400> SEQUENCE: 94
gttaaaatta tcccttgtca tgaatctagc tacaatcgcc aagaattata gcgcccataa       60
tggagagtcg ggggcgatcg tcccttatgt gccaccacca tacaatttcg caagtgctcc      120
gacgttttct cagcgtacta agaacaacga ttggttaatg aagactatac atgggctgaa      180
tttgttatgt actacagttt tgttagcggc gggtaagatt ccgataaaa tgcaagagga       240 gatttcacgg actaaacgtg acattgcgaa aagagagtct tacgtgtcag cggcgagtat      300
gtcgtggagt ggagatactg agatgttatt acagggaatt aagtatggcg agagctagta      360
tgacctccac gagcggaaaa tccatcgtgt tggatggatg aacgcctag atcgttttct       420 agggagtggg ataacaactt ac                                               442

<210> SEQ ID NO 95
<211> LENGTH: 612
<212> TYPE: DNA
<213> ORGANISM: Artificial Sequence
<220> FEATURE:
<223> OTHER INFORMATION: delTMR2: AUG1+2 in combination with a deletion
      in Seg-10

<400> SEQUENCE: 95
gttaaaatta tcccttgtcg ccaatctagc tacaatcgcc aagaattata gcgcccataa       60
tggagagtcg ggggcgatcg tcccttatgt gccaccacca tacaatttcg caagtgctcc      120
gacgttttct cagcgtacga gtcaaatgga gtccgtgtcg cttgggatac ttaaccaagc      180
catgtcaagt acaactggtg cgagtggggc gcttaaagat gaaaaagcag cattcggtgc      240 tatgcggaa gcattgcgtg atccagaacc catacgtcaa attaaaaagc aggtgggtat       300
cagaacttta aagaacctaa agatggagtt agcaacaatg cgtcgaaaga atcggcatt      360 aaaaataatg atctttatta gtggatgcgt aacgttagct acatcgatgg ttgggggatt      420
gagtatcgtt gacgacgaaa tattaagaga ttagtgtcag cggcgagtat gtcgtggagt     480
ggagatactg agatgttatt acagggaatt aagtatggcg agagctagta tgacctccac     540
gagcggaaaa tccatcgtgt tggatggatg aacgcctag atcgttttct agggagtggg      600
ataacaactt ac                                                          612

<210> SEQ ID NO 96
<211> LENGTH: 486
<212> TYPE: DNA
<213> ORGANISM: Artificial Sequence
<220> FEATURE:
<223> OTHER INFORMATION: NS3 TM

<400> SEQUENCE: 96
atgctgtcgg gtctgatcca acgctttgaa gaagaaaaaa tgaaacataa ccaagatcgt       60
```

```
gtcgaagaac tgtcactggt ccgtgtggat gacaccattt cacagccgcc gcgttatgca    120
ccgtcggctc cgatgccgag ctctatgccg accgttgccc tggaaatcct ggataaagca    180
atgtctaaca ccacgggcgc aacccagacg caaaaggctg aaaaagcggc ctttgcgagc    240
tacgcggaag ccttccgtga tgacgttcgt ctgcgccaga ttaaacgcca tgtcaatgaa    300
caaatcctgc cgaagctgaa aagcgatctg tctggcctga aaaagaaaag tgaacgtgcc    360
ctgaaccagc aaatcgatat gatcaagaaa gaagtcatga agaaacagag ctataatgac    420
gccgtgcgca tgtctttac cgaattctca tcggttccgc tggatggttt cgaaatgccg    480
ctgacg                                                                486

<210> SEQ ID NO 97
<211> LENGTH: 22
<212> TYPE: DNA
<213> ORGANISM: Artificial Sequence
<220> FEATURE:
<223> OTHER INFORMATION: deletion segment S10

<400> SEQUENCE: 97
gttaaaaagt gtcgctgcca tg                                              22
```

VACCINES FOR DISEASES CAUSED BY VIRUSES OF THE FAMILY OF REOVIRIDAE

RELATED APPLICATIONS

This application is the U.S. National Stage of International Application No. PCT/NL2014/050312, filed May 16, 2014, published in English, and claims the benefit of European Application Number 13168061.3, filed on May 16, 2013 and European Application Number 13194912.5, filed on Nov. 28, 2013, the entire teachings of the above applications are incorporated herein by reference.

SEQUENCE LISTING

The instant application contains a Sequence Listing which has been submitted in ASCII format via EFS-Web and is hereby incorporated by reference in its entirety. Said ASCII copy, created on Jan. 31, 2017 is named P101098US00 seqlist_ST25_jan2017 and is 41,198 bytes in size.

Field: The invention relates to the field of viruses, more specifically, to the field of molecular virology of Reoviridae, including Sedoreovirinae and Spinareovirinae. The invention relates to methods for the generation of a propagation-competent strain of a mutant Reoviridae virus, and to a virus that is produced by these methods. The resulting virus can be used as a vaccine to protect plants and animals, including humans, against an infectious disease mediated by Reoviridae.

Viruses belonging to the family of Reoviridae have a genome consisting of up to 12 genome segments of double stranded RNA (dsRNA) and cause many diseases in all kind of organisms, including plants, animals and humans. The virus particles consist of several protein layers without an envelope.

The Reoviridae family has been divided in two subfamilies, which are the Sedoreovirinae with six genera and the Spinareovirinae with nine genera. Thus far, there is one unclassified genus, Crabreovirus.

Orbivirus is the largest genus within Sedoreovirinae with 22 virus species and 13 unassigned viruses. Orbiviruses cause widespread diseases in a variety of animal species, including humans. The economically most important examples of Orbiviruses are the virus species or serogroups Bluetongue virus (BTV) and Epizootic Haemorrhagic Disease Virus (EHDV), which cause disease in all kind of ruminants, and the serogroups African Horse Sickness Virus (AHSV) and Equine Encephalosis Virus (EEV), which cause disease in equines. BTV commonly affects cattle, sheep, goats, buffalo, deer, dromedaries and antelope, EHDV commonly affects deer, cattle and sheep, whereas AHSV and EEV commonly affects horses, mules, donkeys and zebras.

Orbiviruses are non-contagious viruses. Although several transmission routes have been described, the major route of transmission is through bites of infected insects, termed vectors. Well-known competent insect vectors of orbiviruses in Africa/Asia are *Culicoides imicola* and *C. bolinitos*. In North-America, *C. sonorensis* has been recognized as insect vector of BTV, although expansion of some BTV serotypes is associated with other *Culicoides* species. In South-America, *C. insignis* and *C. pusillus* are recognized as vectors, while *C. brevetarsis, C. fulvus* and *C. waldai* are recognized as vectors in Australia. In Europe, BTV-positive *C. obsoletus, C. dewulfi, C. publicaris* and *C. chiopterus* have been found, whereas *C. imicola* is the best candidate to spread BTV in the southern part of Europe.

Orbiviruses can vary in all kind of characteristics, like virulence, host tropism, and insect vector preference. Obviously, all these features are not associated to a specific serotype. Serotypes have been defined as a group of virus strains showing a high level of cross-neutralization. A lower level of cross-neutralization within an orbivirus serogroup has resulted in subgrouping. Each of the orbivirus serogroups consists of a variable number of serotypes. Thus far, 7-9 serotypes have been reported for each of the serogroups AHSV, EHDV and EEV, and at least 26 BTV serotypes. Cross-neutralization indexes correlate with phylogenetic data, in particular for genome segment 2 (S2) which encodes the outer capsid protein VP2.

Viruses with a segmented genome, such as Reoviridae, can reassort, which is in fact remixing of genome segments of two or more viruses, resulting very rapidly in new virus variants. This reassortment can combine previously separated characteristics like virulence and serotype without any additional mutations (Shaw et al., 2013. J Virol 87: 543-557). Reassortment between viruses with a segmented genome is well-known as 'genetic shift'. Not all possible reassortants have been identified in nature, but it is not conclusive whether these were not formed, are not viable, or will disappear quickly because they are overgrown by more fit variants. In the laboratory, however, many more natural reassortants and forced or 'synthetic' reassortants can be generated (Shaw et al., 2013. J Virol 87: 543-557). Further, it can be speculated that reassortment is a rare event in nature, and only occurs by chance in double infected cells in the host or insect vector, but it is obvious that only successful reassortants will evolve as a result of positive selection. So far, reassortants between members of two different virus species have not been found, and is generally accepted as one of the criteria to divide new viruses into serogroups or virus species.

Control of insect-borne diseases by conventional measures, such as standstill of susceptible animals and removal of infected animals, has met little success. Control of vectors appeared even impossible as well as preventing the biting of these midges. Protection of animals by vaccination has been attempted by using live-attenuated/modified-live vaccine (MLV) or dead vaccine (inactivated virus) for BT and AHS. For BTV, dead vaccine is available for a few serotypes. For AHSV, currently dead vaccines are not available. Vaccines are not available for EHDV and EEV. Several examples of other types of vaccines, like vector vaccines, subunit vaccines and virus-like particles, are present in the scientific literature for a long time, but have not been marketed yet.

Vaccines have been used as 'single serotype' vaccine, although in some instances a cocktail containing more than one serotype has been used. A cocktail of MLVs provides protection against the included serotypes, and sometimes results in protection against additional serotypes. Particularly, broader protective immune responses were raised by successive vaccinations with different serotypes.

Traditionally manufactured MLVs are very effective and cheap, but suffer from a number of drawbacks. Under-attenuation leads to clinical signs by vaccination. Genetic instability can result in reversal to virulence. Reassortment between vaccine virus and field virus, or between vaccine viruses (in a cocktail vaccine) can result in virulent virus variants. All these lead to the same outcome; clinical signs and uncontrolled spread of virulent variants by onward transmission.

Further, animals vaccinated with MLV cannot be distinguished from naturally infected animals. This hampers adequate control of outbreaks caused by Reoviridae, including orbiviruses.

Dead vaccines are considered very safe and have been used as single as well as cocktail vaccine. Bluetongue, which is caused by different serotypes in Europe, has mainly been controlled by vaccination with dead vaccines. Dead vaccines however are relatively expensive, due to a higher antigen load per dose, a requirement of a prime-boost approach for full protection; and a requirement of annual re-vaccination. The higher costs are also associated with post-production processes, like the inactivation process (including safety issues) and formulation.

In addition, the presently available dead vaccines are not suitable as DIVA (Differentiating Infected animals from Vaccinated Animals) vaccine. It has been published for Bluetongue and African horse sickness that differentiation between vaccinated and infected animals based on the humoral response against non-structural (NS)-proteins is possible (Barros et al., 2009. Vet Microbiol 137: 252-259; Laviada et al., 1995. Virus Res 38: 205-218). However, the impurity of dead vaccines that have been used can cause induction of antibodies against the target NS protein, in particular after repeated vaccination. Consequently, vaccination with dead vaccine resulted in undesired seropositivity for the target NS protein. The vaccinated animals were considered to be infected animals, as determined by a relevant DIVA-associated assay.

In summary, MLVs and dead vaccines have been marketed and applied, in particular for Reoviridae, including Orbiviruses such as BTV. Several drawbacks are well-known regarding important criteria for application of vaccine. Proof of principle has been achieved for all kinds of experimental vaccines, like VP2 subunit vaccines, virus-like particles, Disabled Infectious Single Cycle (DISC) vaccines, DNA vaccines, etc. These experimental vaccines have several advantages but also important shortcomings, of which production costs, short shelf life and cold chain problems, limited application, and temporary or incomplete protection are the most important. Likely, this is the most important reason that these vaccines are not further explored. Therefore, improvement of currently marketed vaccines is desperately needed by new approaches to combat these insect-borne diseases caused by Reoviridae, including Orbiviruses such as BTV.

Therefore, the present invention provides a method for producing a propagation-competent strain of a mutant Reoviridae virus comprising a functional deletion in a viroporin-coding region that abolishes expression of substantially all endogenous viroporin proteins, the method comprising a) introducing the mutant Reoviridae virus in a non-complementing cell line; b) passaging said mutant virus in said cell line until virus is produced; and c) propagating the propagation-competent strain of the mutant virus. It was found that a propagation competent virus harboring additional alterations could be rescued after several passages of the mutant Reoviridae virus on a non-complementing cell line. Said mutant Reoviridae virus comprising a functional deletion in a viroporin-coding region is either not replication competent, in which case the cell line expresses a replication complementing factor, or, preferably, is replication competent.

Replication competent, as is used herein, is defined as 'able to multiply in a cell' but not necessarily able to leave the cell and/or to re-infect other cells.

Propagation competent, as is used herein, is defined as 'able to multiply in a cell and to re-infect other cells', at least in vitro. A propagation competent virus can be propagated in cell culture.

Said mutant virus is preferably a Reoviridae virus, more preferably of the Sedoreovirinae. A most preferred parent virus is an Orbivirus, including Bluetongue virus (BTV), Epizootic Haemorrhagic Disease Virus (EHDV), African Horse Sickness Virus (AHSV), and Equine Encephalosis Virus (EEV). Further Orbivirus species are Chuzan virus, Corriparta virus, Eubenengee virus, Eubenengee virus, Ngoupe virus, Tilligerry virus, Great Island virus, Broadhaven virus, Great Island virus, Kemerovo virus, Lipovnik virus, Tribec viruses, Lake Clarendon virus, Palyam virus, CSIRO Village virus, Pata virus, Peruvian horse sickness virus, Elsey virus, St Croix river virus, Umatilla virus, Stretch Lagoon virus, Umatilla virus, Wallal virus, Warrego virus, Wongorr virus, Yunnan virus, and Middle Point virus.

Reoviruses, including Orbivirus such as BTV, are cytoplasmic viruses. A viral infection cycle is characterized by six major steps: attachment, entry, uncoating, synthesis of nucleic acids and proteins, assembly, and release. Propagation of a Reovirus requires all steps. Interference with any one of these steps hampers propagation of the virus. A preferred mutation hampers propagation of the mutant virus in a cell or cell line in which the parent virus is able to propagate. Preferably, the mutation is in a viral protein that is not involved in multiplying genome and expression of genes, and is not involved in the induction of the protective immune response, for example the neutralizing immune response. A mutant virus preferably comprises a functional deletion in a genetic region that is relevant for in vivo propagation of the virus. A preferred functional deletion is in a genetic region that is associated with release of viral particles from infected cells, most preferred in a viroporin-coding region such as, for example, NS3/NS3a of Orbiviruses (Han and Harty, 2004 J Biol. Chem. 279: 43092-43097). This region corresponds to the region encoding NSp4 of Rotavirus, and p10 of avian Orthoreovirus-coding region, that also contain viroporin-like properties.

Viroporins are a group of small glycoproteins that can oligomerize and participate in several viral functions, including the promotion of virus release from infected cells. Viroporins are not essential for virus replication. Viroporins can create a transmembrane aqueous pore by which the passage of ions and small molecules is enhanced. Viroporins have some common structural motifs, such as a highly hydrophobic transmembrane domain that interacts with and expands the lipid bilayer. This domain forms an amphipathic α-helix and a cluster of basic (positively charged) residues that electrostatically interact with negatively charged phospholipids to aid in membrane insertion (Gonzalez and Carrasco, 2003. FEBS Lett 552: 28-34). NS3/NS3a of orbiviruses possesses properties commonly associated with viroporins: NS3 localizes to the Golgi apparatus and plasma membrane, NS3 can homo-oligomerize, co-localization of NS3 to Golgi and plasma membranes correlates with the enhanced permeability of cells for small molecules, and the transmembrane region 1 (TM1) of NS3 is critical for this viroporin-like property. These viroporin-like properties may contribute to the role of NS3/NS3a in virus release (Han and Harty, 2004. J Biol Chem 279: 43092-43097).

Although the term NS3/NS3a is used herein below as a preferred viroporin-coding region, it is expressly stated that the invention also includes a mutant Reoviridae virus comprising a functional deletion in corresponding viroporin-coding regions, such as NSp4 of Rotavirus, or p10 of avian Orthoreovirus-coding region.

The term "functional deletion", as used herein, refers to a genetic alteration that abolishes expression of a protein or proteins that is/are encoded by the virus and that is/are associated with propagation of the virus. A virus comprising a functional deletion in a viroporin-coding region preferably is not propagation competent, at least not in vivo. A functional deletion in an Orbivirus abolishes expression of endogenous NS3 and NS3a proteins and any other NS3-related protein.

The term "endogenous protein" refers to a protein that is encoded by a unaltered, wild type virus not having said functional deletion.

The expression of an endogenous viroporin protein is abolished if there is no expression of the endogenous protein at all, if the amino acid composition of the viroporin protein has been altered compared to the amino acid composition of the protein that is encoded by a unaltered, wild type virus not having said functional deletion, and/or if the mass of the protein is reduced, for example by deletion of a part of the coding region.

Said functional deletion or mutation is either an insertion, a point mutation, or, preferably, two or more point mutations, or, more preferably, a deletion. A preferred functional deletion comprises the alteration of an ATG translational start codon of NS3 and/or of NS3 and NS3a, more preferably of both NS3 and NS3a. Said alteration preferably comprises the alteration of the ATG translational start codon into the triplet "GCC", preferably of both start codons. A further preferred alteration comprises the introduction of a premature stop codon into the coding region of a viroporin-encoding region, preferably NS3 and/or NS3a. A further preferred alteration comprises the alteration of premature start codons (AUG-GCC) in the coding region of a viroporin-encoding region, preferably NS3/NS3a.

The term "deletion" covers the replacement of nucleotide sequences in a genomic segment of a Reoviridae virus that is relevant for propagation of the virus for other nucleotide sequences, for example marker sequences such as sequences that encode green fluorescent protein. A preferred deletion covers more than 10 nucleotides. This helps to ensure that the virus does not revert back to a propagation-competent, pathogenic and/or transmittable phenotype known as 'reverse to virulence' or 'genetic drifting'. A preferred deletion is a single, large deletion or a combination of several deletions. Again, this helps to ensure that the virus does not revert back to a propagation-competent, pathogenic and/or transmittable phenotype.

It is common general knowledge that a genetic region that is associated with propagation of a virus, preferably release of a virus from infected cells, cannot be inactivated without apparent loss of the full propagating properties of the virus. A virus that comprises such inactivation is normally produced in a complementing cell line that expresses an RNA and/or protein of which the expression is lost by the functional deletion in a genetic region that is relevant for propagation of the virus. However, when used as a vaccine, said virus will be less effective as it is not propagated in a vaccinated animal because this animal does not express the complementing RNA and/or protein. The present inventors surprisingly established that a mutant virus, that comprises a functional deletion in the NS3/NS3a coding region, is able to propagate in a non-complementing cell line after repeated passaging of the virus. Said passaging is performed in the absence of any sign that a virus is produced, such as the formation of cytopathogenic effect (CPE) and/or cell lysis. It was found that by passaging the mutant virus, a stable, self-propagating virus is generated that in some instances seemed to compensate for the inactivation of the genetic region that is associated with propagation of the virus, without restoration of the functional deletion.

The term "non-complementing cell line", as used herein, refers to a cell line in which the parent virus is able to replicate and propagate, and in which the mutation that is present in the mutant virus is not complemented, for example by expression of a corresponding, not mutated, protein. For example, a non-complementing cell line of a mutant Reoviridae virus comprising an alteration, preferably a deletion, in a gene encoding NS3/NS3a glycoproteins, does not express proteins that can compensate for the loss of the NS3/NS3a glycoproteins such as, for example, the NS3/NS3a glycoproteins themselves.

The genus Orbivirus currently contains 22 species or serogroups and at least 130 different serotypes. Orbiviruses contain 10 genome segments S1-S10 encoding at least 11 proteins (Attoui et al., 2009. In: Mellor, P., Baylis, M., Mertens, P. (Eds.) Biology of animal infections: Bluetongue. Academic Press, Amsterdam, 23-46). The virus particle contains the viral proteins (VP) encoded by genome segment S1 [VP1], S2 [VP2], S3 [VP3], S4 [VP4], S6 [VP5], S7 [VP7] and S9 [VP6]. Of these, VP1, VP4 and VP6 appear to be enzymatic proteins. VP7 is highly conserved within one serogroup and is a preferred target for serogroup-specific serological assays, like Enzyme-Linked Immuno-Sorbent Assays (ELISAs). Indirect ELISAs (iELISAs) and competitive or blocking ELISAs (cELISAs) are variants of this assay. Antibodies against VP7 are not neutralizing, although infection by core particles could be reduced by VP7-antibodies. VP2 and VP5 form the outer shell of the virus particle. VP2 is the major target of neutralizing antibodies (nAbs). This humoral response is highly protective and specific for the respective serotype. Viral proteins that are not part of the virus particle, termed non-structural proteins (NS), are encoded by genome segments S5 [NS1], S8 [NS2], S10 [NS3/NS3a], and the recently discovered non-structural protein NS4. The ORF of NS3a is in-frame with that of NS3 and only varies in length at the N-terminal end by translation starting from a second in-frame start codon. This difference in length is highly conserved within each Orbivirus serogroup, but not between serogroups. This difference is, for example, 13 amino acid residues (aa) for BTV. In contrast to NS3/NS3a, NS4 is encoded by an internal +1 open reading frame (ORF) of S9 [VP6]. The function of NS4 has not been resolved yet (Ratinier et al., 2011. PLoS Pathog 7, e1002477).

Said virus is preferably BTV, EHDV, AHSV or EEV, more preferably BTV or AHSV.

Bluetongue (BT) is an emerging disease of wild ruminants and livestock which has a huge economic impact on European and non-European agriculture. BTV of every serotype can cause disease in sheep, goats, and cattle, and variants differing in virulence exist for each serotype. The mortality by BTV infection can reach 70% of the infected animals depending on the virus involved, and species and breed of the host. BT is endemic in many tropical and sub-tropical countries, Australia and the Americas.

African Horse Sickness (AHS) is endemic in large parts of the African continent and is incidentally (re-)emerging outside this continent, like in the Arabian and Iberian Peninsula. All nine AHSV serotypes cause serious disease in equines, in particular in domestic horses. The mortality in domestic horses can reach 90% or higher. Therefore, AHS is an important disease for the equine population in developing countries, and a serious threat for developed countries. The impact of AHS is huge in economic and emotional terms.

Epizootic Haemorrhagic Disease (EHD is less widespread, but is frequently reported by several countries. EHDV is reported in North America, in the far east, and at the border of Europe (Israel and Morocco). Spread of EHD is commonly reported in deer, in particular white-tailed deer. EHDV is frequently spread to other ruminant species like livestock causing serious disease comparable to Bluetongue.

Equine Encephalosis (EE) has expanded to northern parts of the African continent, and even up to Israel. EE is much less severe than AHS and the percentage of mortality is very low compared to AHS. At present the outcome of infection in domestic horses is not well determined, and the effects on the performance of the previously infected and recovered horses is unknown.

Since 1998, incursions of BTV into Europe have been common events, reaching as far north as Sweden in 2007. Since then, many different serotypes (BTV1, 2, 4, 6, 8, 9, 11, 14, 16, and a recently discovered 25th serotype) have invaded into Europe, either temporarily or permanently. These incursions have occurred via at least three different routes and by at least 10 occasions. Intensified trade in wild animals, livestock and plant materials (with infected midges), tourism, and incursion by wind of infected midges are considered as possible introduction routes. However, most incursions remained unsolved. Regarding expansion of Bluetongue, the expansion and increased density of known competent insect vectors, and transmission by novel endemic vector species, are factors to be considered for transmission of BTV. In addition, intensified European animal movements related to trade of livestock and livestock-related products, are also considered to be associated with the increase of BTV transmission within Europe.

The existence of undiagnosed infections in livestock and wild ruminants coupled with the rapid spread over short and large distances by movement of insect vectors has attributed to the introduction of BTV in Europe. By expansion of known competent insect vectors and by adaptation of BTV to endemic insect vectors, BT now represents a serious threat for livestock in all European countries. Different BTV serotypes are circulating in Europe and have resulted in the deaths of millions of animals. Further, several European countries are facing a multi-serotype situation, by which more than one serotype is circulating at the same time. Similar situations exist for a longer period in Australia, Asia, Africa, and the Americas.

A mutant Reoviridae virus, preferably a mutant Orbivirus, can be generated by means known in the art, preferably by reverse genetics. Reverse genetics (RG) is a methodology that is well-known to a person skilled in the field of molecular virology of RNA viruses. In the last decades, RG has been developed for virus families with genomes consisting of single stranded RNA (ssRNA) of positive or negative polarity, double stranded RNA (dsRNA), and for virus families with non-segmented RNA genomes and segmented RNA genomes (up to 12 genome segments). Thus, RG is a well-known method to rescue synthetic RNA-virus of any kind from one or more cDNAs.

RG is a procedure to generate RNA-virus (here named 'synthetic virus') from copy DNA (cDNA) based on the sequence of viral RNA. The methodology preferably comprises the steps of synthesis of cDNA from viral RNA, in vitro synthesis of RNA from cDNA using a DNA-dependent RNA polymerase, and regeneration of synthetic virus based on this RNA. Alternatively, in vitro RNA synthesis can be skipped by in vivo RNA synthesis after transfection of cells with cDNA (van Gennip et al., 1999. J Virol Methods 78, 117-128).

Synthetic Reoviridae virus, preferably Orbivirus, can be produced by use of copy DNA (cDNA) clones of genome segments. Genomic viral cDNA sequences are flanked upstream with promoter sequences of a DNA dependent RNA polymerases and downstream with RIBOzyme sequences. Infectious RNA virus is recovered from cells transfected with such plasmids. By this method, RNA is synthesized in vivo, proteins are expressed and subsequently 'synthetic' virus is assembled (Kobayashi et al., 2007. Cell Host Microbe 1, 147-157). A DNA-dependent RNA polymerase, preferably SP6 polymerase or T7 RNA polymerase, is expressed in a cell by infection with another virus expressing the DNA-dependent RNA polymerase (Britton et al., 1996), preferably a fowlpoxvirus-based expression vector that encodes the T7 polymerase, or, preferably, is constitutively expressed in a cell.

For example, synthetic bluetongue virus (rgBTV) is generated by use of cDNA clones for in vitro synthesis of ssRNAs followed by transfection to cells, preferably mammalian cells. Here, cDNAs are flanked at the 5' end by the promoter sequences of a DNA dependent RNA polymerase, for example T7 RNA polymerase, and at the 3' end with a recognition site of a restriction enzyme (RE) not present in the cDNA. Digestion of cDNA by the respective unique RE followed by RNA synthesis results in run-off RNA transcripts that can be used for transfection. Infectious rgBTV has been recovered from cells transfected with these ssRNAs. After transfection of ssRNAs, proteins were expressed and subsequently virus particles were assembled (Boyce et al., 2008. J Virol 82, 8339-8348). More recently, it has been shown that nonvirulent and virulent BTV isolates can be synthetically generated. These viruses are phenotypically indistinguishable from the respective field isolate (van Gennip et al., 2012. Plos One 7(2): e30540).

Alternatively, ssRNAs are synthesized of cDNAs of one or more genome segments of the orbiviral genome in vitro. Transfection of these synthetic RNAs to cells that were previously transfected with RNA isolated from purified virus particles results in synthetic RNA that is incorporated into rescued Orbivirus (Boyce and Roy, 2007. J Virol 81, 2179-2186; Matsuo et al., 2010. J Virol 85, 10213-10221). Transfection of synthetic RNA to BTV-infected cells has also resulted in uptake of synthetic genome segments (van Gennip et al., 2010. Virol J 7, 261). All these can be considered as synthetic orbivirus, since at least one genome segment originates from synthetic RNA.

Alternatively, transfection of all ten synthetic RNAs to cells that were previously transfected with expression plasmids for VP1, VP3, VP4, VP6, NS1 and NS2 and the respective in vitro synthetized ssRNAs resulted in synthetic Orbivirus (Matsuo and Roy, 2013. J Virol 87 882).

The rescue of viruses with segmented RNA genomes is preferably further explored by combination of ssRNA or cDNA originating from different viruses, preferably from within one serogroup. For example, if the virus is BTV, a set of 10 ssRNAs or cDNA may consist of segments of attenuated BTV and segments of field virus. Preferably, the segments of field virus encodes VP2 and VP5 representing a serotype of interest. The ssRNA or cDNA may encode a variety of immunologically important proteins from a number of different viral serotypes of Reoviridae, preferably from one serogroup, whereby one of the ssRNA or cDNA comprises a functional deletion of a genetic region that is associated with propagation of the virus, preferably a functional deletion in the NS3/NS3a gene region. In another embodiment, the ssRNA or cDNA encode chimeric genes of a variety of immunologically important regions from a number of different viral serotypes, whereby one of the ssRNA or cDNA comprises a functional deletion of a genetic region that is associated with propagation of the virus, preferably a functional deletion in the NS3/NS3a gene region. A resultant rescued, chimeric, propagation-competent strain of a mutant Reoviridae virus may then be used as a vaccine that protects against a number of different viral serotypes. A preferred combination of serotypes, or chimeric viruses, comprises AHSV and EEV serotypes, or EHDV and BTV serotypes.

Said cell preferably is a eukaryotic cell that can easily be infected and/or transfected using standard methods known to the skilled person. These cells include, for example, yeast cells and chicken fibroblast cells. Said eukaryotic cell preferably is an insect cell or a mammalian cell. Suitable insect cells comprise, for example, ovarian *Spodoptera frugiperda* cells such as Sf9 and Sf21, Kenyon cells of the *Culicoides* species *C. variipennis* (KC cells), *Drosophila* Schneider 2 cells, and *Aedes albopictus* C6/36 cells. Suitable mammalian cells comprise, for example, Baby Hamster Kidney cells such as BHK-21, Human Embryonic Kidney cells such as HEK293, VERO cells, MDCK cells, CHO cells, HuH-7, HeLa, SW13 and PER.C6 cells (Fallaux, F. J. et al. 1998. Hum Gene Ther 9: 1909-1917). A preferred cell is BHK-21, most preferred a BSR subclone of BHK-21 cells (Sato M, et al. 1977. Arch Virol 54: 333-343).

Said mutant virus preferably comprises a functional deletion, preferably a mutation, in the NS3 and NS3a (indicated as NS3/NS3a) coding region on segment 10 of Orbivirus. Said mutation is, for example a point mutation, two or more point mutations, or a single nucleotide deletion, that is introduced to mutate the putative amino acid sequence of translated NS3/NS3a proteins, or to abrogate the expression of NS3/NS3a proteins or of large C-terminal parts of the translated protein. For example, point mutations are introduced in recognized motifs within NS3/NS3a, like the late domain (LD), the N-terminally located trans membrane region (TM1), the conserved glycosylation site (GLN) between TM1 and TM2 (see FIG. 1). A further preferred mutation comprises the mutation of a putative start codon, or the introduction of a premature stop codon resulting in C-terminally truncated NS3/NS3a. A further preferred mutation comprises the mutation of the putative start codons of both NS3 and NS3a. A most preferred functional deletion is a deletion in a region of segment 10 that encodes NS3 and NS3a glycoproteins.

A preferred mutant Orbivirus comprising a functional deletion in the NS3/NS3a coding region on segment 10 of Orbivirus, preferably has retained the first 4 codons of NS3 following the first start codon, more preferred the first 6 codons of NS3 between the first ATG (NS3) and the second ATG (NS3a), more preferred the first 7 codons of NS3 between the first ATG (NS3) and the second ATG (NS3a) and thus not including the first ATG (NS3). These sequences are highly conserved and may be required for effective selection and/or packaging of segment 10 into a Orbivirus particle. Said mutant Orbivirus not necessarily comprises the first ATG (NS3) or the first ATG (NS3) and second ATG (NS3a), as it was found that a propagation competent virus could be rescued in which the first ATG, or the first and the second ATG, were altered.

The term NS3/NS3a, as used herein, refers to non-structural N-linked glycosylated membrane associated proteins that influence the release of virus particles from a target host or vector cell. Many other reoviruses encode glycosylated and/or membrane associated proteins, however, for most of the genera within the Reoviridae family the function of viral proteins is fairly unknown (http://www.reoviridae.org/dsRNA_virus_proteins/protein-comparison.htm).

Likely, the Orbivirus NS3/NS3a protein corresponds in function to that of similar glycosylated and/or membrane associated proteins in other reoviruses, for example NSp4 of Rotavirus, or p10 of avian Orthoreovirus-coding region.

A preferred mutant Reoviridae virus according to the invention comprises a deletion in a gene encoding NS3 and NS3a glycoproteins. This gene is located on segment 10 of Orbivirus. Said deletion preferably does not include 5'-untranslated nucleotides of segment 10 (thus upstream from the AUG start codon of NS3), more preferred the deletion does not include 5'-untranslated nucleotides with respect to NS3a (thus upstream of the putative AUG start codon of NS3a). In addition, said deletion preferably does not include the final 10 nucleotides, more preferred the final 20 nucleotides, more preferred does not include all untranslated nucleotides following the stop codon of NS3/NS3a at the 3'-end of the genomic segment.

A preferred deletion comprises a deletion of at least 20 nucleotides, more preferred at least 50 nucleotides, more preferred at least 100 nucleotides, more preferred at least 200 nucleotides, more preferred at least 300 nucleotides, more preferred at least 400 nucleotides, more preferred at least 500 nucleotides, of the genomic segment, whereby the deletion does not include the 5' and 3' inverted terminal repeats of the genomic segment. As is indicated hereinabove, the term deletion encompasses the replacement of nucleotide sequences by removal of nucleotide sequences from segment 10 and insertion of nucleotide sequences not from segment 10.

Said genomic segment preferably is or corresponds to segment 10 of Orbivirus. The term "corresponds to segment 10 of Orbivirus" is meant to indicate that said segment encodes NS3/NS3a, similar to segment 10 of Orbivirus. The corresponding segment, for example, is segment 11 of Aquareovirus or segment 10 of rotavirus.

The invention further provides a propagation-competent strain of a mutant Reoviridae virus that is obtainable by a method according to the invention. It was found that a propagation-competent strain of a mutant Reoviridae virus, preferably a Reoviridae virus comprising a deletion of a genetic region that is relevant for propagation of the virus, that is obtainable by the method according to the invention is characterized by an insertion of nucleotide sequences in the genomic segment that comprises said deletion. Said inserted nucleotide sequences are preferably inserted genomic nucleotide sequences from a genomic segment of the virus, preferably from a genomic segment that differs from the genomic segment that comprises said deletion of a genetic region that is relevant for propagation of the virus.

Said propagation-competent strain preferably is an Orbivirus, more preferably a Bluetongue virus or an African horse sickness virus.

A propagation-competent strain of a mutant virus is preferably isolated from viral plaques, or by end point dilution. In general, isolation of said virus is not required, since other virus variants will be overgrown by the said mutant virus in non-complementing cells. Alternatively, a propagation-competent strain of a mutant virus is preferably rescued directly from cDNA clones by said methods.

The invention further provides a propagation-competent strain of a mutant Reoviridae virus, comprising a functional deletion of a genetic region that is relevant for propagation of the virus, preferably a functional deletion in a viroporin-encoding region, preferably a functional deletion in the NS3/NS3a coding region. Said functional deletion is either an insertion, a point mutation, or, preferably, two or more point mutations, or, more preferably, a deletion.

A preferred alteration comprises the alteration of start codons in the coding region of a viroporin-encoding region, preferably by altering AUG into GCC. A preferred functional deletion comprises the alteration of an ATG translational start codon of both NS3 and NS3a, or of corresponding proteins in other reoviruses. Said alteration preferably comprises the alteration of the ATG translational start codon of NS3 and NS3a, into the triplet "GCC". Yet a further preferred alteration comprises the introduction of premature stop codons in the coding region of the NS3/NS3a glycoprotein. A deletion preferably is a deletion of at least 20 nucleotides, more preferred at least 50 nucleotides, more preferred at least 100 nucleotides, more preferred at least 200 nucleotides, more preferred at least 300 nucleotides, more preferred at least 400 nucleotides, more preferred at least 500 nucleotides, in the coding region of the NS3/NS3a glycoprotein, whereby the deletion does not include the 5' and 3' inverted terminal repeats of the genomic segment comprising said genetic region. It is preferred that said genomic segment is or corresponds to segment 10 of Orbivirus. A further preferred alteration comprises a combination of two or more of the described alterations, for example the alteration of startcodons (AUG into GCC) in the coding region of a viroporin-encoding region, preferably NS3 and NS3a, combined with a deletion in the coding region of the NS3/NS3a glycoprotein.

Said propagation-competent strain of a mutant Reoviridae virus, preferably is an Orbivirus, more preferred Bluetongue virus or African horse sickness virus.

The functional deletion of a genetic region that is associated with propagation of the virus in said propagation-competent strain of a mutant Reoviridae virus, preferably a deletion in the coding region of the NS3/NS3a glycoprotein, is preferably compensated by a complementing genomic alteration, preferably an insertion of nucleotide sequences, preferably an insertion of genomic nucleotide sequences from a genomic segment of the virus. Said genomic nucleotide sequences preferably are from a segment that is not, or does not correspond to, the segment comprising the functional deletion. It is further preferred that the inserted genomic nucleotide sequences are in the same 5'-3' orientation compared to the genomic segment from which they are derived, and are inserted within the ORF encoding the viroporin, preferably NS3/NS3a. There is no need for providing an insertion that compensates for the length of the deleted region, or that ensures translation of the remaining part of the genetic region that is relevant for propagation of the virus, preferably a genetic region encoding NS3/NS3a. It is preferred that the length of the inserted genomic nucleotide sequences is more than 20 nucleotides, more preferred more than 50 nucleotides, most preferred more than 100 nucleotides. Said inserted genomic nucleotide sequences preferably has a pseudoknot secondary structure. The presence of a pseudoknot secondary structure can be predicted by methods known in the art, for example with the aid of the software program "Cylofold" (http://cylofold.abcc.ncifcrf.gov).

Preferred genomic insertions comprise genomic nucleotide sequences from Segment 1, Segment 2, Segment 6, Segment 8, and/or Segment 9 of Orbivirus, or from segments that correspond to Segment 1, Segment 2, Segment 6, Segment 8, and/or Segment 9 of Orbivirus.

A preferred propagation-competent strain according to the invention is stable for at least 10 passages, preferably in a non-complementing cell line. It was found that a propagation-competent strain of a mutant Reoviridae virus, after establishment in a non-complementing cell line, is stable and can be propagated without alteration for at least 10 passages, more preferred at least 15 passages, more preferred at least 20 passages, more preferred at least 50 passages. Genetic stability of a vaccine results in a low risk of reverting 'back to virulence', a term that is known by the skilled person, and is therefore an important safety element of a vaccine.

The invention further provides a composition, preferably a pharmaceutical composition, comprising a propagation-competent strain of a mutant Reoviridae virus according to the invention, or comprising isolated viral ssRNA or cDNA of the invention. Since isolated viral ssRNA or cDNA from Reoviridae viruses is infectious, it is possible to use this for vaccination of an animal. The ssRNA or cDNA can be introduced into a cell or cells of the animal in any suitable way, where it will be transcribed and translated. This will produce viral proteins and lead to the production of viral particles. However, since the function of a genetic region that is relevant for propagation of the virus is functionally deleted, the viral ssRNA or cDNA will not be able to produce a fully functional, propagation-competent virus particle. At most, the virus will be able to complete virus replication in the animal, depending on the identity of the gene that is mutated.

The invention further provides a vaccine, comprising the propagation-competent of a mutant Reoviridae virus, preferably Orbivirus, according to the invention and, preferably, a suitable pharmaceutically and/or veterinary acceptable excipient such as a carrier, adjuvant or vehicle. Said excipient, for example, comprises vitamins; sugars such as sucrose, lactose, D-mannose, D-fructose, and/or dextrose; amino acids such as, for example, glycerin and asparagine; inorganic salts such as, for example, sodium bicarbonate, aluminum hydroxide, benzethonium chloride, ammonium sulfate, magnesium sulfate, potassium phosphate, sodium phosphate, aluminum phosphate and aluminum potassium sulfate; micro crystalline cellulose, magnesium stearate, cellulose acetate phthalate, human serum albumin, fetal bovine serum, citric acid, iron ammonium citrate, peptone, bovine extract and/or gelatin.

The term 'vaccine" refers to a Reoviridae virus, preferably Orbivirus, ssRNA or cDNA that can be used for immunizing a host that is normally infected and affected by the parent wildtype Reoviridae virus. A vaccine virus is preferably used as a modified live virus (MLV), but can also be used as dead vaccine after inactivation of the virus. A vaccine virus is non-pathogenic, meaning that it does not cause the disease that is normally associated with the infection by wild type virus. The concept of vaccines is well known to those skilled in the art. For example, wild type viruses can be attenuated or inactivated so that vaccination results in a protective immune response without causing full blown disease symptoms. A host mounts an effective immune response against a vaccine, resulting in protection against subsequent exposure to the wild type virus. A vaccine may comprise one or more virus strains.

Said protection against wild type virus is characterized as a reduction of clinical disease, and/or a reduction of replication and/or propagation of wild type virus in the host. Regarding control or eradication of a disease, protection by vaccination is defined as reduction of onward spread of wild type virus by any transmission route, horizontally, vertically, and directly or indirectly. The time to onset of protection and long lasting protection are also part of the efficacy of a vaccine. Further, broad protection in case of different virus species or serotypes is also part of efficacy.

In general, protection is indirectly measured by determining a level of neutralizing antibodies. Noteworthy, efficacy is directly associated to the costs of vaccination. For example, lower efficacy of a vaccine results in higher costs by the need of boosting, re-vaccination, or vaccination for different (groups of) serotypes due to limited protection provided by the vaccine after application to an animal.

Safety of a vaccine is one of the most important aspects to be considered. The term 'safety element' of a vaccine is any property related to safety of the vaccine resulting in the overall safety of the vaccine. Reduction of disease, reduction of the severity of clinical signs, reduction of adverse effects, or reduction of undesired reactions by vaccination in general, are all safety elements of a vaccine. An example of a 'safety element' of a vaccine is the safety of the vaccine in animals normally or not normally the susceptible animals of wild type virus. Another example of a 'safety element' of the vaccine is the stability of the vaccine during storage, production, distribution and after combining with other vaccines or components, and after proper or improper use in animals. For example, a lower and/or shorter viremia after vaccination is considered as a reduction of the chance on onward transmission of vaccine virus. Diminishing propagation of a vaccine virus in the host as well as the absence of viral shedding reduces a risk of onward transmission to people or other susceptible animals.

A propagation-competent strain of a mutant Reoviridae virus, preferably an Orbivirus, comprising a functional deletion in a viroporin-coding region, preferably a functional deletion in a NS3/NS3a-coding region, has properties that can be used in a vaccine. For example, it is attenuated and does not cause disease, it causes less damages to the host tissue, it does not interfere with the production of interferon, it's transmission by Culicoides biting midges is strongly reduced or even absent as dissemination of the propagation-competent strain of a mutant Reoviridae virus to the saliva will be severely hampered, it replicates in a vaccinated animal, and shows greatly reduced or no viremia. In addition, a Reoviridae virus comprising a functional deletion of NS3/NS3a or corresponding glycoproteins, does not induce an immune response against NS3/NS3a. The genetic modification, i.e. the functional deletion of NS3/NS3a, is not on a serotype-determining genome segment. Hence, the applicability of a vaccine comprising said Reoviridae virus is open for other serotypes by reassortment, in which ssRNAs or cDNA originating from different viruses are combined. For example, if the virus is BTV, a set of 10 ssRNAs or cDNA can be used that comprises segments of attenuated BTV and segments of field virus. Preferably, the segments of field virus encode VP2 and VP5, which are the main characterizing proteins that determine a serotype of interest. The ssRNA or cDNA may further encode a variety of immunologically important proteins from a number of different viral serotypes. In addition, these ssRNA or cDNA may encode chimeric genes of a variety of immunologically important regions from a number of different viral serotypes.

In addition, NS3/NS3a is involved in virus release from mammalian cells. Infection of animals with a virus that lacks NS3/NS3a or corresponding proteins results in a very low viremia. This reduced amount of virus in blood of an infected animal will result in reduced uptake of such virus by midges, and thus infection of midges and subsequent transmission of a virus that lacks NS3/NS3a. Further, virus release is particularly reduced from KC cells, as is clearly shown in the examples, suggesting that virus secretion in saliva will be strongly reduced as well. This may hamper or even eliminate onward transmission (spread) of the vaccine to susceptible hosts. It is considered likely that transmission of a mutant Reoviridae virus, preferably an Orbivirus, comprising a functional deletion in NS3/NS3a, by midges will be blocked. Thus, spread of such a mutant Reoviridae virus is limited to the primarily immunized host. A vaccine comprising such mutant Reoviridae virus is hereby defined as a Disabled Infectious Single Animal (DISA) vaccine.

A further preferred vaccine is a Differentiating Infected animals from Vaccinated Animals (DIVA) vaccine. Infection by a Reoviridae virus, preferably an Orbivirus, is characterized by seroconversion, which is the development of detectable specific antibodies against said Reoviridae virus in the blood serum as a result of the infection. Seroconversion remains for a longer period of time than antigen. However, it varies for each of the immunogenic proteins in, for example BTV. In BTV, the humoral immune response is mainly directed against structural proteins VP7 and VP2, but antibodies are also raised against NS3/NS3a. VP7 is highly conserved and the antibody response represents the orbivirus serogroup, whereas VP2 represents the serotype of the orbivirus serogroup. Commercial ELISAs for Orbivirus infections are based on the detection of serogroup specific VP7-antibodies. These ELISAs are available for BTV, AHSV, and EHDV and detect infection as early as 7-10 days post infection. Neutralizing antibodies are mainly directed against the outer shell protein VP2 and are specific for each serotype. Serum neutralizing tests (SNTs) detect serotype specific neutralizing antibodies in sera, and thus distinguish between the neutralizing responses against serotypes. Further, the titer of neutralizing antibodies is correlated with protection.

NS3/NS3a protein is a third antigen of Orbivirus but is less immunogenic. Still, antibodies directed against NS3/NS3a can be easily detected after infection (Barros et al., 2009. Vet Microbiol 137, 252-259; Laviada, 1995. Virus Res 38: 205-218). However, knowledge about the response against NS3/NS3a is very limited. For example, all known amino acid sequences of NS3/NS3a of BTV are compared in order to map conserved regions. Although recognized motifs, like the late domain (LD), the N-terminally located trans membrane region (TM1) and the conserved glycosylation site (GLN) between TM1 and TM2 (see FIG. 1) are highly conserved between serogroups, the overall amino acid sequence of NS3/NS3a is highly conserved within each serogroup, but differs between serogroups. This suggests that the immune response induced by NS3/NS3a might be cross-reactive within each serogroup, and might be specific for each serogroup.

A propagation-competent strain of a mutant Reoviridae virus, preferably an Orbivirus, comprising a functional deletion of NS3/NS3a or corresponding proteins, has properties that can be used in a DIVA vaccine. For example, vaccination with such mutant Reoviridae virus, inactivated or not, will result in a normal immune response, except that no antibodies against NS3/NS3a or corresponding proteins are raised. In contrast, field strains will also induce antibodies directed against NS3/NS3a or corresponding proteins, including conserved antigenic regions on NS3/NS3a. Consequently, ELISAs as published (Barros et al., 2009. Vet Microbiol 137, 252-259; Laviada, et al., 1995. Virus Res 38: 205-218) or other serological assays based on the humoral response against NS3/NS3a or corresponding proteins can differentiate between infected animals and animals vaccinated with vaccines that lack NS3/NS3a or corresponding proteins (serological DIVA). For BTV, the humoral response against NS3/NS3a or corresponding proteins is detectable for up to 5 months post natural infection. Importantly, this is longer than the infectious period after natural infection by BTV.

The present invention further provides a method for vaccinating an animal against a Reoviridae virus, comprising administering an effective amount of a propagation-competent strain of a mutant Reoviridae virus according to the invention to the animal. The skilled person will realize that also administration, preferably injection, of isolated ssRNA or cDNA that provide the genomic segments of the mutant Reoviridae virus can similarly be used in a method for vaccinating an animal against a Reoviridae virus.

The animal to be vaccinated will vary depending on the identity of the Reoviridae virus and the particular animals that it infects. For example, if the virus is AHSV or EEV, the animal is selected from equine species, like horses, mules, donkeys and zebras. If the virus is EHDV or BTV, the animal is selected from ruminant species, like deer, cattle, sheep or goat.

The pharmaceutical composition comprising a vaccine virus, isolated viral ssRNA, or cDNA of this invention may be administered orally, parenterally, or by inhalation, or other routes. Oral administration can be performed in any orally acceptable dosage form including, but not limited to, capsules, tablets, and aqueous suspensions and solutions. In the case of tablets for oral use, carriers which are commonly used include lactose and corn starch. Lubricating agents, such as magnesium stearate, are also typically added. For oral administration in a capsule form, useful diluents include lactose and dried corn starch.

Preferably the vaccine virus, inactivated or not, isolated viral ssRNA or cDNA is administered parenterally, preferably by injection. The vaccine virus, inactivated or not, isolated viral ssRNA or cDNA according to the invention is preferably formulated with conventional, non-toxic pharmaceutically-acceptable carriers, adjuvants or vehicles. The term parenteral, as used herein, includes subcutaneous, intracutaneous, intravenous, intramuscular, intra-articular, intrasynovial, intrasternal, intrathecal, intralesional and intracranial injection or infusion techniques. A most preferred administration route is subcutaneous injection.

The vaccine virus, inactivated or not, viral ssRNA or cDNA is preferably in the form of an injectable preparation, for example, an injectable aqueous or oleaginous suspension. This suspension may be formulated according to techniques known in the art using suitable dispersing or wetting agents (such as, for example, Tween 80) and suspending agents. The injectable preparation may also be an injectable solution or suspension in a non-toxic parenterally-acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or a similar alcohol as described in the Pharmacopoea Helvetica.

The amount of vaccine virus of the invention that is administered to an animal is, in general, in the range of 1,000 to 1,000,000,000 infectious virus particles per ml. The amount of infectious particles can be determined using standard techniques known to the skilled person such as, for example, a dose response curve.

FIGURE LEGENDS

FIG. 1 Schematic representation of NS3/NS3a

NS3/NS3a protein contains several recognized domains, from N- to C-terminus; two Calpactin p11 binding domains, late domain motif (LD) binds to Tsg101, two trans membrane regions (TM1 and TM2) with a conserved glycosylation sites in-between (NLG149), and a VP2 binding domain.

Figure 2:
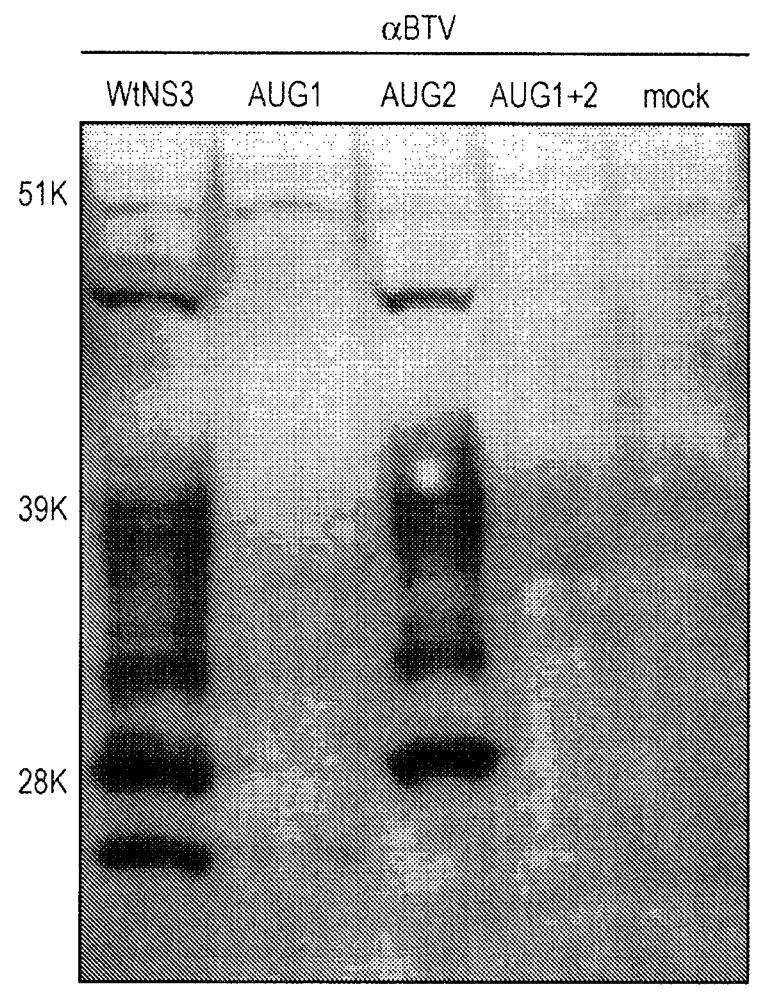

FIG. 2 Western blotting of (mutant) NS3/NS3a proteins. BSR cells were infected with wtBTV (lane 1), mut AUG-1 (lane 2), mut AUG-2 (lane 3), mut AUG-1+2 (lane 4), and mock infected cells (lane 5). Proteins of concentrated lysates were separated by polyacrylamide gelelectrophoresis and were transferred by blotting. Proteins were immunostained with serum from a diseased sheep (Backx et al., 2007. Vet Rec 161: 591-592). The putative molecular weights (MW) of the expressed NS3/NS3a protein(s) are indicated by the mobility of MW markers.

Figure 3:
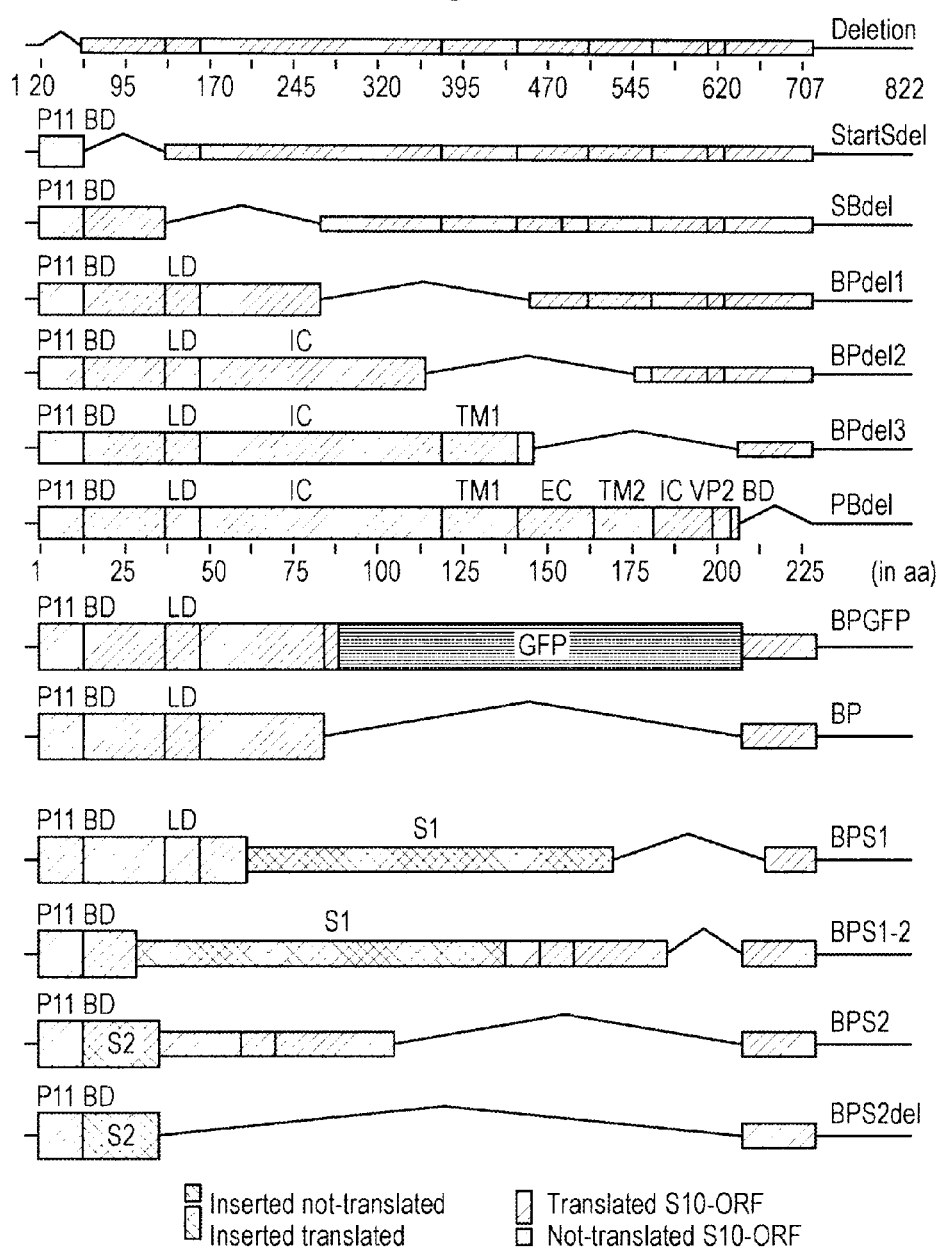

FIG. 3 Overview of BTV mutants and BTV revertants S10 genome segments of stocks of rescued BTV mutants were completely sequenced. No virus was rescued with genome segments 'Deletion', BPGFP and BP. Origin of sequences are indicated, rgBTV8 (dark grey), rgBTV1 (medium grey) and GFP (light grey). The genome segment is indicated for inserted sequences originating from genome segments S1 and S2, respectively.

FIG. 4 Production of modBTvac-1 in BSR cells

A. Top Panel

BSR monolayers were infected in duplicate with modBTvac-1 or rgBTV1 at 0.1 MOI. At indicated time points, virus titres were determined by endpoint dilution, expressed in TCID50/ml, and plotted at a logarithmic scale. The bars represent the average of two replicates.

B. Middle Panel

Dilutions of virus stocks of rgBTV1, BTV(S10-25), and modBTvac-1 were analyzed by panBTV PCR assays targeting genome segment S1 and S10. BTV(S10-25) contains S10 with the ORF of NS3/NS3a of BTV25. This sequence contains one mismatching nucleotide in the center of the reverse primer of the S10-based panBTV PCR assay. modBTvac-1 contains two mismatching nucleotides at the 5'-end of the reverse primer. The maximum dilution detected by each of the panPCR tests was plotted for indicated viruses.

C. Lower Panel

Monolayers of BSR- and KC cells were infected with modBTvac-1 or rgBTV1 at 0.1 MOI. At indicated time points, samples of supernatant and cell lysate were prepared, and the virus titer was determined by endpoint dilution. The bars represent the relative virus release in the supernatant at the indicated time points.

FIG. 5

A. Daily rectal body temperatures are presented. Infections are indicated by arrows B. Clinical signs were monitored on indicated days. Infections are indicated by arrows.

C. Viremia was measured by S10 panBTV PCR assay. Infections are indicated by arrows.

D. Seroconversion was determined by VP7-ELISA, and is presented as (100−x) %. Infections are indicated by arrows.

FIG. 6

Dilutions of serum samples were tested by VP7-ELISA (VP7-ELISA) and by SNT for neutralizing Ab titres (nAbs) against BTV serotype 1 (BTV1-VNT) for sera of 21 dpi, 42 dpi, and 63 dpi with rgBTV1. The highest dilution tested positive is indicated to quantitate the titer of VP7-directed Abs. Threshold value of the VP7-ELISA was set at 50%, meaning >50% blocking is interpreted as positive and <50% as negative.

FIG. 7

Vaccination—BTV8 challenge. Vaccination and BTV8 challenge are indicated by arrows at 0 dpv and 21 dpv, respectively. A. Mean daily rectal temperatures per group are presented. B. Total clinical signs were monitored and calculated per group on indicated days. C and D. Mean viremia was measured by S1 and S10 panBTV PCR assays. E. Mean seroconversion was determined by VP7-ELISA, and is presented as (100−x) %, with a threshold value set at 50%. F. Serum neutralizing antibodies were determined against BTV8 for sera collected on 0 dpv, 21 dpv and 42 dpv. G. Mean seroconversion was determined by NS3-ELISA, and is presented as (100−x) % with a threshold value set on 50%.

FIG. 8

Dose response. Vaccinations are indicated by arrows. Only groups H were revaccinated at 21 dpv. A. Mean viremia was determined by S1 panBTV PCR assay. B. Mean seroconversion was determined by VP7-ELISA, and is presented as (100−x) % with a threshold value set on 50%.

FIG. 9

Serotype specific protection and differentiating infected from vaccinated animals (DIVA). Two groups of four sheep were vaccinated twice with BT DISA (rgBTV6 with Seg-2 of serotype 8 and the NS3/NS3a knockout phenotype) with an interval of three weeks (DISA DISA). Two groups of four sheep served as control groups (BTV2 and BTV8, respectively). At 84 dpv (arrow), sheep were challenged with BTV2 or BTV8 (DISA DISA BTV2 and DISA DISA BTV8, respectively).

Sheep were monitored from one week before to three weeks after challenge (78 dpv/−6 dpc to 105 dpv/21 dpc). A. Mean daily rectal temperatures per group are presented. B. Total clinical signs were monitored and calculated per group on indicated days. C. Mean viremia was determined by S1 panBTV PCR assay. D. Mean seroconversion was determined by VP7-ELISA, and is presented as (100−x) % with a threshold value set at 50%. E and F. Serum neutralizing antibodies against BTV2 or BTV8, respectively, were determined for sera collected on 0 dpv, 21 dpv, 42 dpv, 84 dpv and 105 dpv. G. Mean seroconversion was determined by NS3-ELISA, and is presented as (100−x) % with a threshold value set at 50%.

FIG. 10

Hydrophobicity plot of NS3/NS3a protein. Hydrophilic EC region is flanked by high hydrophobic regions TMR1 and TMR2 between position 117-183.

FIG. 11

Expression and purification of truncated NS3 antigen (BTV8)NS3ΔTM. Fractions were separated by polyacrylamide gel electrophoresis and proteins were detected by standardized Coomassie Brilliant Blue staining.

FIG. 12

Figure 12:
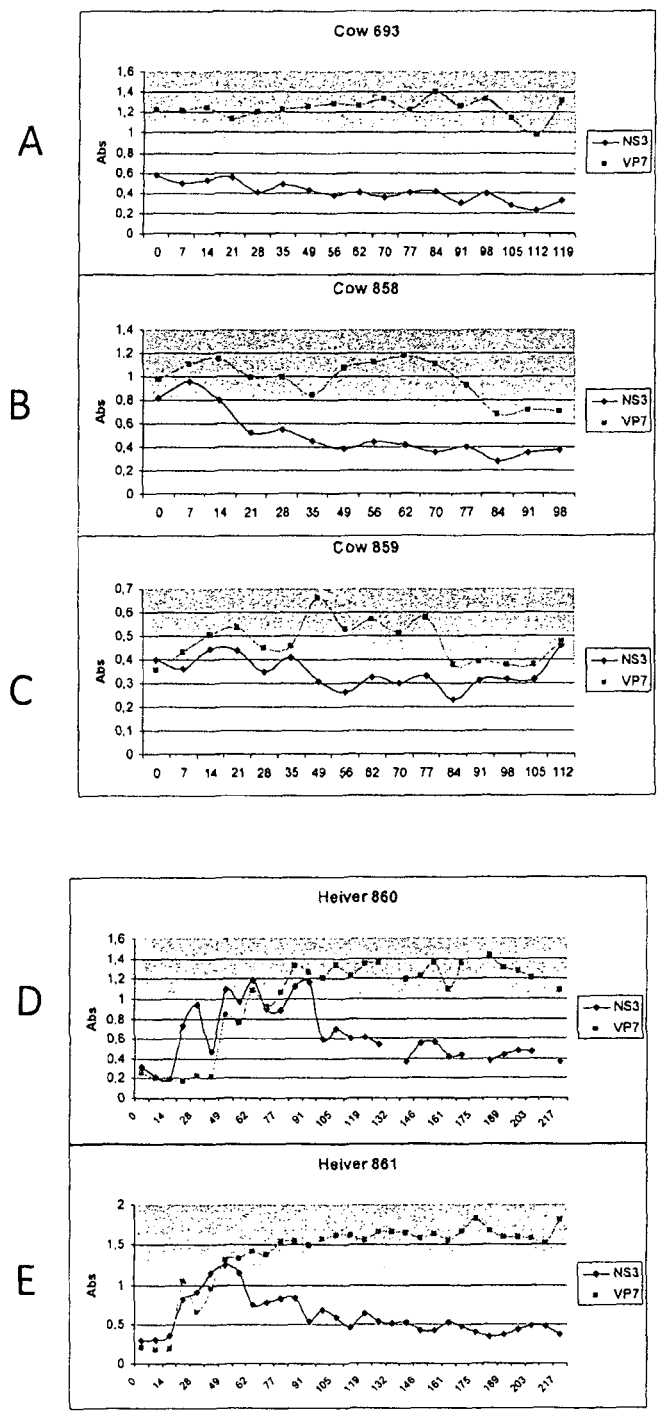

FIG. 12A ELISA of sera from Cow 693: VP7 positive for >170 dpi. NS3 positive for >135 dpi. The VP7-Ab titer in high.

FIG. 12B ELISA of sera from Cow 858: VP7 positive for >150 dpi. NS3 positive for >130 dpi.

FIG. 12C ELISA of sera from Cow 859: VP7 positive fort 130 dpi. NS3 positive for ±80 dpi. The VP7-Ab titer in low.

FIG. 12D ELISA of sera from Heifer 860: NS3-Abs are detected earlier than VP7-Abs. NS3-Abs are declining after 100 dpi, and convert to doubtful/negative after appr. 5 month post infection.

FIG. 12E ELISA of sera from Heifer 861: NS3-Abs are detected earlier than VP7-Abs. NS3-Abs are declining after 70 dpi, and convert to doubtful/negative after appr. 5 month post infection.

EXAMPLES

General
Cell Lines

BSR cells, a clone of BHK-21 cells; gift from Polly Roy (Sato et al., 1977. Arch Virol 54, 333-343), and BHK-21 (baby hamster kidney) were cultured in Dulbecco's modified Eagle's medium (DMEM; Invitrogen) containing 5% fetal bovine serum (FBS) and 100 IU/ml penicillin, 100 µg/ml streptomycin and 2.5 ug/ml Amphotericin B.

Vero (African green monkey kidney epithelial) cells were cultured in Dulbecco's modified Eagle's medium (DMEM; Invitrogen) containing 5% fetal bovine serum (FBS) and 100 IU/ml penicillin, 100 µg/ml streptomycin and 2.5 ug/ml Amphotericin B.

KC cells (Kenyon cells of the *Culicoides* species *C. variipennis*; gift from Linda McHolland were grown in modified Schneider's *Drosophila* medium with 15% heat inactivated foetal bovine serum, and 100 IU/ml penicillin, 100 µg/ml streptomycin and 2.5 ug/ml Amphotericin (Wechsler et al., 1989. J Invertebr Pathol 54, 385-393).

Except for BTV8/net06, BTV8/net07, BTV6/net08, and AHSV4LP, all BTVs and related orbiviruses of the following serogroups—African horse sickness virus (AHSV), Epizootic hemorrhagic disease virus (EHDV), and Equine encephalosis virus (EEV)—were purchased from the Pirbright Institute, Pirbright, UK, and then passed once in BHK-21 cells according to standard procedures. BTV8/net06, BTV8/net07 and BTV6/net08 were isolated in The Netherlands in 2006, 2007 and 2008, respectively (www.i-ah.bbsrc.ac.uk/dsRNA_virus_proteins/ReoID/viruses-at-iah.htm), see below. AHSV4LP was obtained from Dr. Christiaan Potgieter, Deltamune, South Africa (Erasmus B J. 1973. Proceedings of the third International Conference of Equine Infectious Diseases. p1-11). BTV8/net07 was isolated from the Holstein Frisian cow NL441689187 from Bavel, the Netherlands, which was sampled for export purposes on Jul. 24, 2007 (van Gennip et al., 2012. PLoS ONE 7, e30540). Isolation from EDTA-blood was performed on embryonated eggs (e1) and subsequent three passages on BHK-21 cells (e1/bhk3) or subsequent three passages on KC cells (e1/kc3). BTV6/net08 was isolated from the Holstein Frisian cow NL415834681 (Oct. 24, 2008) from Heeten, the Netherlands (van Rijn et al., 2012. Vet Microbiol 158, 23-32). Isolation from EDTA-blood was performed on eggs and subsequent three passages on BHK-21 cells and once on BSR cells.

All virus stocks were obtained by infection of BSR cells at low multiplicity of infection (MOI) and harvested after 100% cytopathic effect (CPE) was observed. Virus titers were determined by endpoint dilution and expressed as 50% Tissue cell infective dose per ml (TCID50/ml) (Gard and Kirkland, 1993. Australian standard diagnostic techniques for animal diseases, 1-17). Viral stocks were stored at −80° C.

Monoclonal antibody (MAb) ATCC1875 was obtained from the American Tissue Cell Collection (ATCC). MAbs 33H7, 32H2, 32F1, 31E9 and 32B6, directed against NS3, were supplied by Ingenasa, Spain. Peptide serum against a part of BTV-VP5 was commercially obtained and was a generous gift from Michiel Harmsen, CVI-Lelystad. BTV reference sera raised against 24 reference BTV strains and against proposed BTV26 were kindly obtained from the Pirbright Institute, Pirbright, UK. Other BTV sera were obtained from sheep or cattle naturally or experimentally infected by BTV8/net06 or BTV6/net08 (Backx et al., 2007. Vet Rec 161, 591-592; van Gennip et al., 2012a. PLoS ONE 7, e30540; van Gennip et al., 2012b. PLoS ONE 7, e44619; van Rijn et al., 2012. Vet Microbiol 158, 23-32), or from animal trials described below.

Virus isolation was carried out on embryonated chicken eggs (ECE) or by passages on monolayers of BHK-21, Vero, or KC cells according to standard procedures for orbiviruses. After one passage on ECE, homogenates were prepared and passed in BHK21, Vero, or KC cells. Homogenates and cell passages were tested by the panBTV PCR test or other appropriate PCR assays, as described below.

Embryonated egg-isolated BTV8/net07/e1, cell-culture derived BTV8/net07/e1/bhk3, BTV8/net07/e1/kc3, BTV6/net08/e1/bhk3/bsr2 and AHSV4LP were completely sequenced after one extra passage on BSR cells by use of an improved strategy for sequence-independent amplification of segmented dsRNA viral genomes and pyrophosphate-based 454 (Roche GS20/FLX) sequencing at the Inqaba Biotec company, South Africa (Potgieter et al., 2009. J Gen Virol 90, 1423-1432). Sequence analysis was essentially done as described by use of Lasergene8 from DNASTAR (Potgieter et al., 2009. J Gen Virol 90, 1423-1432). Files containing the sequence information, quality values and flowgrams (sff files) were loaded into the Seqman 8 program of the Lasergene software. Contig sequences of BTV8 strains were assembled and checked manually. Sequences were compared to sequences of BTV-8nt (2006/04) (Maan et al., 2008. Virology 377, 308-318) with GenBank accession numbers AM498051-AM498060) and to sequences of BTV8/Neth2006 with GenBank accession numbers FJ183374-FJ183383 for S1-S10, respectively.

Consensus sequences of BTV8 directly isolated from EDTA-blood were determined after RNA-isolation using the TRIZOL method, and reverse transcription and amplification by a one-tube system (Qiagen one-step RT-PCR kit). Overlapping DNA amplicons were sequenced using Big-Dye® Terminator v1.1 Cycle Sequencing Kit in a ABI PRISM® 3130 Genetic Analyzer Applied Biosystems.

Contig sequences of BTV6/net08 were checked manually and compared to sequences of BTV6/Net2008/05 with GenBank accession numbers QG506472-QG506481 (Maan et al., 2008. Virology 377, 308-318). Contig sequences of AHSV4LP were checked manually.

Sequence analysis was essentially done with software programs of Lasergene 8 or 10 from DNASTAR or DSgene, like predicted translation and alignment. Predictions of RNA structures and higher order RNA structures like hairpins and pseudoknots were studied by use of the software program "Cylofold" (http://cylofold.abcc.ncifcrf.gov/).

cDNA of genome segments were synthesized by Genscript Corporation (Piscataway, N.J.). Genome segments S1-S10 of BTV1 were based on the sequences as submitted to GenBank with accession numbers FJ969719-FJ969728. Genome segments S1-S10 of BTV8/net07 and of BTV6/net08 were based on the consensus sequences as described (van Gennip et al., 2012a. PLoS ONE 7, e30540). Genome segments S1-S10 of AHSV4LP were based on the consensus sequences as determined. cDNAs were cloned in commercially available pUC-derivatives, pUC18, 19 or 57, or pJET1.2 (BioRad) under control of the T7 RNA-polymerase promoter and a recognition site for a restriction enzyme (RE) at the 3'-terminus for defined run-off transcription as described (van Gennip et al., 2012a. PLoS ONE 7, e30540). Another set of plasmids with cDNAs of all genome segments of BTV6/net08 were flanked by T7 RNA-polymerase at the 5'-end and the sequence of the RIBOzyme of hepatitis delta virus (HDV) at the 3'-terminus, respectively. Another set of mammalian expression plasmids with ORFs of genome segments were flanked by the early promoter of human cytomegalovirus and a polyA-signal at the 3-' terminus, respectively, as described (van Rijn et al., 1994. J Virol 68, 3934). Commercially available plasmid pET-51(+) Ek/LIC (Millipore) was used for bacterial expression of NS3 originating from BTV8/net06. Plasmids were maintained in *E. coli* DH5a, and were purified using the QIAfilter Plasmid Midi Kit (Qiagen).

Plasmid DNA was digested at the 3'-terminus with the respective restriction enzyme, and was purified by standard procedures. One µg of digested plasmid DNA was used for in vitro RNA run-off transcription with 5'-cap analogue using the MESSAGE mMACHINE T7 Ultra Kit (Ambion). In this reaction, a ratio of 4:1 of anti-reverse cap analogue to rGTP was used. Synthesized RNA was purified by use of MEGAclear columns (Ambion) according to the manufacturer's instructions, and eluted RNA was stored at −80° C.

For all generated viruses, a proper virus stock was used for further analyses. Several passages of rescued BTV by use of 'improved GMS2' were analysed in more detail. In particular, the entire sequence of the mutated genome segment was checked.

RNA of virus stocks was isolated and genome segments of S1, S2, S7, S10 for BTV, and S4 and S5 for AHSV were identified by different PCR assays, see PCR testing below.

To discriminate between the genome segments of different viruses, amplicons of diagnostic PCR tests were sequenced by use of the BigDye® Terminator v3.1 Cycle Sequencing Kit in a ABI PRISM® 3130 Genetic Analyzer (both supplied by Applied Biosystems, Foster City, Iowa, USA) as described (van Rijn et al., 2012a). Alternatively, amplicons of PCR tests were digested with specific restriction enzymes and analyzed by 0.9% agarose gel electrophoresis and visualized under UV light after staining with ethidium bromide, see S10 genotyping as an example (van Gennip et al., 2012a. PLoS ONE 7, e30540).

Infected BSR monolayers were prepared with indicated (mutant) Orbiviruses by use of the generated virus stocks. Infected monolayers were used for immunoperoxidase monolayer assay (IPMA) with MAbs and sera, and plaque formation assays. Alternatively, cell lysates or cell culture supernatants were used for Western blotting and other common methods. All these methods were performed according to standard procedures well-known to skilled persons.

BSR monolayers were infected with indicated (mutant) Orbiviruses by use of the generated virus stocks. To study cytopathic effect (CPE), BSR monolayers were infected by tenfold dilutions of indicated viruses, and grown for two days under overlay medium (EMEM complete with 1% methylcellulose). Monolayers were fixed with methanol/aceton (1:1) and immunostained with appropriate MAb, e.g. for BTV with ATCC1875. Plaque sizes of appropriate dilutions of viruses were compared.

For analysis of virus growth, confluent BSR-monolayers in M24-well plates were infected in duplicate at a multiplicity of infection (moi) of 0.1. After attachment to cells for 1.5 h at 37° C., the medium was removed and refreshed with 1 ml of DMEM with 5% FBS, 100 IU/ml penicillin, 100 µg/ml streptomycin and 2.5 ug/ml Amphotericin B and incubation was continued. At indicated time points in hours post infection (hpi), samples were harvested and stored at −80° C. Virus titers were determined by titration on BSR cells and expressed as TCID50/ml (Gard and Kirkland, 1993. Australian standard diagnostic techniques for animal diseases, 1-17). Alternatively, other cell lines like KC cells were used to study virus replication kinetics. In more detail, cells and cell culture supernatants were harvested separately to study relative virus release from cells.

For PCR testing, blood samples, organ samples or cell cultures were tested by the panBTV PCR test as described (van Rijn et al., 2012. J Vet Diagn Invest 24: 469). Briefly, viral RNA was isolated by an automated procedure with the High Pure Viral RNA kit (Roche). For EDTA blood, 100 µl of sample diluted with PBS (1:1) was used. For virus stocks, viral RNA was isolated from 200 µl virus stock or supernatant. RNA was eluted in 50 µl of RNase-free $H_2O$. Genome segments of S1, S2, S10 were detected by real time PCR assays. In some cases, amplicons were sequenced to identify the origin of the respective genome segment. Genome segments S7 and S10 were also identified by full genome amplification followed by sequencing.

For panBTV PCR assays, a first reaction consisted of 0.25 µM of forward and reverse primer, 0.25 µM of the probe, 2.75 mM of $MnCl_2$, 7.5 µl of a commercial master mix (Roche), and 5 µl of RNA in a total volume of 20 µl. Thermocycling conditions were: 20 sec at 98° C., 20 min at 61° C., 30 sec at 95° C., 40×(1 sec at 95° C., 10 sec at 61° C., 15 sec at 72° C.), followed by 30 sec at 40° C., and storage at 4° C. Initial denaturation of dsRNA, first strand complementary DNA (cDNA) synthesis (RT), PCR, and real-time monitoring were performed in a closed capillary. Real-time RT-PCR was performed using a thermal cycler. Amplification was monitored in real time by the ratio of the $OD_{530}$ and $OD_{640}$ ($OD_{530}/OD_{640}$) using commercially available LC software (Roche). A PCR test was considered valid if all negative controls were negative and positive controls were positive. In case of an invalid PCR test, the entire set of isolated RNA was tested again. A representative isolation run of 32 samples contained 6 controls resulting in a final capacity of 26 test samples per isolation run. Three negative controls (which consisted of 200 µl of PBS) and 3 positive controls were part of each isolation run. Positive controls contained different dilutions of BTV grown on BHK-21 cells.

The weak positive control (cut-off value) contained the highest dilution of virus with a reproducible positive signal. The strong positive control was the highest dilution of virus resulting in a maximal ratio of optical density $(OD)_{530}/OD_{640}$. The third positive control (intermediate control) was a dilution of virus with a result between the weak and strong positive control. Results were evaluated as positive, doubtful, or negative according to van Rijn et al., 2012 (van Rijn et al., 2012. J Vet Diagn Invest 24: 469).

For full genome amplification of genome segments S7 and S10, template RNA (6 µl) was denaturated at 94° C. for 3 min and immediately cooled on ice. A one-step RT-PCR kit (Qiagen) was used to reverse transcribe RNA and amplification of cDNA in a RT-PCR containing both primers. The reaction mix contained 10 µl of 5×QIAGEN one-step RT-PCR buffer, 2 µl of dNTP mix, 0.6 µM of each primer and 2 µl of the enzyme mix (containing RT and PCR reaction enzymes). RNase-free water was added to a total volume of 44 µl. Six microliters of denatured RNA was added to the mix. The RNA was reverse transcribed at 45° C. for 30 min. This was followed by an activation step at 94° C. for 15 min. Forty amplification cycles were then carried out (94° C. for 1 min, 45° C. for 1 min and 72° C. for 2 min), followed by a terminal extension step at 72° C. for 10 min. The cDNA products were analysed by 0.9% agarose gel electrophoresis and visualized under UV light after staining with Ethidium Bromide.

Primers and probe for panBTV PCR test targeting genome segment S1 of BTV are:

```
F-panS1:
                                    (SEQ ID NO: 1)
5'-TTAAAATGCAATGGTCGCAATC R-panS1:
                                    (SEQ ID NO: 2)
5'-TCCGGATCAAGTTCACTCC P-panS1:
                                    (SEQ ID NO: 3)
5'-CCGTGCAAGGTGC
```

Sequences are indicated in the 5'→3' order. F, R, and P indicate forward primer, reverse primer, and probe, respectively. The probe is labeled with FAM at the 5'-end, and with the MGB at the 3'-end (Toussaint et al., 2007. J Virol Methods 140, 115-123).

PCR primers for amplification of entire genome segment S7 of BTV are:

```
F-panS7/01:
                                    (SEQ ID NO: 4)
GTTAAAAATCTATAGAGATG R-panS7/02:
                                    (SEQ ID NO: 5)
GTAAGTGTAATCTAAGAGA F-panS7/03:
                                    (SEQ ID NO: 6)
GTTAAAAAATCGTTCAAGATG R-panS7/04:
                                    (SEQ ID NO: 7)
GTAAGTTTAAATCGCAAGACG
```

Sequences are indicated in the 5'→3' order. F and R indicate forward primer and reverse primer.

PCR primers and probe for panBTV PCR test targeting genome segment S10 of BTV are:

```
F-panS10:
                                    (SEQ ID NO: 8)
AGTGTCGCTGCCATGCTATC R-panS10:
                                    (SEQ ID NO: 9)
GCGTACGATGCGAATGCA P-panS10:
                                   (SEQ ID NO: 10)
CGAACCTTTGGATCAGCCCGGA
```

Sequences are indicated in the 5'→3' order. F, R, and P indicate forward primer, reverse primer, and probe, respectively. The probe is labeled with FAM at the 5'-end, and with the quencher TAMRA at the 3'-end.

PCR primers for amplification of entire genome segment S10 of BTV are:

```
F-panS10:
                                          (SEQ ID NO: 11)
GTTAAAAAGTGTCGCTGCCATG R-panS10:
                                          (SEQ ID NO: 12)
GTAAGTGTGTAGTGTCGCGCAC
```

Sequences are indicated in the 5'→3' order. F and R indicate forward primer and reverse primer.

PCR primers and probe for panAHSV PCR test targeting genome segment S4 of AHSV are:

```
F-panS4:
                                          (SEQ ID NO: 13)
TTAGGATGGAACCTTACGC R-panS4:
                                          (SEQ ID NO: 14)
ATTCTGCCCCTCTCTAACCA P-panS4:
                                          (SEQ ID NO: 15)
CTTTGAGTAGGTATTCGATCTCCTGCG
```

Sequences are indicated in the 5'→3' order. F, R, and P indicate forward primer, reverse primer, and probe, respectively. The probe is labeled with FAM at the 5'-end, and with the black hole quencher (BHQ) at the 3'-end.

PCR primers and probe for panAHSV PCR test targeting genome segment S5 of AHSV are:

```
F-panS5:
                                          (SEQ ID NO: 16)
CGCAATCTTCGGATGTAAGC R-panS5:
                                          (SEQ ID NO: 17)
GCACACTACCTTGGATCTCTG P-panS5:
                                          (SEQ ID NO: 18)
TCGCCA + TCC + TCA + TCATCG
```

Sequences are indicated in the 5'→3' order. F, R, and P indicate forward primer, reverse primer, and probe, respectively. + indicates a Locked Nucleotide Acid (LNA). The probe is labeled with FAM at the 5'-end, and with the black hole quencher (BHQ) at the 3'-end.

A real-time PCR test for BTV has been developed in-house (van Rijn et al., 2012. J Vet Diagn Invest 24: 469). Here, the S10-based amplicons of PCR positives were sequenced (S10 genotyping). Briefly, amplified material was separated by agarose-gelelectrophoresis and purified by standard procedures. Amplicons were sequenced with forward and reverse primers by using the BigDye® Terminator v1.1 Cycle Sequencing Kit in a ABI PRISM® 3130 Genetic Analyzer (both supplied by Applied Biosystems, Foster City, Iowa, USA). Sequences were subject to BLAST-N analysis (NCBI). Alternatively, amplicons were digested with restriction enzymes specific for amplicons originating from BTV6 or BTV8, respectively (van Gennip et al., 2012b. PLoS ONE 7, e44619).

Serotype-specific real-time PCR tests targeting genome segment 2 (S2) were developed for serotypes 1, 6 and 8 (S2 genotyping). Genetic material was isolated according to the procedures described for the panBTV-PCR test (van Rijn et al., 2012. J Vet Diagn Invest 24: 469). 5 µl aliquots from one RNA extraction (50 µl) were used for all real-time PCR tests. Selected PCR primers and probes for the different S2 genotyping tests are listed below. S2 genotyping was performed according to the all-in-one method as described (van Rijn et al., 2012a. Vet Microbiol 158, 23-32). One reaction consists of 0.5 µM of the forward and reverse primer, 0.5 µM probe, 2.75 mM Mn-Acetate, 7.5 µl reaction mix, and 5 µl RNA in a total volume of 20 µl. Thermo-cycling conditions of the PCR test were: 20 sec., 98° C., 20 min. 61° C., 30 sec., 95° C., 40×(1 sec., 95° C., 10 sec., 57° C., 15 sec, 72° C.) followed by 30 sec. at 40° C., and storage at 4° C. Amplification was monitored real-time by $OD_{530}/OD_{640}$ using the Light Cycler software, version 4.05 (Roche). The selectivity/specificity of primers was investigated with orbiviruses of the CV1 collection consisting of reference panels of BTV, African horse sickness virus, epizootic hemorrhagic disease virus, equine encephalosis virus, and a limited number of additional BTV isolates. The diagnostic sensitivity was compared with the panBTV-PCR test with previously S10 genotyped EDTA-blood samples.

Alternatively, amplified material was separated by agarose-gelelectrophoresis and purified by standard procedures. Amplicons were sequenced with forward and reverse primers by using the BigDye® Terminator v1.1 Cycle Sequencing Kit in a ABI PRISM® 3130 Genetic Analyzer (both supplied by Applied Biosystems, Foster City, Iowa, USA). Sequences were subject to BLAST-N analysis (NCBI).

PCR primers and probes for serotype specific real time PCR tests targeting genome segment 2 of BTV serotype 1, 6, and 8 are:

```
BTV-serotype 1
F1:
                                          (SEQ ID NO: 19)
TTGTTGAAAGTACGAGACACAAGAG R1:
                                          (SEQ ID NO: 20)
GTATCAGCCTTCTTTGAATCGATT P1:
                                          (SEQ ID NO: 21)
CATCCACTGCACCCACTGGTCA BTV-serotype 6
F6:
                                          (SEQ ID NO: 22)
AGGAACAGTCGGCTTATCAC R6:
                                          (SEQ ID NO: 23)
TTCGCTAATGTGCTTCTCCAT P6:
                                          (SEQ ID NO: 24)
TTGTCAGCTTTACGCAAACCCCG BTV-serotype 8
F8:
                                          (SEQ ID NO: 25)
CGGAGACAGCGCAGTATGTA R8:
                                          (SEQ ID NO: 26)
CCTCGGTAGTATCCCTCACG P8:
                                          (SEQ ID NO: 27)
ACATACGATGCCYTCGGAGGATTCTG
```

Sequences are indicated in the 5'→3' order. F, R, and P indicate forward primer, reverse primer, and probe, respectively. Probes are labeled with FAM at the 5'-end, and with the black hole quencher (BHQ) at the 3'-end.

Example 1

This example describes the generation of (mutant) bluetongue viruses (BTVs), and (mutant) African horsesickness viruses (AHSVs), virus species of the genus orbivirus within the family of Reoviridae by use of reverse genetics combined with recombinant DNA technology known as genetic modification systems (GMS). Reassorted orbivirus and mutant orbiviruses were generated by different genetic modification systems, all methods are well-known to a skilled person and have been described (Trask et al., 2012. Methods 59: 199-206), here named GMS1 (van Gennip et al., 2010. Virol J 7, 261), and GMS2 (Boyce et al., 2008. J Virol 81, 2179-2186; van Gennip et al., 2012. PLoS ONE 7, e30540), In addition, GMS3 and GMS4 were used to generate (mutant) orbiviruses (here described). Further, GMS2 was significantly improved (Improved GMS2) in order to rescue less fit BTV that did not show CPE for which immunostaining appeared to be crucial, and in order to rescue BTV revertants after several passages of transfected cells and or cell culture supernatants of these transfected/passed cells.

GMS1: Incorporation of one synthetic RNA or mutated RNA was performed by transfection of this synthetic RNA to infected BSR monolayers followed by screening of uptake of this RNA by several well-known methods. As an example, genome segments S7 or S10 of BTV8/net06 was incorporated in BTV6/net08 (van Gennip et al., 2010. Virol J 7, 261). Note that no selection was performed and that therefore sequential rounds of uptake of one or more synthetic RNAs could be performed. Ultimately, after up to 10 rounds, one by one every RNA genome segment could have a synthetic ancestor and consequently, complete synthetic BTV could be generated by GMS1. Indeed, almost every single segment reassortant could be generated, demonstrating that each synthetic RNA can be incorporated one by one (van Gennip et al., 2012a. PLoS ONE 7, e30540). Note that several synthetic RNAs contain silent mutations. Thus, it was demonstrated that by use of mutated synthetic RNA, genetic modifications in any genome segment of interest can be incorporated.

For GSM1, genome segments S7 and S10 were synthesized by Genscript Corporation (Piscataway, N.J.) based on the identical sequences AM498057.2 and FJ183380.1 (GenBank) for S7, and the identical sequences AM498060.1 and FJ183383.1 (GenBank) for S10. cDNAs were cloned in plasmid pUC57 under control of the DNA-dependent T7 RNA-polymerase promoter and a site for a restriction enzyme (RE) at the 3'-terminus for defined run-off transcription (see below).

Plasmid DNA was digested with restriction enzyme BbsI for S7 or with BsMBI for S10, and was purified by standard procedures. One μg of digested plasmid DNA was used for in vitro RNA run-off transcription with 5' cap analogue using the MESSAGE mMACHINE T7 Ultra Kit (Ambion). In this reaction, a ratio of 4:1 of anti-reverse cap analogue to rGTP was used. Synthesized RNA was cleaned by use of MEGA-clear columns (Ambion) according to the manufacturer's instructions, and eluted RNA was stored at −80° C.

Monolayers of $10^5$ BSR cells were infected at a multiplicity of infection (MOI) of 0.1 with BTV6/net08. At one hour post infection (hpi), infected monolayers were transfected with 400 ng synthesized RNA transcripts of S7 or S10 using 1 μl Lipofectamine™ 2000 (1:2.5; 1 mg/ml, Invitrogen) in Opti-MEM® 1 Reduced Serum Medium according to manufacturer's conditions for 4 hrs, after which it was refreshed with 1 ml of Dulbecco's Modified Eagle Medium (DMEM) supplemented with 5% FBS and 100 IU/ml penicillin, 100 μg/ml streptomycin and 2.5 ug/ml Amphotericin B. At 40 hpi, supernatants were harvested, and virus was cloned by endpoint dilution in M96-wells on BSR cells. At 3 days post infection (dpi), supernatants were collected from wells with cells developing cytopathogenic effect (CPE). Infection of the respective monolayers was confirmed by immunostaining with monoclonal antibody (MAb) produced by ATCC-CRL-1875 directed against VP7 (MAb ATCC1875). Viruses in supernatants were multiplied in M24 wells in BSR cells by adding 75 μl supernatant in 1 ml of DMEM supplemented with 5% FBS and 1% of Penicillin/Streptomycin/Fungizone. After development of CPE, 2-3 dpi, supernatants were collected and stored at −80° C.

Example 2 (GMS2)

A complete set of 10 synthetic RNAs was used. In a first transfection, 6 out of 10 RNAs were used for transfection to BSR monolayers, after 18 hours a second transfection to the same monolayers was performed with all 10 RNAs. Every virus generated by this method will contain the set of 10 RNAs. As an example, recently isolated BTVs, BTV8/net06 and BTV6/net08 were regenerated by this method (van Gennip et al., 2012a. PLoS ONE 7, e30540). Regenerated virus (rgBTV) was detected and differentiated by the presence of synonymous or 'silent' mutations with respect to encoded amino acid sequence. Further, virulence and non-virulence of rgBTV8 and rgBTV6, respectively, were confirmed by experimental infection of sheep (van Gennip et al., 2012a. PLoS ONE 7, e30540). In addition, many BTV mutants and BTV reassortants were generated (Celma and Roy, 2011. Journal of Virology 85, 4783-4791; Ratinier et al., 2011. PLoS Pathog 7, e1002477; van Gennip et al., 2012b. PLoS ONE 7, e44619).

For GMS2, monolayers of $10^5$ BSR cells per 2 cm² were transfected with equimolar amounts of RNA of BTV genome segments S1 [VP1], S3 [VP3], S4 [VP4], S5 [NS1], S8 [NS2], and S9 [VP6]. In total, 600 ng RNA was transfected using 1 μg Lipofectamine™ 2000 (1:2.5; 1 mg/ml, Invitrogen) in Opti-MEM® I Reduced Serum Medium according to manufacturer's conditions. Eighteen to 20 hours post transfection, monolayers were transfected again with 600 ng equimolar amounts of a complete set of ten different RNA segments S1-S10. At 4 hrs post transfection, the transfection mix was replaced with 1 ml DMEM supplemented with 5% FBS and 1% of Penicillin/Streptomycin/Fungizone. Supernatants were harvested from monolayers developing cytopathogenic effect (CPE) at 48 hrs after the $2^{nd}$ transfection. BTV specific CPE was confirmed by immunostaining of fixed monolayers with monoclonal antibody (MAb) produced by ATCC1875 directed against VP7 according to standard procedures (van Gennip et al., 2012a. PLoS ONE 7, e30540; van Gennip et al., 2012b. PLoS ONE 7, e44619).

Example 3 (Improved GSM2)

According to the method of example 2. However, if no visible CPE was formed after 2-3 days post transfection (e.g. due to a reduced transfection efficiency), cells of duplicate wells were passed 1:5 to rescue virus. After incubation for another three days, monolayers were screened for CPE and VP7 expression as described above. In some cases, despite the absence of visible CPE, groups of cells of the transfected monolayer were immunostained by VP7-Ab ATCC1875. Then, supernatants were passed by infection of fresh BSR monolayers to rescue the respective BTV. In many cases, sequential passages of transfected cells and/or supernatants were performed to rescue BTV, BTV mutants, or BTV revertants.

Example 4 (GMS3)

The set of plasmids containing cDNAs of all genome segments of BTV6/net08 flanked by a DNA-dependent T7 RNA-polymerase and RIBOzyme were used to rescue 'synthetic' BTV6/net08. In the sequence of cDNA encoding genome segment S2, a LguI site was mutated to a NaIV site for differentiation purposes (van Gennip et al., 2012b. PLoS ONE 7, e44619). Plasmids were purified as described above. Monolayers of $10^5$ BSR-T7 cells per 2 cm$^2$ were infected by Fowlpox virus expressing T7 RNA-polymerase (Britton et al., 1996. J Gen Virol 77 (Pt 5), 963-967) with a MOI of 0.01. After 1.5 hours, in total 600 ng DNA in equimolar amounts was transfected using 1.5 µg Lipofectamine™ 2000 (1:2.5; 1 mg/ml, Invitrogen) in Opti-MEM® I Reduced Serum Medium according to manufacturer's conditions. The procedure was continued as described above for RNA transfection. Alternatively, in total 600 ng DNA in equimolar amounts was transfected, and 18 hours later transfection of DNA was repeated together with infection of Fowlpox virus T7. Again, the procedure was continued as described.

Example 5 (GMS4)

For rescue of 'synthetic' AHSV4LP, monolayers of $10^5$ BSR cells per 2 cm$^2$ were transfected with equimolar amounts of mammalian expression plasmids for AHSV segments encoding VP1 (S1), VP3 (S3), VP4 (S4), VP6 S9), VP7 (S7), NS1 (S5), and NS2 (S8). In total, 300 ng DNA was transfected using 1.5 µg Lipofectamine™ 2000 (1:2.5; 1 mg/ml, Invitrogen) in Opti-MEM® I Reduced Serum Medium according to manufacturer's conditions. Twenty-four hours post transfection, monolayers were transfected again with 600 ng equimolar amounts of 10 AHSV-RNA segments according to GMS2 (van Gennip et al., 2012b. PLoS ONE 7, e44619). Supernatants were harvested from monolayers at 48 hours after the $2^{nd}$ transfection. Cells of these monolayers were passed 1:5 according to 'improved GMS2'. Then, monolayers were screened for CPE, as described. If no visible CPE was present, supernatants were used to infect fresh monolayers to pass rescued AHSV. In the absence of obvious CPE, sequential passages of transfected cells and/or supernatants were performed to rescue AHSV, AHSV mutants, or AHSV revertants. Minimal requirements for GMS4 (rescue of 'synthetic' AHSV4LP) were determined using expression plasmids with AHSV genes optimized for expression in BHK21 cells and stability in E. coli, as is depicted in Table A.

TABLE A

Expression of VP1, VP3 and NS2 from optimized genes are essential for virus rescue in combination with capped RNAs in the second transfection.

| expression plasmids | | virus rescue | |
|---|---|---|---|
| * | RNAs | CPE | IPMA |
| all 7 | capped | + | + |
| −VP1 | capped | − | − |
| −VP3 | capped | − | − |
| −VP4 | capped | + | + |
| −VP6 | capped | + | + |

TABLE A-continued

Expression of VP1, VP3 and NS2 from optimized genes are essential for virus rescue in combination with capped RNAs in the second transfection.

| expression plasmids | | virus rescue | |
|---|---|---|---|
| * | RNAs | CPE | IPMA |
| −VP7 | capped | + | + |
| −NS1 | capped | + | + |
| −NS2 | capped | − | − |
| −NS1, −VP7 | capped | + | + |
| VP1, VP3, NS2 | capped | + | + |
| all 7 | uncapped | + | + |
| −VP4 | uncapped | − | − |
| −VP6 | uncapped | − | − |
| −VP7 | uncapped | − | − |
| −NS1 | uncapped | + | + |
| VP1, VP3, NS2 | uncapped | − | − |

* 300 ng in total, all optimized
Except for NS1, all expression plasmids are needed when uncapped RNAs were used. Virus rescue was determined by induction of CPE and confirmed by IPMA.

Example 6

Previously, it has been shown that GMS2 was not successful for some mutations. The authors had used in trans complementation to rescue and propagate BTV mutants containing lethal mutations like large deletions in genome segment S9 or small deletions in genome segment S10 (Celma and Roy, 2011. J Virol 85, 4783-4791; Matsuo and Roy, 2009. J Virol 83, 8842-8848). Here, we have rescued BTV with mutations that were assumed to be lethal according to GMS2. Therefore, transfected BSR monolayers without visible CPE were passed in 1:5 dilutions and in some cases, additional passages of transfected cells were performed to rescue BTV mutants. Further, transfected BSR monolayers were immunostained with BTV-specific MAb in order to screen for BTV mutants that did not cause CPE (see example 3). An overview of the mutations is provided in Table 1.

BTV with mutated start codons in NS3/NS3a (mut AUG1+2) was rescued. This BTV mutant showed significantly reduced CPE, and could have been missed without immunostaining. After rescue by improved GMS2, this double AUG-mutant virus appeared genetically stable, and replicated in normal cells. Thus, in trans complementation of NS3 or NS3a by a cell line is not needed. Immunostaining as well as westernblot analysis confirmed the absence of both NS3 and NS3a proteins (FIG. 2). From these results, it can be concluded that NS3/NS3a protein is not essential for BTV replication in BSR cells.

BTV with small insertions in S10 (filled-in StyI and filled-in BsiWI sites) resulting in an out-of-frame insertion were rescued after several passages. Here, detailed studies showed that additional changes were introduced during cell passages. These additional changes restored the NS3/NS3a expression by deletion of the inserted nucleotides. Apparently, a strong selection pressure for NS3/NS3a expression resulted in these NS3/NS3a revertants. Passaging transfected cells played a crucial role to select these revertants, since by GMS2 these revertants were not found (not shown).

BTV with large deletions in S10 were rescued after several (up to seven) passages. Here, detailed studies showed that viruses comprising insertions of RNA sequences from other genomic segments in S10 were positively selected by cell passages. Apparently, a strong selection for the uptake/insertion of these RNA sequences resulted in the isolation of these BTV mutants. Again, passing transfected cells played a crucial role to select these viable mutants with insertions. Indeed, use of in vitro RNA based on S10 with the observed insertions resulted in efficient rescue by GMS2, and no extra passages were needed to isolate this virus and to prepare a virus stock.

TABLE 1

Rescue of BTV mutants by use of improved GMS2.

| S10 mutation | virus rescue by GMS2 | virus rescue by improved GMS2 | additional changes |
|---|---|---|---|
| Mut AUG1 + 2 | No | Yes* | No |
| Mut-A | No | No | No |
| 'deletion' | No | No | No |
| StyI filled | No | Yes | point deletion |
| BsiWI filled | No | Yes | point deletion |
| BP | No | Yes | insertion |
| BPGFP | No | Yes | deletion + insertion |

Attempts to rescue BTV with indicated S10 genome segments by use of GMS2 was not successful (No). Mut AUG1 + 2 was likely not rescued by GMS2 because the virus shows reduce efficiency and does not induce visible CPE. Mutant AUG1 + 2 does not contain additional changes in S10, but was rescued by improved GMS2 (Yes*). Mut-A and 'deletion' were not rescued, even not after several attempts by use of improved GMS2 (No). Other rescued BTV mutants contained additional changes as indicated and are therefore named revertants (Yes). All mutations and additional changes as observed in several revertants are presented elsewhere in more detail.

Example 7

Small mutations (point mutations, small insertions) were introduced in genome segments to mutate the putative amino acid sequence of translated proteins, or to abrogate the expression of large C-terminal parts of the translated protein (see Tables 2 and 3). Here, genome S10[NS3/NS3a] was targeted, but other genome segments, e.g segment 2 of BTV6 and BTV8, have also been targeted (van Gennip et al., 2012a. PLoS ONE 7, e30540).

Point mutations were made in genome segment S10 encoding recognized motifs of NS3/NS3a, like the late domain (LD), the N-terminally located trans membrane region (TM1), the conserved glycosylation site (GLN) between both TM regions and a stop codon at the 3' end was introduced resulting in C-terminal truncated NS3/NS3a according to Celma and Roy, 2009. J Virol 83, 6806-6816. Further, silent mutations in highly conserved regions in the ORF were introduced (Mut-B). BTV1 mutants were rescued as efficient as rgBTV1 and virus stocks were prepared, except for Mut-B. Sequence analyses confirmed the presence of the introduced mutations, and no other changes were detected in genome segment S10.

The restriction site for StyI and BsiWI in cDNA of genome segment S10 were digested, filled-in, and re-ligated resulting in a 4-basepairs insertion.

Consequently, the ORF of NS3/NS3a was interrupted and putative translation will be terminated shortly after the 4-basepairs insertion. BTV1 mutants were rescued by use of improved GMS2. Finally, virus stocks were prepared. Sequence analyses showed an additional point deletion that restored the ORF resulting in an overall insertion of one codon. In all studied mutants, the ORF of NS3/NS3a was restored by a point deletion in the vicinity of the 4-basepairs insertion. The additional point deletion was not necessarily the same in independently rescued revertants. The virus stocks were used for further analysis, and no other changes were detected in genome segment S10.

TABLE 2

The sequences of the region with mutations in several motifs of S10 [NS3/NS3a] are presented.

| Late domain (LD) (PPRYAPSAP) | | | | | | | | | | |
|---|---|---|---|---|---|---|---|---|---|---|
| Mutant | P | P | R | Y | A | P | S | A | P | virus rescue |
| wild type: | 124--/CCA.CCA.AGG.TAT.GCT.CCG.AGT.GCA.CCG./-- | | | | | | | | (SEQ ID NO: 28) | Yes |
|  | 36--/Pro.Pro.Arg.Tyr.Ala.Pro.Ser.Ala.Pro./-- | | | | | | | | (SEQ ID NO: 29) | |
| NS3-ASAP: | 124--/CCA.CCA.AGG.TAT.GCT.<u>GCA</u>.AGT.GCA.CCG./-- | | | | | | | | (SEQ ID NO: 30) | Yes |
|  | 36--/Pro.Pro.Arg.Tyr.Ala.<u>Ala</u>.Ser.Ala.Pro./-- | | | | | | | | (SEQ ID NO: 31) | |
| NS3-GAAP: | 124--/CCA.CCA.AGG.TAT.GCT.<u>GGA.GCA</u>.GCA.CCG./-- | | | | | | | | (SEQ ID NO: 32) | Yes |
|  | 36--/Pro.Pro.Arg.Tyr.Ala.<u>Gly.Ala</u>.Ala.Pro./-- | | | | | | | | (SEQ ID NO: 33) | |

| Reverse primer | | | | | | | |
|---|---|---|---|---|---|---|---|
| Mutant | A | A | F | A | S | Y | A | virus rescue |
| wild type: | 245--/.GCT.GCA.TTC.GCA.TCG.TAC.GCG./-- | | | | | | (SEQ ID NO: 34) | Yes |
|  | 82--/.Ala.Ala.Phe.Ala.Ser.Tyr.Ala./-- | | | | | | (SEQ ID NO: 35) | |
| Mut-B: | 245--/.GC<u>A</u>.GC<u>T</u>.TT<u>T</u>.GC<u>T</u>.<u>AGC</u>.T<u>A</u>T.GCG./-- | | | | | | (SEQ ID NO: 36) | Yes |
|  | 82--/.Ala.Ala.Phe.Ala.Ser.Tyr.Ala./-- | | | | | | (SEQ ID NO: 35) | |

| Transmembrane region (TM1) | |
|---|---|
| Mutant | virus rescue |
| wild type: 410--/.GTG.GTT.GCG.CTG.TTG.ACA.TCA.GTT./-- | (SEQ ID NO: 37) Yes |
| --/.Val.Val.Ala.Leu.Leu.Thr.Ser.Val./-- | (SEQ ID NO: 38) |
| TM1 ALL ->EEE: 410--/.GTG.GTT.GAA.GAG.GAA.ACA.TCA.GTT./-- | (SEQ ID NO: 39) Yes |
| --/.Val.Val.Asp.Asp.Asp.Thr.Ser.Val./-- | (SEQ ID NO: 41) |

TABLE 2-continued

The sequences of the region with mutations in several motifs of S10 [NS3/NS3a] are presented.

Glycosylation site (GLN)

| Mutant | N G T | | virus rescue |
|---|---|---|---|
| wild type: | 463--/.AAG.ATA.AAT.GGA.ACT.AAA./-- <br> Asn.Gly.Thr. | (SEQ ID NO: 42) | Yes |
| NS3-N149S: | 463--/.AAG.ATA.TCG.GGA.ACT.AAA./-- <br> Ser.Gly.Thr | (SEQ ID NO: 44) | Yes |

C-terminal stop

| Mutant | | | virus rescue |
|---|---|---|---|
| Wild type: | 644--/.GTG.AGG.ATG.AGT.TTT.ACG.GAG./-- <br> 209--/.Val.Arg.Met.Arg.Phe.Thr.Asp./-- | (SEQ ID NO: 46) <br> (SEQ ID NO: 48) | Yes |
| CT4stop 212: | 644--/.GTG.AGG.ATG.TGA.TTT.ACG.GAG./-- <br> 209--/.Val.Arg.Met.STP.Phe.Thr.Asp./-- | (SEQ ID NO: 49) <br> (residues 1 to 3 of SEQ ID NO: 48 and residues 5 to 7 of SEQ ID NO: 48) | Yes |

Mutations (double underlined) and changed amino acids (underlined) are indicated. Virus rescue is indicated by 'Yes' or 'No'. Entire S10 genome segments of virus stocks were sequenced and no additional changes were found.

TABLE 3

Sequences of the regions with additional changes in the vicinity of the 4-basepairs insertions in S10[NS3/NS3a] resulting in repair of NS3/NS3a expression and virus rescue.

StyI revertants

| Wild type: | 124--/CCAC----CAAGGTATGCTCCGAGTGCACCGATGCCATCATCTATGCCAACGGTTGCCCTTGA/-- | (SEQ ID NO: 50) |
|---|---|---|
| | 36    P P ---- R Y A P S A P M P S S M P T V A L E/-- | (SEQ ID NO: 52) |
| StyI filled: | --/CCACCAAGCAAGGTATGCTCCGAGTGCACCGATGCCATCATCTATGCCAACGGITGCCCTTGA/-- | (SEQ ID NO: 53) |
| | 36    P P S K V C S E C T D A I I Y A N G C P * | (SEQ ID NO: 54) |
| S-rev-1: | 124--/CCACCA-GCAAGGTATGCTCCGAGTGCACCGATGCCA/-- | (SEQ ID NO: 55) |
| | 36    P P A R Y A P S A P M P /-- | (SEQ ID NO: 56) |
| S-rev-2: | 124--/-CACCAAGCAAGGTATGCTCCGAGTGCACCGATGCCA/-- | (SEQ ID NO: 57) |
| | 36    H Q A R Y A P S A P M P /-- | (SEQ ID NO: 58) |

BsiWI revertant

| wild type: | 242--/AAGGCTGCATTCGCATCGTAC----GCGGAAGCGTTTCGTGA/-- | (SEQ ID NO: 59) |
|---|---|---|
| | 81    K A A F A S Y ---- A E A F R D/-- | (SEQ ID NO: 61) |
| BsiWI filled: | 242--/AAGGCTGCATTCGCATCGTACGTACGCGGAAGCGTTTCGTGA/-- | (SEQ ID NO: 62) |
| | 81    K A A F A S Y V R G S V S * | (SEQ ID NO: 63) |
| B-rev-1: | 242--/AAGGCTGCATTCGCATCGTACGTA-GCGGAAGCGTTTCGTGA/-- | (SEQ ID NO: 64) |
| | 81    K A A F A S Y V A E A F R D/-- | (SEQ ID NO: 66) |

Entire S10 genome segments of virus stocks were sequenced. The 4-basepairs insertions and additional point deletions are double underlined. No other nucleotide changes were found. Amino acid changes compared to the wild type sequence are underlined. No virus could be isolated without additional point deletions, indicating a strong selection pressure for (mutant) NS3/NS3a expression.

Example 8

Start codons of NS3 and NS3a were mutated (AUG-→GCC) in cDNA of genome segment S10 as previously described (Celma and Roy, 2011. J Virol: 85, 4783-4791). Here, these AUG→GCC mutations were combined for BTV. Further, the region between both AUG start codons was deleted ('deletion'), or silent mutations were introduced in this region (Mut-A). These mutated S10 genome segments were used for virus rescue by improved GMS2. Despite several attempts, Mut-A and 'Deletion' were not rescued (not shown). Stocks of BTV with AUG mutations (AUG mutant viruses) were prepared, and AUG→GCC mutations were confirmed by sequencing. The virus stocks were used for further analysis, and no other changes were detected in genome segment S10.

| Mutant | AUG1 | AUG2 |
|---|---|---| wild type

GTTAAAAAGTGTCGCTGCC.ATG.CTA.TCC.GGG.CTG.ATC.CAA.AGG.TTC.GAA.GAA.GAA.AAA.ATG  (SEQ ID NO: 67)

Mut AUG1

GTTAAAAAGTGTCGCTGCC.<u>GCC</u>.CTA.TCC.GGG.CTG.ATC.CAA.AGG.TTC.GAA.GAA.GAA.AAA.ATG  (SEQ ID NO: 69)

Mut AUG2

GTTAAAAAGTGTCGCTGCC.ATG.CTA.TCC.GGG.CTG.ATC.CAA.AGG.TTC.GAA.GAA.GAA.AAA.<u>GCC</u>  (SEQ ID NO: 71)

Mut AUG1 + 2

GTTAAAAAGTGTCGCTGCC.<u>GCC</u>.CTA.TCC.GGG.CTG.ATC.CAA.AGG.TTC.GAA.GAA.GAA.AAA.<u>GCC</u>  (SEQ ID NO: 73)

Mut-A

GTTAAAAAGTGTCGCTGCC.ATG.CTA.TC<u>G</u>.GG<u>C</u>.<u>T</u>TA.AT<u>A</u>.CA<u>G</u>.AG<u>A</u>.TT<u>T</u>.GAA.GAA.GAA.AAA.ATG  (SEQ ID NO: 75)

Deletion

GTTAAAAAGTGTCGCTGCC.----.---.---.---.---.---.---.---.---.---.---.---.ATG  (SEQ ID NO: 77)

List of mutations in the 5'-terminal part of S10 tested for virus rescue. Positions of start codons are indicated (AUG1 and AUG2), and mutated start codons in cDNAs are underlined. Point mutations (silent mutations) are double underlined.

BTV rescue of BTV with mutations in the 5'-terminal part of S10. In case of failure, several attempts were undertaken to rescue BTV mutants. Virus rescue of Mut-A was not successful (No). Mutant viruses with AUG→GCC mutations were generated (Yes). BSR monolayers were infected with AUG mutant viruses and immunostained with MAb ATCC1875 against VP7, or Ab directed against NS3/NS3a. Immunostaining was positive (+), negative (−), or not done (nd).

| BTV mutant | virus rescue | VP7 staining | NS3 staining |
|---|---|---|---|
| Wild type | Yes | + | + |
| Mut AUG1 | Yes | + | + |
| Mut AUG2 | Yes | + | + |
| Mut AUG1 + 2 | Yes | + | − |
| Mut A | No | nd | nd |

Example 9

NS3/NS3a protein is not essential for BTV replication. Since rescue of BTV without S10 genomic RNA had failed (not shown), RNA sequences of genome segment S10 must be essential for virus replication. Here, RNA sequences in S10 were mapped that are important for virus replication. NTR sequences are highly conserved and are considered essential for virus replication. Therefore, the involvement of these sequences in BTV rescue were not further investigated. Several deletions in genome segment S10 were constructed and used in experiments to rescue BTV by use of GMS2.

In addition, attempts to rescue virus were expanded by improved GMS2 in order to find revertants compensating for the deletion of essential RNA sequences.

(SEQ ID NO: 78)
G$^{(1)}$TTAAAAAGTGTCGCTGCCATGCTATCCGGGCTGATCCAAAGGTTCG

AAGAAGAAAAAATGAAACATAATCAAGACAGAGTTGAAGAGCTGAGTCT

AGTACGTGTAGATGACACCATCTCTCAACCACCAAGGTATGCTCCGAGT

GCACCGATGCCATCATCTATGCCAACGGTTGCCCTTGAAATATTGGACA

AAGCGATGTCAAACACAACTGGTGCAACGCAAACACAAAAGGCGGAGAA

-continued

GGCTGCATTCGCATCGTACGCGGAAGCGTTTCGTGATGATGTAAGACTG

AGACAGATCAAGCGCCATGTGAACGAGCAGATTTTACCAAAATTAAAAA

GTGATCTAAGTGGATTGAAGAAGAAACGAGCAATCATACACACTACTCT

ATTAGTAGCGGCTGTGGTTGCGCTGTTGACATCAGTTTGTACCCTTTCA

AGCGATATGAGTGTGGCCTTTAAGATAAATGGAACTAAAACAGAAGTGC

CTTCATGGTTTAAAAGCCTTAACCCGATGCTTGGCGTGGTCAATTTGGG

AGCAACTTTTCTGATGATGGTTTGCGCAAAGAGTGAAAGAGCCTTGAAC

CAGCAGATAGATATGATAAAGAAGGAAGTGATGAAGAAACAATCTTATA

ATGATGCGGTGAGGATGAGTTTTACAGAGTTCTCGTCAGTCCCGCTGGA

TGGTTTCGAAATGCCATTAACCTGAGGACAGTAGGTAGAGTGGCGCCCC

GAGGTTTACGTCGTGCAGGGTGGTTGACCTCGCGGCGTAGACTCCCACT

GCTGTATAACGGGGAGGGTGCGCGACACTACACACTTAC$^{(822)}$ wild type (SEQ ID NO: 75)
GTTAAAAAGTGTCGCTGCC.ATG.CTA.TCC.GGG.CTG.ATC.CAA.
AGG.TTC.GAA.GAA.GAA.AAA.ATG.//--

Deletion (SEQ ID NO: 97)
GTTAAAAAGTGTCGCTGCC.----.---.---.---.---.---.
---.---.---.---.---.---.ATG.//--

'Deletion'. The sequence of the entire S10 genome segment of rgBTV(822 bases in length), including start codons (bold + underlined) and stop codon (underlined), is presented in the upper part. Sequence comparison of 'Deletion' and wtBTV. The presentation of the comparison of "Deletion" and wtBTV is limited to the 5'-terminal part of S10 (upper part). ORF (codons separated by dots), start codons (bold + underlined), and the deletion (--) in "Deletion" are indicated. Virus rescue was not successful for "Deletion", despite several attempts, despite the use of improved GMS2, and despite intact NTRs and ORF of NS3a.

BPdel (SEQ ID NO: 79)
G$^{(1)}$TTAAAAAGTGTCGCTGCCATGCTATCCGGGCTGATCCAAAGGTTCG

AAGAAGAAAAAATGAAACATAATCAAGACAGAGTTGAAGAGCTGAGTCT

-continued

AGTACGTGTAGATGACACCATCTCTCAACCACCAAGGTATGCTCCGAGT

GCACCGATGCCATCATCTATGCCAACGGTTGCCCTTGAAATATTGGACA

AAGCGATGTCAAACACAACTGGTGCAACGCAAACACAAAAGGCGGAGAA

GGCTGCATTCGCATCGTAC $^{(262)}$ T $^{(634)}$ AATGATGCGG<u>TGA</u>GGATGAGTTT

TACAGAGTTCTCGTCAGTCCCGCTGGATGGTTTCGAAATGCCATTAACC

TGAGGACAGTAGGTAGAGTGGCGCCCCGAGGTTTACGTCGTGCAGGGTG

GTTGACCTCGCGGCGTAGACTCCCACTGCTGTATAACGGGGAGGGTGC

GCGACACTACACACTTAC $^{(822)}$

BPdel. Sequence of S10 genome segment BPdel (451 bases in length), including start codons (bold + underlined) and stop codon (underlined). Virus rescue was not successful indicating that this deletion also contains an essential RNA sequence for virus rescue by GMS2. This deletion was used to rescue revertants by use of improved GMS2.

| S10 mutation | name revertant | virus rescue (GMS2) | virus rescue (improved GMS2) | additional changes |
|---|---|---|---|---|
| Deletion | — | No | No | nd |
| BPGFP | BPS1 | No | Yes | deletion + insertion |
| BP | BPS1-2 | No | Yes | insertion |
| BP | BPS2 | No | Yes | insertion |

Using GMS2, rescue of BTV mutants, of which BPGFP contained an insertion of the GFP gene, has failed. By use of improved GMS2, several BTV revertants were isolated, however, rescue of BTV with a small deletion between both start codons has failed again (Deletion). S10 genome segments of rescued BTV revertants were completely sequenced and contained additional changes with respect to the original genetic modification.

Since up to seven passages were needed for rescue of BTV revertants using improved GMS2. Positive selection and thus additional changes were supposed. Indeed, changes in length of the mutated S10 were shown by agarose gel electrophoresis during selection of revertants. Sequence analyses showed that rescued BTV revertants contain genetic changes with respect to the originally introduced genetic modifications. The complete sequence of these S10 genome segments were determined.

A revertant of BPGFP had a deletion of the entire GFP gene and flanking sequences, which were replaced by sequences originating from genome segment S1 (BPS1).

The deletion of the sequence between BsiWI and PsiI in BP was maintained in the revertants analysed, but insertions were found in other positions in S10. One of these has an insertion originating from genome segment S1 (BPS1-2). A second, independent revertant was isolated from the same experiments and contained an insertion of 68 nucleotides directly downstream from the 2$^{nd}$ start codon, which originated from genome segment S2 (BPS2).

(SEQ ID NO: 80)

G $^{(1)}$ TTAAAAAGTGTCGCTGCCATGCTATCCGGGCTGATCCAAAGGTTCGAAGAAGAAAAA<u>AT</u>

<u>G</u>AAACATAATCAAGACAGAGTTGAAGAGCTGAGTCTAGTACGTGTAGATGACACCATCTCTC

AACCACCAAGGTATGCTCCGAGTGCACCGATGCCATCATCTATGCCAACGGTTGCCCTTGAA

ATATTGGA $^{(192)}$ C $^{(333)}$ <u>TTGATCCGGAGGAAGAGTTCTTACGTAATTATAGAGTTTCAAGGGAG</u>

<u>ATGACTGAAGTGGAAAAATTTATCGAATTCCGTGCTAAAAACGAGATGCAAATATACGGAGA</u>

<u>TATACCCATTAAGGTATGGTGTTGTTTCATCAATGAACTGAGTGCGGAATTAAAACATATTC</u>

<u>CCTTAGGGATGCAAGTTATGGCTGACTTTGTAAACCGTTTCGATTCACCATTCCATCAGGGG</u>

<u>AATAGAGATTTATCAAATCTTGAAGATTTTCAAGTTGCATACACTACGCCGCTTTTGTTTGA</u>

<u>AATGTGTTGCATGGAATCAATTTTAGAATTCAATATCAAAATGCGTATGCGTGAAGAAGATA</u>

<u>TCTCGGCGCTGGAATTCGGTGAT</u> $^{(713)}$ T $^{(658)}$ ACAGAGTTCTCGTCAGTCCCGCTGGATGGTTT

CGAAATGCCATTAACC<u>TGA</u>GGACAGTAGGTAGAGTGGCGCCCCGAGGTTTACGTCGTGCAGG

GTGGTTGACCTCGCGGCGTAGACTCCCACTGCTGTATAACGGGGAGGGTGCGCGACACTAC

ACACTTAC $^{(822)}$

BPS1. Sequence of the S10 genome segment BPS1. Start codons and stop codon of NS3/NS3a are bold + underlined, and underlined, respectively. The insertion of the S1 sequence is double underlined. This insertion corresponding to 333-713 of S1 of BTV1 is located between positions 192 and 658 of S10 of BTV8. S10 genome segment BPS1 is 738 bases in length and no otherchanges were found.

(SEQ ID NO: 81)

G $^{(1)}$ TTAAAAAGTGTCGCTGCCATGCTATCCGGGCTGATCCAAAGGTTCGAAGAAGAAAAA<u>AT</u>

<u>G</u>AAACATAATCaAGACAGAGTTGAAGAGCTGAGTCT $^{(96)}$ C $^{(550)}$ ACCATTCCATCAGGGGAAT

AGAGATTTATCAAATCTTGAAGATTTTCAAGTTGCATACACTACGCCGCTTTTGTTTGAAAT

-continued

<u>GTGTTGCATGGAATCAATTTTAGAATTCAATATCAAAATGCGTATGCGTGAAGAAGATATCT</u>

<u>CGGCGCTGGAATTCGGTGATATGAAAGTTGATCCGGTTGGACTATTGCGTGAGTTTTTCATT</u>

<u>CTGTGCTTACCACACCCAAAGAAGATTAACAACGTTCTAAGAGCACCATACTCTTGGTTTGT</u>

<u>AAAGATGTGGGGCGTCGGAGCTGATCCGATCGTTGTTTTACAATCTACGGCAGGCGATGACA</u>

<u>GGAATTCAAAGGA</u>(892) A(97) GTACGTGTAGATGACACCATCTCTCAACCACCAAGGTATGCT

CCGAGTGCACCGATGCCATCATCTATGCCAACGGTTGCCCTTGAAATATTGGACAAAGCGAT

GTCAAACACAACTGGTGCAACGCAAACACAAAAGGCGGAGAAGGCTGCATTCGCATC(258)gt acT(634)AATGATGCGGTGAGGATGAGTTTTACAGAGTTCTCGTCAGTCCCGCTGGATGGTTT

CGAAATGCCATTAACC<u>TGA</u>GGACAGTAGGTAGAGTGGCGCCCCGAGGTTTACGTCGTGCAGG

GTGGTTGACCTCGCGGCGTAGACTCCCACTGCTGTATAACGGGGAGGGTGCGCGACACTAC

ACACTTAC(822)

BPS1-2. Sequences of the S10 genome segment of BPS1-2. Start codons and stop codon of NS3/NS3a are bold and underlined, and underlined, respectively. The insertion of the S1 sequence is double underlined. This 68-nucleotide insertion corresponding to 550-892 of S1 of BTV1 is located between positions 96 and 97 of S10 of BTV8. S10 genome segment BPS1-2 is 794 bases in length and no other changes were found.

(SEQ ID NO: 82)
G(1)TTAAAAAGTGTCGCTGCCATGCTATCCGGGCTGATCCAAAGGTTCGAAGAAGAAAAA(58)

<u>A</u>(768)<u>TTAGAGATGATATTGCGAGCTTGGATGAGATATGTAATAGGTGGATACAGAGTAGGCA</u>

<u>CGACCCCGG</u>(835) A(59) TGAAACATAATCaAGACAGAGTTGAAGAGCTGAGTCTAGTACGTGT

AGATGACACCATCTCTCAACCACCAAGGTATGCTCCGAGTGCACCGATGCCATCATCTATGC

CAACGGTTGCCCTTGAAATATTGGACAAAGCGATGTCAAACACAACTGGTGCAACGCAAACA

CAAAAGGCGGAGAAGGCTGCATTCGCATC(258)gtacT(634)AATGATGCGGTGAGGATGAGTT

TTACAGAGTTCTCGTCAGTCCCGCTGGATGGTTTCGAAATGCCATTAACC<u>TGA</u>GGACAGTAG

GTAGAGTGGCGCCCCGAGGTTTACGTCGTGCAGGGTGGTTGACCTCGCGGCGTAGACTCCCA

CTGCTGTATAACGGGGAGGGTGCGCGACACTACACACTTAC(822)

BPS2. Sequences of the S10 genome segment BPS2. Start codons and stop codon of NS3/NS3a are bold and underlined, and underlined, respectively. The insertion of the S2 sequence is double underlined. This 68-nucleotide insertion corresponding to 768-835 of S2 of BTV1 is located between positions 58 and 59 of S10 of BTV8. S10 genome segment BPS2 is 519 bases in length and no other changes were found.

(SEQ ID NO: 83)
G(1)TTAAAAAGTGTCGCTGCCATGCTATCCGGGCTGATCCAAAGGTTCGAAGAAGAAAAA(58)

<u>A</u>(768)<u>TTAGAGATGATATTGCGAGCTTGGATGAGATATGTAATAGGTGGATACAGAGTAGGCA</u>

<u>CGACCCCG</u>(834)CCA(59)TGT(634)AATGATGCGGTGAGGATGAGTTTTACAGAGTTCTCGTCA

GTCCCGCTGGATGGTTTCGAAATGCCATTAACC<u>TGA</u>GGACAGTAGGTAGAGTGGCGCCCCGA

GGTTTACGTCGTGCAGGGTGGTTGACCTCGCGGCGTAGACTCCCACTGCTGTATAACGGGGG

AGGGTGCGCGACACTACACACTTAC(822)

BPS2del. Sequence of the S10 genome segment BPS2del. BPS2 was synthetically derived with a few modifications to incorporate NcoI and PsiI cloning sites. Subsequently, the sequence between these sites was deleted resulting in BPS2del. Start codons and stop codon of NS3/NS3a are bold and underlined, and underlined, respectively. The insertion of the S2 sequence is double underlined. This 67-nucleotide insertion corresponding to 768-834 of S2 of BTV1 and two extra C residues are located between positions 58 and 59 of S10 of BTV8. S10 genome segment BPS2del is 319 bases in length and no other changes were found.

An overview of the deleted viruses, and the revertants thereof, is provided in FIG. 3.

Example 10 cDNAs of S10 genome segments of BPS1 and BSP2 were cloned in appropriate plasmids for in vitro RNA synthesis. These RNAs were used to rescue BTV with S10 genome segment BPS1 or BPS2. This rescue of BPS1 and BPS2 was successful with GMS2, and the efficiency was comparable to that of rgBTV1. No extra passages of transfected cells were needed to prepare virus stocks. This indicates that no further selection was needed. Indeed, the sequences of S10 genome segment BPS1 and BPS2 of these virus stocks were confirmed. A virus stock of BPS2 was prepared and used for further studies, this virus was named modBTvac-1.

Representative examples of the production of modBTvac-1 in BSR cells, detection of modBTvac-1 by panBTV PCR assays, and virus release of modBTvac-1 from BSR and KC cells are provided in FIG. 4.

The stability of the S10 genome segment BPS2 and BPS2del of these NS3/NS3a minus BTV mutants was further analyzed. These viruses were successively passed on BSR cells for at least 10 passages. NS3/NS3a expression remained negative as studied by IPMA for the highest passage number available. Stability of genome segment S10 was studied by PCR followed by agarose gel electrophoresis. The sequence of the complete genome segment S10 of the highest available passage number was confirmed.

Example 11

Genome segment S10 of modBTvac-1 (BPS2) was used to rescue BTV variants with this mutated genome segment S10. S10 genome segment BPS2 contains a large deletion from the BsiWI to the PsiI site, and 68 base pairs from genome segment S2 inserted directly downstream from the $2^{nd}$ AUG start codon.

BTV mutant BPS2 as described in example 9, was rescued directly with S10 RNA based on BPS2 and was named modBTvac-1. Note that modBTvac-1 and rgBTV1 only differ in the S10 genome segment.

S10 genome segment BPS2 was used in combination with genome segment S2[VP2] of rgBTV8 (van Gennip et al., 2012a. PLoS ONE 7, e30540). The set of 10 genome segments was completed with genome segments of rgBTV1 and virus was rescued. The rescued virus was named modBTvac-8. Similarly, several modBTvac-x viruses were generated for BTV serotypes 4, 6, and 9.

S10 genome segment BPS2 was completed with genome segments S1-S9 of virulent rgBTV8 (van Gennip et al., 2012a. PLoS ONE 7, e30540). Virus was rescued comparable to the efficiency of rgBTV8, and no additional passages were needed for the preparation of a virus stock. The rescued virus was named rgBTV8-BPS2, and the virus stock was obtained for further analysis. Genome segment S10 was completely sequenced and indeed no additional changes were found.

In addition, S10 genome segment BPS2 was completed with genome segments S1-S9 of non-virulent rgBTV6 (van Gennip et al., 2012a. PLoS ONE 7, e30540). Despite several attempts, rescue of rgBTV6-BPS2 had failed. Apparently, incorporation of S10 genome segment BPS2 is not possible in all virus backgrounds.

An overview of BTV variants with S10 genome segment BPS2 is provided below:

| BTV rescue with genome segment BPS2. | | | | |
|---|---|---|---|---|
| virus name | virus rescue | S2 genotyping | VP7 staining | NS3 staining |
| rgBTV1 | + | 1 | + | + |
| modBTvac-1 | + | 1 | + | − |
| modBTvac-2 | − | nd | nd | nd |
| modBTvac-4 | + | 4 | + | − |
| modBTvac-6 | + | 6 | + | − |
| modBTvac-8 | + | 8 | + | − |
| modBTvac-9 | + | 9 | + | − |
| modBTvac-16 | − | nd | nd | nd |
| rgBTV8 | + | 8 | + | + |
| rgBTV8-BPS2 | + | 8 | + | − |
| rgBTV6 | + | 6 | + | + |
| rgBTV6-BPS2 | − | nd | nd | nd |

This segment was used in combination with rgBTV1 segments (modBTvac-1), rgBTV6 (failed), and rgBTV8 (rgBTV8-BPS2). Similar to modBTvac-1, BPS2 was used in combination with S2 genome segments originating from other BTV serotypes and rgBTV1 segments (modBTvac-x, in which x represents the BTV serotype). All rescued viruses were immunostained with VP7 MAb ATCC1875, and the respective S2 genotyping assay. modBTvac-x viruses and rgBTV8-BPS2 were negative for NS3/NS3a expression.

Example 12

Infection experiments were performed in sheep as representative of most susceptible animal for Bluetongue. Clinical disease, viremia, induction of protection and the induction of immune responses like neutralizing and non-neutralizing antibody responses raised against different viral proteins were investigated in infected sheep. Sheep trials were monitored by standard methods as previously described ((van Gennip et al., 2012a. PLoS ONE 7, e30540; van Gennip et al., 2012b. PLoS ONE 7, e44619). Rectal body temperatures and clinical scores were recorded daily. The presence of BTV genomic RNA was determined by panBTV PCR assays. The presence of panBTV antibodies was determined by the VP7-ELISA and displayed as 100-value with a threshold value set at 50%. Antibodies raised against NS3/NS3a were detected by NS3/NS3a-IPMA and/or an experimental NS3/NS3a-ELISA. BTV-serotype specific neutralizing antibodies were determined by SNT with the indicated BTV serotypes.

All experiments with live animals were performed under the guidelines of the European Community (86/609) after approving by the Committee on the Ethics of animal experiments of the Central Veterinary Institute.

Female sheep of the same breed of 6-24 months old and free of BTV and BTV-antibodies were commercially sourced from the same flock of a Dutch farm. The sheep were randomly allocated to groups. On day 0 (0 day post immunization/vaccination [0 dpv] or infection/challenge [0 dpi/dpc]), the $1^{st}$ injection was performed as indicated. Subsequent injections were performed on the indicated days. Per injection, 1 ml of $10^5$ TCID$_{50}$/ml of BTV was injected subcutaneously (s.c.) between the shoulder blades left and right from the spinal cord and/or were injected intravenously (i.v.). Negative control groups received growth medium of mock-infected cells or were not injected.

Body temperature was recorded daily, and fever was defined as above the average temperature plus two times the standard deviation. Clinical signs were daily recorded according to the clinical score table for BTV8 animal trials (Backx et al., 2007. Vet Rec 161: 591-592; Backx et al., 2009. Vet Microbiol 138: 235-243; van Gennip et al., 2012a. PLoS ONE 7, e30540). Clinical signs were quantified by an adapted clinical reaction index (CRI) as described ((Huismans et al., 1987. Virology 157, 172-179). A maximum score of 12 was given to the cumulative total of fever readings (a) as described above from days 4 to 15 post each inoculation (dpi), a clinical score according the clinical score table (b). An additional 4 points were added to the sum of a and b if death occurred within 14 dpi. Generally, the efficacy of vaccine candidates is measured by reduction of the CRI, seroconversion in general, induction of neutralizing immune response, and by reduction of viremia as measured by PCR testing.

EDTA-blood samples were collected by indicated intervals. Generally, the first week after each injection daily followed by sampling every other day until the end of the trial. EDTA-blood samples were tested by panPCR BTV assays for detection of BTV RNA, or by specific PCR tests for detection of certain genome segments. Occasionally, amplicons were sequenced to identify specific genome segments.

Serum samples were collected more frequently in the second week after each injection. Sera were tested by BTV-specific ELISAs and/or SNT for the detection of BTV-serotype specific (neutralizing) antibodies. Occasionally, sera were used to immunostain transiently expressed BTV proteins.

rgBTV1 and modBTvac-1 were compared after infection of sheep. rgBTV1 and modBTvac-1 share 9 out of 10 genome segments, and differ only in genome segment S10. Groups of two sheep were s.c. and i.v. infected with rgBTV1 or modBTvac-1. Each route of administration contained 1 ml 10*5 TCID50/ml. The sheep were re-infected twice with an interval of 3 weeks with the same virus. The sheep were monitored up to nine weeks (63 dpi). No obvious clinical signs were observed (see FIG. 5), and no increase of body temperature was measured for sheep infected with modBTvac-1. Unfortunately, no records of body temperature were available for 0-10 dpi. ModBTvac-1 infected sheep were tested negative by panBTV PCR assay, whereas seroconversion was demonstrated by VP7-ELISA (FIG. 5). The antibody titer against VP7 and VP2 was comparable to that of sheep infected with rgBTV1 (FIG. 6). From these results, it can be concluded that modBTvac-1 is as protective as rgBTV-1, whereas virulence and viremia are reduced.

Example 13

Infection of BTV lacking NS3/NS3a expression will not raise antibodies (Abs) directed against this protein. However, the immune response by NS3/NS3a is not extensively studied at all. It is not known whether the NS3 humoral response is conserved, although immunogenic regions were mapped that are extremely conserved. Further, studies regarding long lasting humoral responses were mainly limited to the response against VP2 which are important for neutralization (nAbs), and against VP7 which are high and conserved and thus used in commercially available ELISAs. Here, the response against NS3 after infection by reference BTV strains is studied. Further, the response against NS3/NS3a after experimental and natural infection by BTV8/net06 as BTV representative is investigated.

NS3/NS3a expression from the gene of wtNS3/NS3a and from of BPS2 was studied. Transfected BSR monolayers expression NS3/NS3a, BPS2-NS3/NS3a, or VP7 were immunostained by sera raised against different BTV serotypes (IPMA).

FP-T7 infected BSR monolayers were transfected with plasmids with genes under transcriptional control of the T7-promoter, as described for GMS2).

| NS3/NS3a mutant | serum 887 | BTV-ref 1-10 |
|---|---|---|
| NS3/NS3a | + | + |
| BPS2 | − | − |
| VP7 | ++ | ++ |

Expression of the wtNS3/NS3a gene, the BPS2 gene or of the VP7 gene was studied. Expression was studied by immunostaining with BTV reference sera that were raised against BTV serotypes 1 to 10 (BTV-ref 1-10). Serum 887 raised against BTV8/net06 (Backx et al., 2007. Vet Rec 161, 591-592) served as positive control. Immunostaining was compared to that of expressed VP7. Other BTV reference sera are not tested yet.

43 cattle sera and 31 sheep sera from of naturally infected animals were collected in 2007 and 2008 were confirmed to be positive by a commercially available VP7-ELISA (ID SCREEN®; ID.VET). These were tested by an indirect ELISA for VP7, and an experimental indirect ELISA based on NS3/NS3a (Ingenasa; Spain). The latter two ELISAs were performed by Ingenasa according to their instructions.

| Cattle | | VP7 + | VP7 − |
|---|---|---|---|
| NS3 | + | 37 | 0 |
| | − | 0 | 6* |

VP7: OD average: 1.121 (SD: 0.419)
NS3: OD average: 0.591 (SD: 0.197)

In general terms, all seropositive animals (by VP7-cELISA with a cut-off value of 50% inhibition (ID.VET) were also positive to NS3-Abs. The asterix (*) indicates six cows that were tested negative by indirect NS3-ELISA (Ingenasa), and were also negative or close to negative by indirect VP7-ELISA by use of a cut-off value of 0.4 (Ingenasa).

| sheep | | VP7 + | VP7 − |
|---|---|---|---|
| NS3 | + | 31 | 0 |
| | − | 0 | 0 |

VP7: OD average: 1.041 (SD: 0.384)
NS3: OD average: 0.765 (SD: 0.242)

Example 14

Longitudinally collected sera from three cows naturally infected by BTV8/net06 and two heifers experimentally infected by BTV8/net06 were used (van Rijn et al., 2012b. J Vet Diagn Invest 24: 469). Pregnant cows 693, 858, and 859 were removed from the infected zone during the starting BT-8 outbreak in Autumn 2006. It was estimated that these cows has been infected at least 50 days earlier. EDTA blood from these cows was collected, washed and pooled. Three heifers were injected with this washed EDTA blood, but only heifers 860 and 861 were successfully infected. Sera were tested with the competition VP7-ELISA (ID.VET), the indirect VP7-ELISA (Ingenasa), and an experimental indirect ELISA based on NS3/NS3a. All ELISAs were performed according to the instructions of the suppliers (see FIGS. 12A-12E).

The conclusion of these experiments is that VP7-Abs are present for longer time than NS3-Abs. Titers of NS3-Abs start to decline after approximately three months, and convert to doubtful/negative at 4-5 months post infection in this experimental ELISA with a cut off of 0.4.

Example 15

BPS2del (see example 9) and Segment-2 of BTV8 were incorporated in rgBTV1 (BTV1 backbone). StartSdel (see example 9, FIG. 3) and Segment-2 of BTV8 were incorporated in rgBTV6 (BTV6 backbone). BPS2del was also incorporated in rgBTV8 (BTV8 backbone).

In short, all three generated BTV backbones contain Segment-2 of serotype 8 and the NS3/NS3a knockout phenotype, whereas the other eight genome segments originates from BTV1, BTV6 or BTV8, respectively. Equal amounts of BTV8 were inactivated by standard bromo-ethylimine (BEI) treatment.

Groups of four sheep were subcutaneously vaccinated with 2 ml 10*5 TCID50/ml of each BTV backbone or with equal amounts of inactivated BTV8. One group served as negative control. At 21 days post vaccination (21 dpv), sheep were infected with 4 ml 10*5 TCID50/ml virulent BTV8. The sheep were monitored up to 42 dpv (21 days after virus challenge).

Figure 7F:
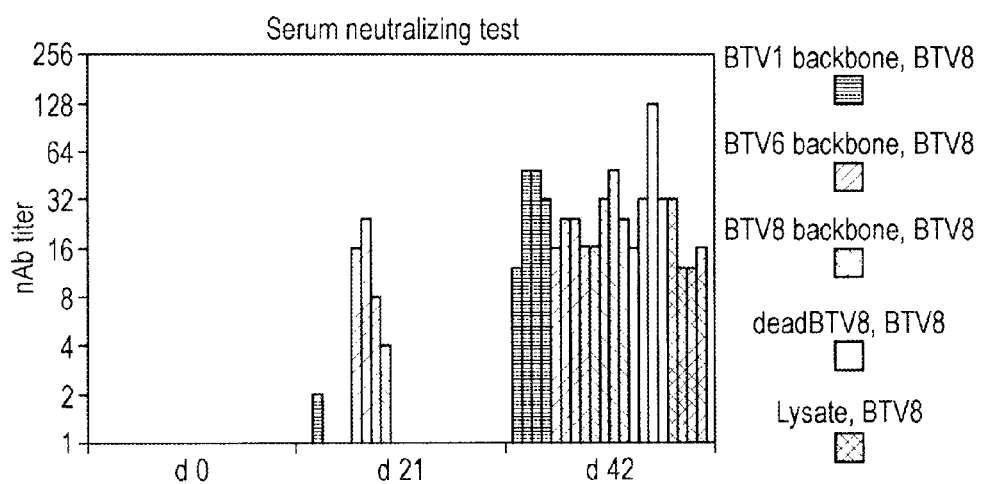
Figure 7G:
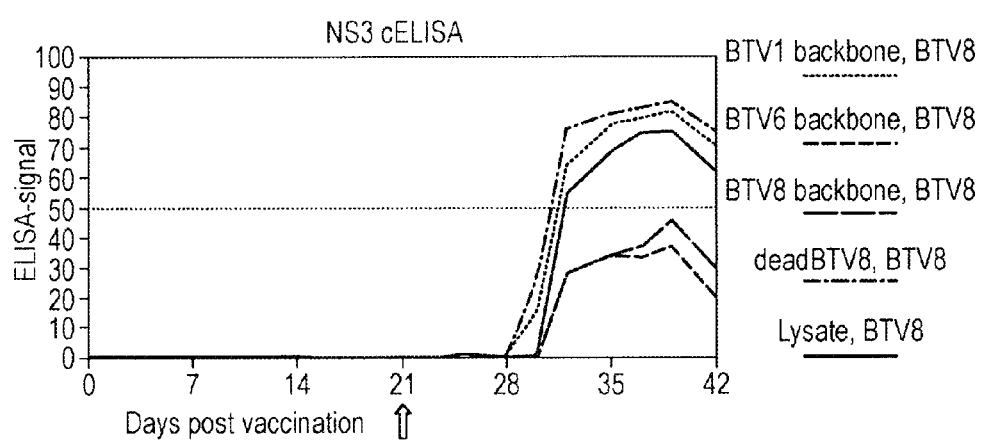

After vaccination, no increase of body temperature was measured (FIG. 7A), and no clinical signs were observed (FIG. 7B). Up to 21 dpv (prior challenge), all groups were negative by panBTV S10 PCR assay as well as in the panBTVS1 PCR assay (FIGS. 7C and D). Serological tests showed seroconversion for vaccinated animals, whereas inactivated BTV8 did not induce a significant VP7 ELISA signal (FIG. 7E). The group vaccinated with BTV6 backbone showed neutralizing antibodies directed against BTV serotype 8 (FIG. 7F). All groups, including vaccinated groups, remained seronegative for NS3-Abs (FIG. 7G).

Groups vaccinated with the BTV6 and BTV8 backbone were protected against BTV8-mediated disease (no fever and no clinical signs) (FIGS. 7A and 7B). Except for BTV6 backbone, viremia was detected by both PCR tests for all groups after challenge (21 dpv/0 dpc to 42 dpv/21 dpc) (FIGS. 7C and 7D). All groups responded to the BTV8 challenge by induction of an immune response, as is indicated by the positive VP7 ELISA and neutralizing Abs titers (VP2 antibodies) (FIGS. 7E and 7F). All groups also responded to the BTV8 challenge by induction of a NS3-mediated immune response, as is indicated by the NS3 ELISA, although groups vaccinated with the BTV6 and BTV8 backbone remain negative as these showed a blocking percentage below the threshold set at 50% (FIG. 7G).

Example 16 rgBTV6 with Seg-2 of serotype 8 and the NS3/NS3a knockout phenotype (see BTV6 backbone in example 15) is a bluetongue virus DISA vaccine 8. Groups of four sheep were subcutaneously vaccinated with this DISA vaccine: two groups with 2 ml 10*5 TCID50/ml (H), one group with 2 ml 10*4 TCID50/ml (M), and one group with 2 ml 10*3 TCID50/ml (L). At 21 dpv, both groups H were subcutaneously vaccinated again with 2 ml 10*5 TCID50/ml again (DISA DISA), whereas group M and L were not boosted. Group M and L were euthanized at 42 dpv, while monitoring of groups DISA DISA (H) was continued.

Figure 8A:
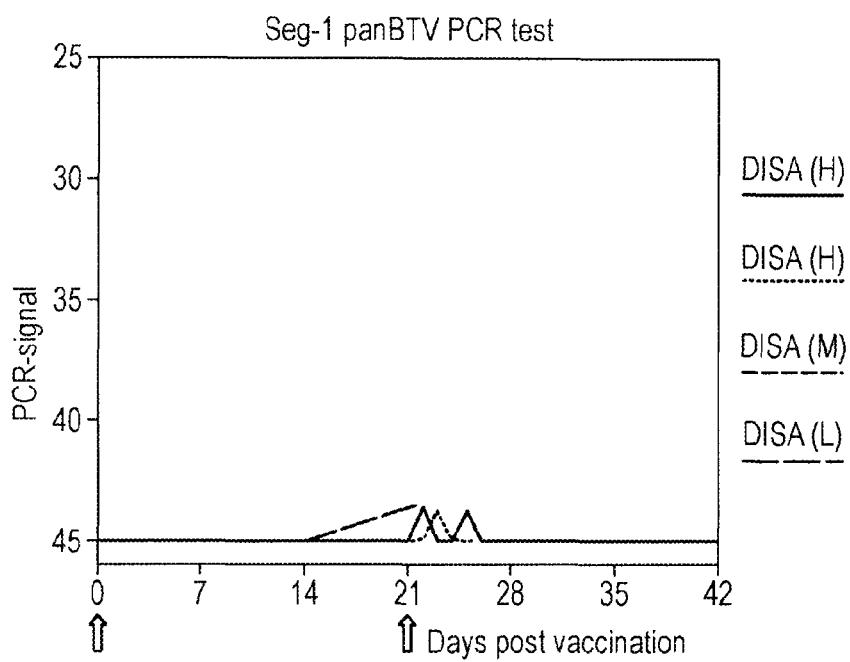
Figure 8B:
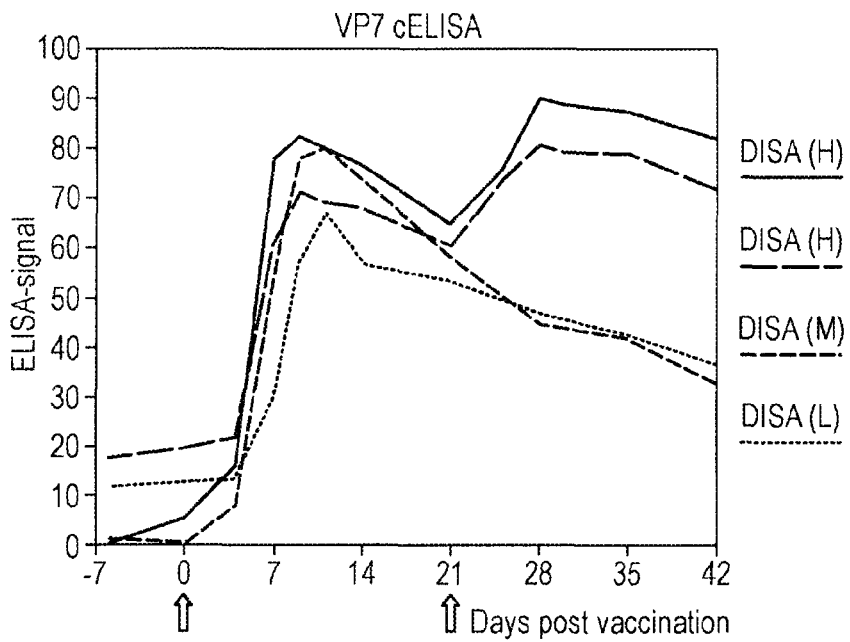

All groups remained negative by panBTVS1 PCR testing (FIG. 8A). Three sheep from different groups showed a very low PCR signal (high Ct value) for one day. Seroconversion was observed in all vaccinated groups. VP7 ELISA signals declined in the second week post vaccination in all groups. Revaccination of both groups H animals resulted in an increase of the VP7 ELISA signal (see FIG. 8B). VP7 ELISA signals in group M and L further decreased, and finally became negative after about 4 weeks post vaccination (FIG. 8B). Vaccinated and revaccinated groups showed neither an increase in body temperature nor clinical signs.

At 78 dpv, two new groups of four sheep, free of BTV and BTV Abs, were included as control groups. Control groups and vaccinated groups H were infected with 4 ml 10*5 TCID50/ml at 84 dpv (0 days post challenge (dpc)): one vaccinated and one control group were infected with virulent BTV2 (DISA DISA BTV2, and BTV2), and the other two groups with virulent BTV8 (DISA DISA BTV8, and BTV8). The sheep were monitored up to 105 dpv/21 dpc.

Figure 9A:
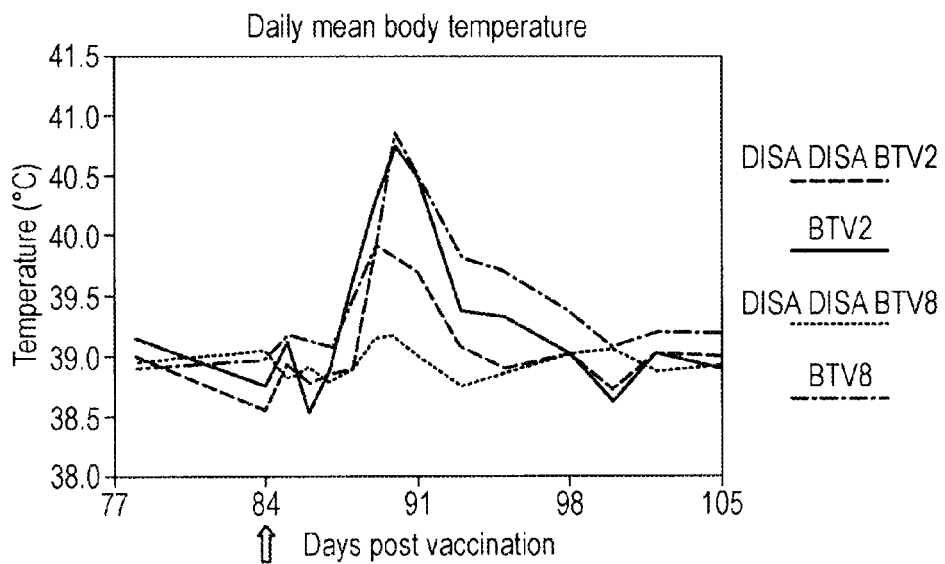
Figure 9C:
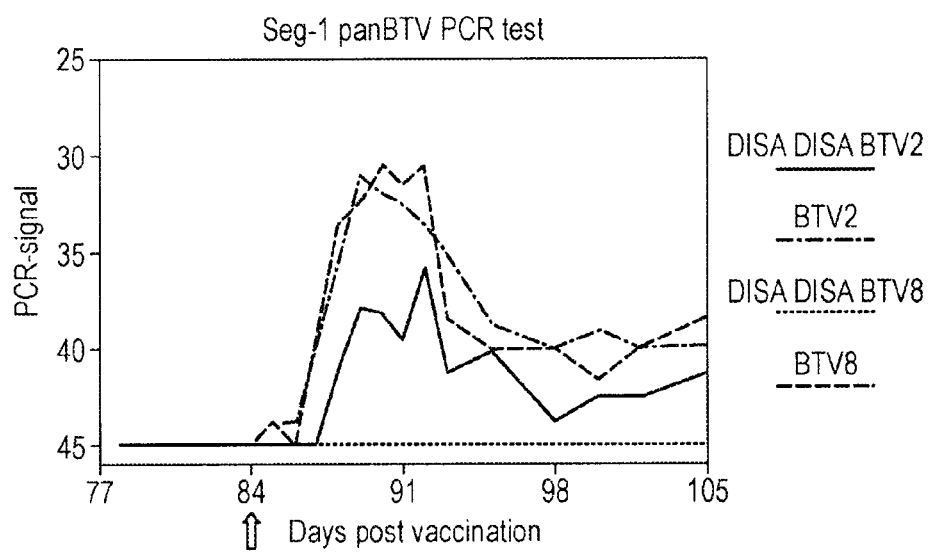
Figure 9F:
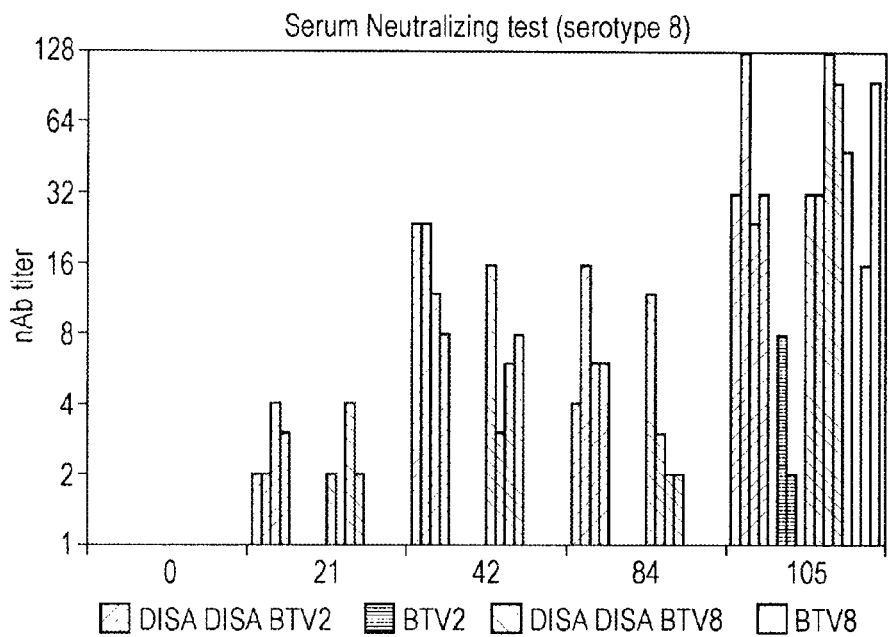
Figure 9G:
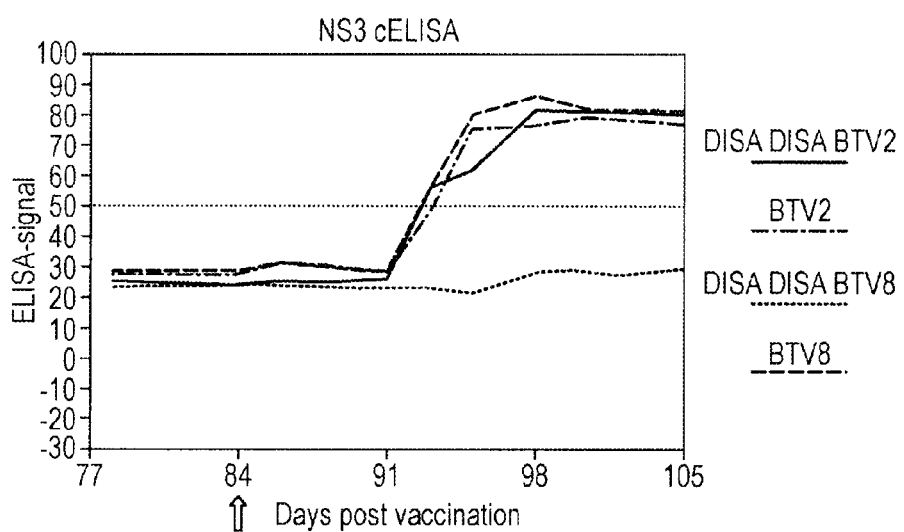

In contrast to the vaccinated group challenged with BTV8, which were completely protected, increase in body temperature and clinical signs were observed in the other groups. Thus, virulent BTV2 induced increased body temperature and clinical signs after vaccination with BT DISA vaccine 8. However, these were less pronounced than in the BTV2 control group suggesting partial protection by BT DISA vaccine 8 (FIG. 9A-B). Partial protection was further confirmed by S1 panBTV PCR testing and by the NS3 ELISA (FIGS. 9C and 9G). Finally, all groups showed seroconversion/boosting after challenge in VP7 ELISA, NS3 ELISA and serum neutralization tests, except for the vaccinated group challenged with BTV8 which remained negative in the NS3 ELISA (FIGS. 9D, 9E, 9F and 9G). Apparently, protection is serotype specific and related to the immune response against VP2 of serotype 8 as present in BT DISA vaccine 8.

Example 17

Several Seg-10 mutants were generated containing mutations in Seg-10 of BTV8 or BTV6. A various number of AUG>GCC mutations in the NS3-ORF were generated; AUG3 tm 13, AUG total, NS3b His-tag for Seg-10 of BTV8, and AUG total DIVA, and NS3knockout DIVA for Seg-10 of BTV6. Further, STOP codons downstream from AUG2 were introduced in NS3b His-tag (for BTV8 Seg-10) and in NS3knockout DIVA (for BTV6 Seg-10). Finally, to detect C-terminal expression of NS3 six codons encoding a His-tag were introduced in-frame and adjacent upstream from the STOP codon of NS3/NS3a (NS3b His-tag). Mutations (underlined), mutated AUG codons and introduced STOP codons (bold), and His codons encoding the His-tag (small, underlined and bold) are indicated.

```
BTV8 Seg-10 of 'AUG3 tm 13'
                                          (SEQ ID NO: 84)
GTTAAAAAGTGTCGCTGCCATGCTATCCGGGCTGATCCAAAGGTTCGAA

GAAGAAAAAATGAAACATAATCAAGACAGAGTTGAAGAGCTGAGTCTAG

TACGTGTAGATGACACCATCTCTCAACCACCAAGGTATGCTCCGAGTGC

ACCGGCCCCATCATCTGCCCCAACGGTTGCCCTTGAAATATTGGACAAA

GCGGCCTCAAACACAACTGGTGCAACGCAAACACAAAAGGCGGAGAAGG

CTGCATTCGCATCGTACGCGGAAGCGTTTCGTGATGATGTAAGACTGAG

ACAGATCAAGCGCCATGTGAACGAGCAGATTTTACCAAAATTAAAAAGT

GATCTAAGTGGATTGAAGAAGAAACGAGCAATCATACACACTACTCTAT

TAGTAGCGGCTGTGGTTGCGCTGTTGACATCAGTTTGTACCCTTTCAAG

CGATGCCAGTGTGGCCTTTAAGATAAATGGAACTAAAACAGAAGTGCCT

TCATGGTTTAAAAGCCTTAACCCGGCCCTTGGCGTGGTCAATTTGGGAG

CAACTTTTCTGGCCGCCGTTTGCGCAAAGAGTGAAAGAGCCTTGAACCA
```

```
GCAGATAGATGCCATAAAGAAGGAAGTGGCCAAGAAACAATCTTATAAT

GATGCGGTGAGGGCCAGTTTTACAGAGTTCTCGTCAGTCCCGCTGGATG

GTTTCGAAGCCCCATTAACCTGAGGACAGTAGGTAGAGTGGCGCCCCGA

GGTTTACGTCGTGCAGGGTGGTTGACCTCGCGGCGTAGACTCCCACTGC

TGTATAACGGGGAGGGTGCGCGACACTACACACTTAC
```
BTV8 Seg-10 of 'AUG total'
(SEQ ID NO: 85)
```
GTTAAAAAGTGTCGCTGCCGCCCTATCCGGCTGATCCAAAGGTTCGAA

GAAGAAAAAGCCAAACATAATCAAGACAGAGTTGAAGAGCTGAGTCTAG

TACGTGTAGATGACACCATCTCTCAACCACCAAGGTATGCTCCGAGTGC

ACCGGCCCCATCATCTGCCCCAACGGTTGCCCTTGAAATATTGGACAAA

GCGGCCTCAAACACAACTGGTGCAACGCAAACACAAAAGGCGGAGAAGG

CTGCATTCGCATCGTACGCGGAAGCGTTTCGTGATGATGTAAGACTGAG

ACAGATCAAGCGCCATGTGAACGAGCAGATTTTACCAAAATTAAAAAGT

GATCTAAGTGGATTGAAGAAGAAACGAGCAATCATACACACTACTCTAT

TAGTAGCGGCTGTGGTTGCGCTGTTGACATCAGTTTGTACCCTTTCAAG

CGATGCCAGTGTGGCCTTTAAGATAAATGGAACTAAAACAGAAGTGCCT

TCATGGTTTAAAAGCCTTAACCCGGCCCTTGGCGTGGTCAATTTGGGAG

CAACTTTTCTGGCCGCCGTTTGCGCAAAGAGTGAAAGAGCCTTGAACCA

GCAGATAGATGCCATAAAGAAGGAAGTGGCCAAGAAACAATCTTATAAT

GATGCGGTGAGGGCCAGTTTTACAGAGTTCTCGTCAGTCCCGCTGGATG

GTTTCGAAGCCCCATTAACCTGAGGACAGTAGGTAGAGTGGCGCCCCGA

GGTTTACGTCGTGCAGGGTGGTTGACCTCGCGGCGTAGACTCCCACTGC

TGTATAACGGGGAGGGTGCGCGACACTACACACTTAC
```
*A) BTV8 Seg-10 of 'NS3b His-tag'
(SEQ ID NO: 86)
```
GTTAAAAAGTGTCGCTGCCGCCCTATCCGGCTGATCCAAAGGTTCGAA

GAAGAAAAAGCCAAACATAATCAAGACAGAGTTGAAGAGCTGAGTCTAG

TACGTGTAGATGACACCATCTAGCAACCACCAAGGTATGTAGTAGGTGC

ACCGATGCCATCATCGATGCCAACGGTTGCCCTTGAAATATTGGACAAA

GCGATGTCAAACACAACTGGTGCAACGCAAACACAAAAGGCGGAGAAGG

CTGCATTCGCATCGTACGCGGAAGCGTTTCGTGATGATGTAAGACTGAG

ACAGATCAAGCGCCATGTGAACGAGCAGATTTTACCAAAATTAAAAAGT

GATCTAAGTGGATTGAAGAAGAAACGAGCAATCATACACACTACTCTAT

TAGTAGCGGCTGTGGTTGCGCTGTTGACATCAGTTTGTACCCTTTCAAG

CGATATGAGTGTGGCCTTTAAGATAAATGGAACTAAAACAGAAGTGCCT

TCATGGTTTAAAAGCCTTAACCCGATGCTTGGCGTGGTCAATTTGGGAG

CAACTTTTCTGATGATGGTTTGCGCAAAGAGTGAAAGAGCCTTGAACCA

GCAGATAGATATGATAAAGAAGGAAGTGATGAAGAAACAATCTTATAAT

GATGCGGTGAGGATGAGTTTTACAGAGTTCTCGTCAGTCCCGCTGGATG

GTTTCGAAATGCCATTAACCCATcatcaccatcaccacTGAGGACAGTA

GGTAGAGTGGCGCCCCGAGGTTTACGTCGTGCAGGGTGGTTGACCTCGC
```
```
GGCGTAGACTCCCACTGCTGTATAACGGGGGAGGGTGCGCGACACTACA

CACTTAC
```
*B) BTV6 Seg-10 of 'AUG total DIVA'
(SEQ ID NO: 87)
```
GTTAAAAAGTGTCGCTGCCGCCCTATCCGGGCTGATCCAAAGGTTCGAA

GAAGAAAGGGCCAAACACAATCAAGATAGAGTTGAAGAGCTGAGTCTAG

TGCGTGTAGATGATACCATTTCTCAACCACCAAGGTATGCCCCGAGTGC

GCCGGCCCCATCATCTGCCCCAACGGTTGCCCTTGAAATATTGGACAAG

GCGGCCTCAAACACAACTGGTGCAACGCAAACACAGAAAGCGGAGAAGG

CAGCTTTTGCTAGCTATGCGGAAGCGTTTCGTGATGATGTGAGATTGAG

ACAGATCAAACGCCATGTGAACGAGCAGATTTTACCAAAATTAAAAAGT

GATCTAAGTGGATTGAAGAAGAAGCGAGCAATCATACACACTACTCTAT

TGGTAGCTGCTGTGGTTGCGCTGTTGACATCAGTTTGCACCCTTTCAAG

CGATGCCAGTGTGGCCTTTAAGATAAATGGAACTAAGACAGAAGTGCCT

TCATGGTTTAAAAGCCTTAACCCGGCCCTTGGCGTTGTCAATTTGGGAG

CAACTTTTTTGGCCGCCGTTTGCGCAAAGAGTGAAAGAGCCTTGAACCA

GCAGATAGATGCCATAAAGAAGGAGGTGGCCAAGAAACAATCTTATAAT

GACGCGGTGAGGGCCAGTTTTACGGAGTTCTCGTCAATCCCGCTGGATG

GTTTCGAAGCCCCATTAACCTGAGGACAGTAGGTAGAGTGGCGCCCCGA

GGTTTGCGTCGTGCAGGGTGGTTGACCTCGCGGCGTAGACTCCCACTGC

TGTATAACGGGGAGGGTGCGCGACACTACACACTTAC
```
*C) BTV6 Seg-10 of 'NS3knockout DIVA'
(SEQ ID NO: 88)
```
GTTAAAAAGTGTCGCTGCCGCCCTATCCGGGCTGATCCAAAGGTTCGAA

GAAGAAAGGGCCAAACACAATCAAGATAGAGTTGAAGAGCTGAGTCTAG

TGCGTGTATAGGATACCATTTCTCAACCACCAAGGTAGGCCCCGAGTGC

GCCGGCCCCATCATCTGCCCCAACGGTTGCCCTTGAAATATTGGACAAG

GCGGCCTCAAACACAACTGGTGCAACGCAAACACAGAAAGCGGAGAAGG

CAGCTTTTGCTAGCTATGCGGAAGCGTTTCGTGATGATGTGAGATTGAG

ACAGATCAAACGCCATGTGAACGAGCAGATTTTACCAAAATTAAAAAGT

GATCTAAGTGGATTGAAGAAGAAGCGAGCAATCATACACACTACTCTAT

TGGTAGCTGCTGTGGTTGCGCTGTTGACATCAGTTTGCACCCTTTCAAG

CGATGCCAGTGTGGCCTTTAAGATAAATGGAACTAAGACAGAAGTGCCT

TCATGGTTTAAAAGCCTTAACCCGGCCCTTGGCGTTGTCAATTTGGGAG

CAACTTTTTTGGCCGCCGTTTGCGCAAAGAGTGAAAGAGCCTTGAACCA

GCAGATAGATGCCATAAAGAAGGAGGTGGCCAAGAAACAATCTTATAAT

GACGCGGTGAGGGCCAGTTTTACGGAGTTCTCGTCAATCCCGCTGGATG

GTTTCGAAGCCCCATTAACCTGAGGACAGTAGGTAGAGTGGCGCCCCGA

GGTTTGCGTCGTGCAGGGTGGTTGACCTCGCGGCGTAGACTCCCACTGC

TGTATAACGGGGAGGGTGCGCGACACTACACACTTAC
```

BTV mutants with mutated Seg-10 were generated. Mutations in Seg-10 were confirmed by sequencing of Seg-10. Overview of results is indicated in Table 4.

TABLE 4

| name | Seg of origin of BTV1 | origin of Seg-10 | mutation in Seg-10 | IPMA VP7 | NS3 | His | CPE |
|---|---|---|---|---|---|---|---|
| — | 1-9 | 8 | — | + | + | − | + |
| AUG3 tm 13 | 1-9 | 8 | AUG$^{3+13}$ –> GCC$^{3+13}$ | + | nd | nd | + |
| AUG total | 1-9 | 8 | AUG$^{1+13}$ –> GCC$^{1+13}$ | + | nd | nd | − |
| in-frame His-tag | 1-9 | 8 | insert of 6 His codons | + | + | + | + |
| NS3b His-tag | 1-9 | 8 | *A | + | − | + | small |
| AUG total DIVA | | 6 | *B | nd | nd | nd | nd |
| NS3knockout DIVA | | 6 | *C | nd | nd | nd | nd |

CPE phenotype in BSR infected monolayers was scored as similar to BTV1 (+), smaller CPE plaques (small), or no CPE (−). IPMA was performed on infected monolayers with VP7 Ab ATCC1875, MAbs raised against BTV-NS3/NS3a or with His-tag Abs (+: staining, −: no staining, nd: not done). Mutations in Seg-10 are indicated, referred to the complete sequence as given above (*A to *C), or no mutations (−).

Example 18

Several AHSV4LP mutants were generated with mutations in Seg-10 (AUG1, AUG1+2, AUG1+2 & STOPS, deILD, AUGtotal, NS3knockout DIVA, AUG1+2 & delTMR1), and delTMR2AUG1+2 & delTMR2. Mutations are underlined and mutated AUG codons and introduced STOP codons are in bold.

```
Seg-10 of AHSV4LP:
                                          (SEQ ID NO: 89)
GTTAAAATTATCCCTTGTCATGAATCTAGCTACAATCGCCAAGAATTATA

GCATGCATAATGGAGAGTCGGGGCGATCGTCCCTTATGTGCCACCACCA

TACAATTTCGCAAGTGCTCCGACGTTTTCTCAGCGTACGAGTCAAATGGA

GTCCGTGTCGCTTGGGATACTTAACCAAGCCATGTCAAGTACAACTGGTG

CGAGTGGGGCGCTTAAAGATGAAAAAGCAGCATTCGGTGCTATGGCGGAA

GCATTGCGTGATCCAGAACCCATACGTCAAATTAAAAAGCAGGTGGGTAT

CAGAACTTTAAAGAACCTAAAGATGGAGTTAGCAACAATGCGTCGAAAGA

AATCGGCATTAAAAATAATGATCTTTATTAGTGGATGCGTAACGTTAGCT

ACATCGATGGTTGGGGATTGAGTATCGTTGACGACGAAATATTAAGAGA

TTATAAGAACAACGATTGGTTAATGAAGACTATACATGGGCTGAATTTGT

TATGTACTACAGTTTTGTTAGCGGCGGGTAAGATTTCCGATAAAATGCAA

GAGGAGATTTCACGGACTAAACGTGACATTGCGAAAAGAGAGTCTTACGT

GTCAGCGGCGAGTATGTCGTGGAGTGGAGATACTGAGATGTTATTACAGG

GAATTAAGTATGGCGAGAGCTAGTATGACCTCCACGAGCGGAAAATCCAT

CGTGTTGGATGGATGGAACGCCTAGATCGTTTTCTAGGGAGTGGGATAAC

AACTTAC

*1) AUG->GCC mutations of start codons of NS3 and
NS3a and STOP codons downstream of AUG2:
                                          (SEQ ID NO: 90)
GTTAAAATTATCCCTTGTCGCCAATCTAGCTACAATCGCCAAGAATTATA

GCGCCCATAATGGAGAGTGAGGGGCGATCGTCCCTTAAGTGCCACCACCA

TAGAATTTCGCAAGTGCTCCGACGTTTTCTCAGCGTACGAGTCAAATGGA

GTCCGTGTCGCTTGGGATACTTAACCAAGCCATGTCAAGTACAACTGGTG

CGAGTGGGGCGCTTAAAGATGAAAAAGCAGCATTCGGTGCTATGGCGGAA

GCATTGCGTGATCCAGAACCCATACGTCAAATTAAAAAGCAGGTGGGTAT

CAGAACTTTAAAGAACCTAAAGATGGAGTTAGCAACAATGCGTCGAAAGA

AATCGGCATTAAAAATAATGATCTTTATTAGTGGATGCGTAACGTTAGCT

ACATCGATGGTTGGGGATTGAGTATCGTTGACGACGAAATATTAAGAGA

TTATAAGAACAACGATTGGTTAATGAAGACTATACATGGGCTGAATTTGT

TATGTACTACAGTTTTGTTAGCGGCGGGTAAGATTTCCGATAAAATGCAA

GAGGAGATTTCACGGACTAAACGTGACATTGCGAAAAGAGAGTCTTACGT

GTCAGCGGCGAGTATGTCGTGGAGTGGAGATACTGAGATGTTATTACAGG

GAATTAAGTATGGCGAGAGCTAGTATGACCTCCACGAGCGGAAAATCCAT

CGTGTTGGATGGATGGAACGCCTAGATCGTTTTCTAGGGAGTGGGATAAC

AACTTAC

*2) Deletion of the putative Late Domain resulting
in an out-of-frame mutation:
                                          (SEQ ID NO: 91)
GTTAAAATTATCCCTTGTCATGAATCTAGCTACAATCGCCAAGAATTATA

GCATGCATAATGGAGAGTCGGGGCGATCGTCCCTTATGTG---------

-----------------------GTTTTCTCAGCGTACGAGTCAAATGGA

GTCCGTGTCGCTTGGGATACTTAACCAAGCCATGTCAAGTACAACTGGTG

CGAGTGGGGCGCTTAAAGATGAAAAAGCAGCATTCGGTGCTATGGCGGAA

GCATTGCGTGATCCAGAACCCATACGTCAAATTAAAAAGCAGGTGGGTAT

CAGAACTTTAAAGAACCTAAAGATGGAGTTAGCAACAATGCGTCGAAAGA

AATCGGCATTAAAAATAATGATCTTTATTAGTGGATGCGTAACGTTAGCT

ACATCGATGGTTGGGGATTGAGTATCGTTGACGACGAAATATTAAGAGA

TTATAAGAACAACGATTGGTTAATGAAGACTATACATGGGCTGAATTTGT

TATGTACTACAGTTTTGTTAGCGGCGGGTAAGATTTCCGATAAAATGCAA

GAGGAGATTTCACGGACTAAACGTGACATTGCGAAAAGAGAGTCTTACGT

GTCAGCGGCGAGTATGTCGTGGAGTGGAGATACTGAGATGTTATTACAGG

GAATTAAGTATGGCGAGAGCTAGTATGACCTCCACGAGCGGAAAATCCAT

CGTGTTGGATGGATGGAACGCCTAGATCGTTTTCTAGGGAGTGGGATAAC

AACTTAC

*3) AUG->GCC mutation of all AUG codons in ORF of
NS3/NS3a:
                                          (SEQ ID NO: 92)
GTTAAAATTATCCCTTGTCGCCAATCTAGCTACAATCGCCAAGAATTATA

GCGCCCATAATGGAGAGTCGGGGCGATCGTCCCTTATGTGCCACCACCA

TACAATTTCGCAAGTGCTCCGACGTTTTCTCAGCGTACGAGTCAAGCCGA
```

```
GTCCGTGTCGCTTGGGATACTTAACCAAGCCGCCTCAAGTACAACTGGTG

CGAGTGGGGCGCTTAAAGATGAAAAAGCAGCATTCGGTGCTGCCGCGGAA

GCATTGCGTGATCCAGAACCCATACGTCAAATTAAAAAGCAGGTGGGTAT

CAGAACTTTAAAGAACCTAAAGGCCGAGTTAGCAACAGCCCGTCGAAAGA

AATCGGCATTAAAAATAGCCATCTTTATTAGTGGATGCGTAACGTTAGCT

ACATCGGCCGTTGGGGATTGAGTATCGTTGACGACGAAATATTAAGAGA

TTATAAGAACAACGATTGGTTAGCCAAGACTATACATGGGCTGAATTTGT

TATGTACTACAGTTTTGTTAGCGGCGGGTAAGATTTCCGATAAAGCCCAA

GAGGAGATTTCACGGACTAAACGTGACATTGCGAAAAGAGAGTCTTACGT

GTCAGCGGCGAGTGCCTCGTGGAGTGGAGATACTGAGGCCTTATTACAGG

GAATTAAGTATGGCGAGAGCTAGTATGACCTCCACGAGCGGAAAATCCAT

CGTGTTGGATGGATGGAACGCCTAGATCGTTTTCTAGGGAGTGGGATAAC

AACTTAC
```

*4) 1* + 3* and mutations in a conserved region as
possible target for a potential panAHSV S10 PCR
assay (NS3knockoutDIVA):
                                    (SEQ ID NO: 93)
```
GTTAAAATTATCCCTTGTCGCCAATCTAGCTACAATCGCCAAGAATTATA

GCGCCCATAATGGAGAGTGAGGGGCGATCGTCCCTTAAGTGCCACCACCA

TAGAATTTCGCAAGTGCTCCGACGTTTTCTCAGCGTACGAGTCAAGCCGA

AAGTGTAAGTTTAGGGATACTTAACCAAGCCGCCTCAAGTACAACTGGTG

CGAGTGGGGCGCTTAAAGATGAAAAAGCAGCATTCGGTGCTGCCGCGGAA

GCATTGCGTGATCCAGAACCCATACGTCAAATTAAAAAGCAGGTGGGTAT

CAGAACTTTAAAGAACCTAAAGGCCGAGTTAGCAACAGCCCGTCGAAAGA

AATCGGCATTAAAAATAGCCATCTTTATTAGTGGATGCGTAACGTTAGCT

ACATCGGCCGTTGGGGATTGAGTATCGTTGACGACGAAATATTAAGAGA

TTATAAGAACAACGATTGGTTAGCCAAGACTATACATGGGCTGAATTTGT

TATGTACTACAGTTTTGTTAGCGGCGGGTAAGATTTCCGATAAAGCCCAA

GAGGAGATTTCACGGACTAAACGTGACATTGCGAAAAGAGAGTCTTACGT

GTCAGCGGCGAGTGCCTCGTGGAGTGGAGATACTGAGGCCTTATTACAGG

GAATTAAGTATGGCGAGAGCTAGTATGACCTCCACGAGCGGAAAATCCAT

CGTGTTGGATGGATGGAACGCCTAGATCGTTTTCTAGGGAGTGGGATAAC

AACTTAC
```

*5) delTMR1: AUG1 + 2 in combination with a
deletion in Seg-10 encompassing transmembrane
region 1 (TM1):
                                    (SEQ ID NO: 94)
```
GTTAAAATTATCCCTTGTCATGAATCTAGCTACAATCGCCAAGAATTATA

GCGCCCATAATGGAGAGTCGGGGGCGATCGTCCCTTATGTGCCACCACCA

TACAATTTCGCAAGTGCTCCGACGTTTTCTCAGCGTAC------------

------------------------------------------------

------------------------------------------------

------------------------------------------------

------------------------------------------------

---TAAGAACAACGATTGGTTAATGAAGACTATACATGGGCTGAATTTGT

TATGTACTACAGTTTTGTTAGCGGCGGGTAAGATTTCCGATAAAATGCAA

GAGGAGATTTCACGGACTAAACGTGACATTGCGAAAAGAGAGTCTTACGT

GTCAGCGGCGAGTATGTCGTGGAGTGGAGATACTGAGATGTTATTACAGG

GAATTAAGTATGGCGAGAGCTAGTATGACCTCCACGAGCGGAAAATCCAT

CGTGTTGGATGGATGGAACGCCTAGATCGTTTTCTAGGGAGTGGGATAAC

AACTTAC
```

*6) delTMR2: AUG1 + 2in combination with a
deletion Deletion in Seg-10 encompassing trans-
membrane region 2 (TM2):
                                    (SEQ ID NO: 95)
```
GTTAAAATTATCCCTTGTCGCCAATCTAGCTACAATCGCCAAGAATTATAG

CGCCCATAATGGAGAGTCGGGGGCGATCGTCCCTTATGTGCCACCACCATA

CAATTTCGCAAGTGCTCCGACGTTTTCTCAGCGTACGAGTCAAATGGAGTC

CGTGTCGCTTGGGATACTTAACCAAGCCATGTCAAGTACAACTGGTGCGAG

TGGGGCGCTTAAAGATGAAAAAGCAGCATTCGGTGCTATGGCGGAAGCATT

GCGTGATCCAGAACCCATACGTCAAATTAAAAAGCAGGTGGGTATCAGAAC

TTTAAAGAACCTAAAGATGGAGTTAGCAACAATGCGTCGAAAGAAATCGGC

ATTAAAAATAATGATCTTTATTAGTGGATGCGTAACGTTAGCTACATCGAT

GGTTGGGGATTGAGTATCGTTGACGACGAAATATTAAGAGATTA------

------------------------------------------------

------------------------------------------------

---------------------------------GTGTCAGCGGCGAGT

ATGTCGTGGAGTGGAGATACTGAGATGTTATTACAGGGAATTAAGTATGGC

GAGAGCTAGTATGACCTCCACGAGCGGAAAATCCATCGTGTTGGATGGATG

GAACGCCTAGATCGTTTTCTAGGGAGTGGGATAACAACTTAC
```

Mutants of AHSV4LP with Seg-2[VP2] and Seg-6[VP5] encoding both outer shell proteins of different serotypes were generated (serotyped). Further, AHSV4LP mutants with Seg-2[VP2] of each of the nine AHSV serotypes were generated (AHSVxLP). Finally, combinations of mutated Seg-10 and Seg-2 of each of the nine AHSV serotypes were combined in AHSV4LP resulting in Seg-2 serotyped AHSV without expression from ORF-NS3 (AHS DISA vaccine x). Exchange of Seg-2 and mutations in Seg-10 were confirmed by (partial) sequencing of the respective genome segments. Overview of results is indicated in Table 5.

TABLE 5

| name | Seg-2 typed | Seg of AHSV4LP | mutation in Seg-10 | CPE | VP5* | VP2** | NS3*** |
|---|---|---|---|---|---|---|---|
| AHSV4LP | — | 1-10 | — | + | + | nd | + |
| AUG1 | — | 1-9 | AUG$^1$ -> GCC$^1$ | + | + | nd | + |
| AUG1+2 | — | 1-9 | AUG$^{1+2}$ -> GCC$^{1+2}$ | small | + | nd | − |
| mutAUG1 + 2 & STOPS | — | 1-9 | *1 | small | + | nd | − |
| delLD | — | 1-9 | *2 | small | + | nd | − |
| AUG total | — | 1-9 | *3 | − | + | nd | − |
| NS3knockout DIVA | — | 1-9 | *4 | − | + | nd | − |
| delTMR1 | — | 1-9 | *5 | − | + | nd | − |
| delTMR2 | — | 1-9 | *6 | − | + | nd | − |
| serotyped 3 | (VP2/VP5)$^3$ | 1, 3-5, 7-10 | — | + | nd | 3 | nd |
| AHSV4LP | — | 1-10 | — | + | + | 4 | + |
| serotyped 6 | (VP2/VP5)$^6$ | 1, 3-5, 7-10 | — | + | nd | 6 | nd |
| AHSV1LP | 1 | 1, 3-10 | — | + | nd | 1 | nd |
| AHSV2LP | 2 | 1, 3-10 | — | + | nd | 2 | nd |
| AHSV3LP | 3 | 1, 3-10 | — | + | nd | 3 | nd |
| AHSV4LP | — | 1-10 | — | + | + | 4 | + |
| AHSV5LP | 5 | 1, 3-10 | — | + | nd | 5 | nd |
| AHSV6LP | 6 | 1, 3-10 | — | + | nd | 6 | nd |
| AHSV7LP | 7 | 1, 3-10 | — | + | + | 7 | nd |
| AHSV8LP | 8 | 1, 3-10 | — | + | nd | 8 | nd |
| AHSV9LP | 9 | 1, 3-10 | — | + | nd | 9 | nd |
| AHSV1LP-(NS3/NS3a)$^{minus}$ | 1 | 1, 3-9 | *1 | small | nd | 1 | nd |
| AHSV8LP-(NS3/NS3a)$^{minus}$ | 8 | 1, 3-9 | *1 | small | nd | 8 | nd |
| AHS DISA vaccine 1 | 1 | 1, 3-9 | *4 | − | nd | 1 | − |
| AHS DISA vaccine 2 | 2 | 1, 3-9 | *4 | − | nd | 2 | − |
| AHS DISA vaccine 3 | 3 | 1, 3-9 | *4 | − | nd | 3 | − |
| AHS DISA vaccine 4 | — | 1-9 | *4 | − | nd | 4 | − |
| AHS DISA vaccine 5 | 5 | 1, 3-9 | *4 | − | nd | 5 | − |
| AHS DISA vaccine 6 | 6 | 1, 3-9 | *4 | − | nd | 6 | − |
| AHS DISA vaccine 7 | 7 | 1, 3-9 | *4 | − | nd | 7 | − |
| AHS DISA vaccine 8 | 8 | 1, 3-9 | *4 | − | nd | 8 | − |
| AHS DISA vaccine 9 | 9 | 1, 3-9 | *4 | − | nd | 9 | − |

CPE phenotype in BSR infected monolayers was scored as similar to AHSV4LP (+), smaller CPE plaques (small), or no CPE (−). IPMA was performed on infected monolayers with VPS serum, with sera raised against baculovirus expressed AHSV-VP2 proteins of each of the nine AHSV serotypes (VP2**) (Yuta et al., in prep.), or with MAbs raised against AHSV-NS3*/NS3a (+: staining, −: no staining, nd: not done). Mutations in Seg-10 are indicated by referring to the complete sequence as given above (*1 to *6), or no mutations (−).

Example 19

Mutants of BTV with mutated Seg-10 were used to map epitopes on NS3/NS3a proteins, as is indicated in Table 6.

TABLE 6

BTV mutants with mutated Seg-10 as described in previous examples were used to map epitopes on NS3/NS3a proteins. IPMA was performed on BSR monolayers infected with BTV mutants with MAbs raised against NS3/NS3a proteins. IPMA with MAb 1875 against VP7 served as positive control. (+: staining, −: no staining).

| BTV mutant | amino acid changes | virus rescue | VP7 1875 | NS3 33H7 | NS3 32H2 | NS3 32F1 | NS3 31E9 | NS3 32B6 |
|---|---|---|---|---|---|---|---|---|
| Wild type | none | Yes | + | + | + | + | + | + |
| Mut AUG1 | Met-4 −> Ala | Yes | + | + | + | + | + | + |
| Mut AUG2 | Met-14 −> Ala | Yes | + | + | + | + | + | + |
| Mut AUG1 + 2 | Met-1/Met-14 −> Ala/Ala | Yes | + | − | − | − | − | − |
| Mut-B | none | Yes | + | + | + | + | + | + |
| PSAP − >ASAP | YAPSAP − >YAASAP | Yes | + | + | + | − | − | + |
| PSAP − >GAAP | YAPSAP −> YAGAAP | Yes | + | + | + | − | − | + |
| S-rev-1 | PPRYAP −> PP(A)RYAP | Yes | + | − | + | + | + | − |
| S-rev-2 | PPRYAP −> (H)QRYAP | Yes | + | − | + | + | + | − |
| TM1 | ALL −> EEE | Yes | + | + | + | + | + | + |
| N149S | NGT −> SGT | Yes | + | + | + | + | + | + |
| CT4-212 | Arg −> STP-212 | Yes | + | + | + | + | + | + |
| B-rev-1 | FASYAE −> FASY(V)AE | Yes | + | + | + | + | + | + |
| BPS2 | truncated at Met-14 | Yes | + | − | − | − | − | − |

Example 20 Expression of NS3

NS3 ELISA. Available full length nucleotide sequences of genome segment 10 (Seg-10) were putatively translated to NS3/NS3a proteins and compared by freely available software program 'protein blast', which is available at (http://blast.ncbi.nlm.nih.gov).

The comparison showed that many regions in NS3/NS3a proteins are highly conserved among 24 recognized serotypes within the BTV serogroup, such as the immunogenic Late Domain region QPPRYAPSAP (position 35-44) in which MAbs 33H7, 32F1, 31E9 and 32B6 have been mapped.

Figure 10:
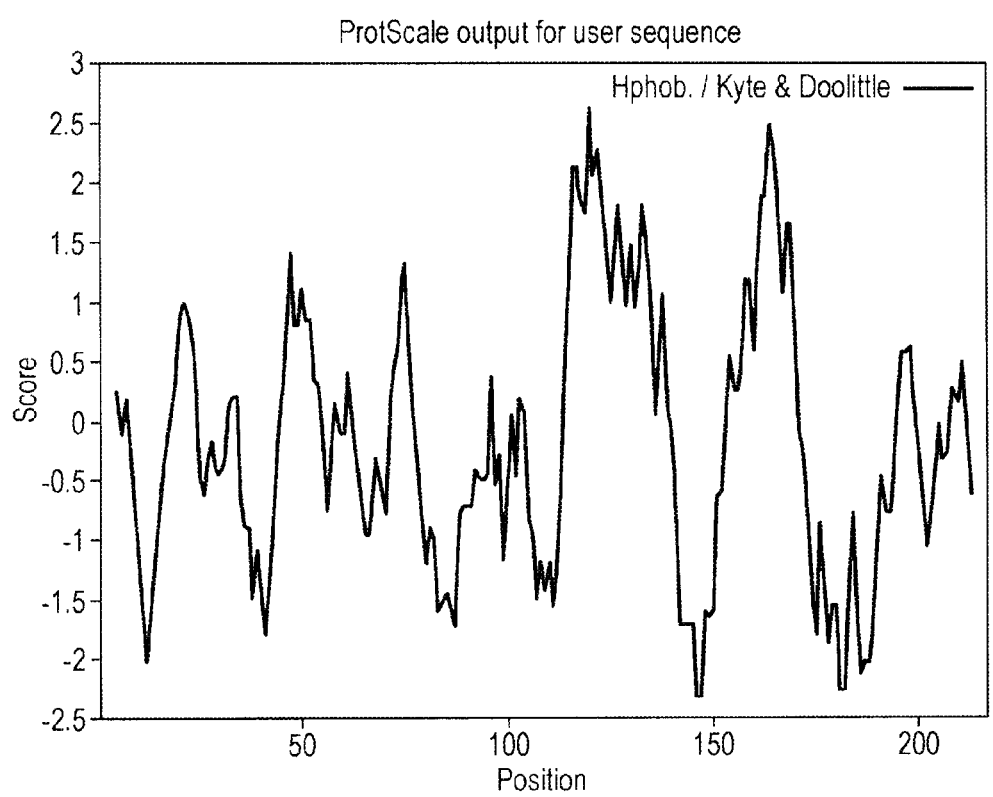

A hydrophobicity plot is indicated in FIG. 10. The sequence encoding TMR1, EC and TMR2 (aa 117-183) in the NS3 open reading frame of Seg-10 was removed by an in-frame deletion in BTV8)NS3ΔTM to increase NS3 antigen production in bacteria.

BTV8)NS3ΔTM:
(SEQ ID NO: 96)
ATGCTGTCGGGTCTGATCCAACGCTTTGAAGAAGAAAAAATGAAACATA

ACCAAGATCGTGTCGAAGAACTGTCACTGGTCCGTGTGGATGACACCAT

TTCACAGCCGCCGCGTTATGCACCGTCGGCTCCGATGCCGAGCTCTATG

CCGACCGTTGCCCTGGAAATCCTGGATAAAGCAATGTCTAACACCACGG

GCGCAACCCAGACGCAAAAGGCTGAAAAAGCGGCCTTTGCGAGCTACGC

GGAAGCCTTCCGTGATGACGTTCGTCTGCGCCAGATTAAACGCCATGTC

AATGAACAAATCCTGCCGAAGCTGAAAAGCGATCTGTCTGGCCTGAAAA

AGAAA----------------------------------------

----------------------------------------------

----------------------------------------------

----------------------------------------------

----------AGTGAACGTGCCCTGAACCAGCAAATCGATATGATCAAG

AAAGAAGTCATGAAGAAACAGAGCTATAATGACGCCGTGCGCATGTCTT

TTACCGAATTCTCATCGGTTCCGCTGGATGGTTTCGAAATGCCGCTGAC

G*

Deletion Seg-10 cloned in pET-51b(+)Ek/LIC for bacterial expression of truncated NS3 antigen (BTV8)NS3ΔTM according to the supplier. Start codons of NS3 and NS3a are indicated in bold/underlined and the STOP codon is indicated by *.

Figure 11:
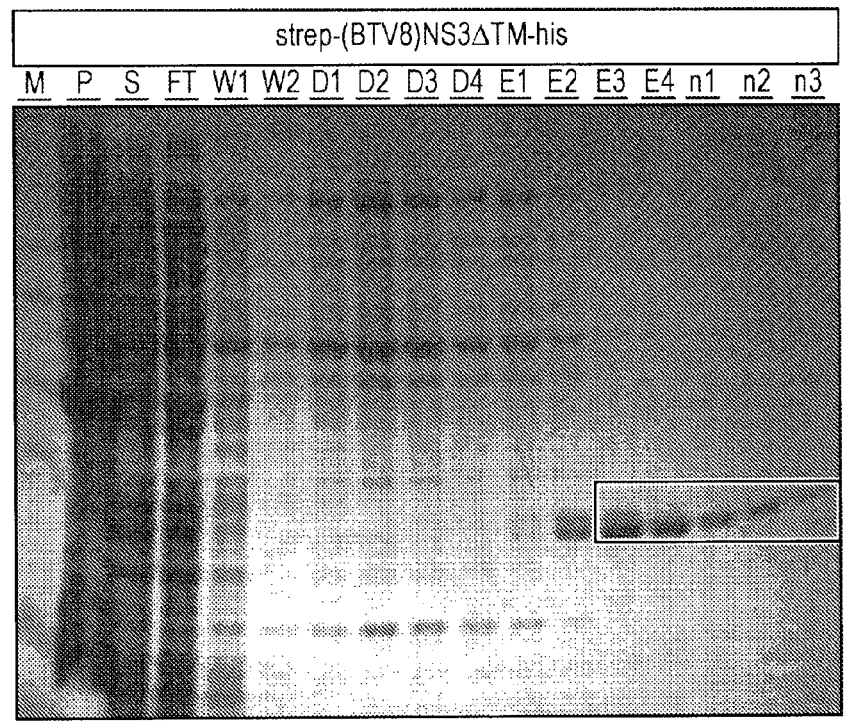

Expression and purification of truncated NS3 antigen (BTV8)NS3 ΔTM is shown in FIG. 11.

Plasmid pET-51(+)Ek/LIC expressing truncated NS3 antigen originating from BTV8/net06 was used for production. Regions encoding TM1, EC and TM2 were deleted by in-frame deletion to increase production of immunogenic parts of NS3, such as the immunogenic Late Domain region QPPRYAPSAP in which MAbs 33H7, 32F1, 31E9 and 32B6 are mapped. Indicated fractions were separated by polyacrylamide gel electrophoresis and proteins were detected by standardized Coomassie Brilliant Blue staining. Typically, truncated NS3 antigen was purified and eluted in a concentration of 100-200 ug/ml.

Example 21

A competitive ELISA was developed for detection of antibodies directed against NS3/NS3a (NS3 ELISA), in particularly those competing for binding with MAb 33H7. Therefore, truncated NS3 was produced in bacteria and after purification used as antigen (see Example 20). NS3 antigen was bound to the bottom of ELISA plates (coating). After pre-incubation with serum samples (from sheep trials as described in previous examples), plates were washed and incubation was continued with mouse MAb 33H7 to occupy free epitopes on coated NS3 antigen (competition). After extensive washing to remove unbound MAb 33H7, incubation was continued with commercially available rabbit anti-mouse IgG Abs conjugated with peroxidase. After washing to remove free conjugated Abs, staining with TMB was performed according to standard procedures. Seroconversion as determined by NS3-ELISA is presented as (100−x) % with a threshold value set on 50% (see FIGS. 7G and 9G).

The invention claimed is:

1. A propagation-competent strain of a mutant Orbivirus, comprising a mutation of translational start codons of NS3 and NS3a, and/or comprising a deletion of at least 10 nucleotides between the translational start codon of NS3a and translational stop codon of NS3a, that abolish expression of endogenous NS3 and NS3a proteins, which mutant Orbivirus is able to propagate in a non-complementing cell line.

2. The propagation-competent strain according to claim 1, comprising a deletion of at least 10 nucleotides between the translational start codon of NS3a and translational stop codon of NS3a, in the coding region of the NS3/NS3a glycoprotein.

3. The propagation-competent strain according to claim 1, wherein said functional deletion is an alteration of an ATG translation start codon of NS3 and of NS3a.

4. The propagation-competent strain according to claim 1, which is Bluetongue virus or African horse sickness virus.

5. A vaccine, comprising the propagation-competent strain according to claim 1.

6. The vaccine according to claim 5, which is a Differentiating Infected animals from Vaccinated Animals (DIVA) vaccine.

7. The vaccine according to claim 5, wherein the propagation-competent strain is a modified live virus.

8. The propagation-competent strain according to claim 1, wherein said functional deletion is a deletion of the coding region of a NS3a glycoprotein.

* * * * *